(12) United States Patent
Wochner et al.

(10) Patent No.: US 10,837,039 B2
(45) Date of Patent: Nov. 17, 2020

(54) METHODS AND MEANS FOR ENHANCING RNA PRODUCTION

(71) Applicant: CureVac Real Estate GmbH, Tübingen (DE)

(72) Inventors: Aniela Wochner, Tübingen (DE); Tilmann Roos, Kusterdingen (DE); Thomas Ketterer, Gomaringen (DE)

(73) Assignee: CureVac Real Estate GmbH, Tübingen (DE)

(*) Notice: Subject to any disclaimer, the term of this patent is extended or adjusted under 35 U.S.C. 154(b) by 0 days.

(21) Appl. No.: 15/317,579

(22) PCT Filed: Jun. 10, 2015

(86) PCT No.: PCT/EP2015/001164
§ 371 (c)(1),
(2) Date: Dec. 9, 2016

(87) PCT Pub. No.: WO2015/188933
PCT Pub. Date: Dec. 17, 2015

(65) Prior Publication Data
US 2017/0114378 A1    Apr. 27, 2017

(51) Int. Cl.
| | | |
|---|---|---|
| C12P 19/34 | (2006.01) | |
| C12Q 1/6844 | (2018.01) | |
| C12M 1/00 | (2006.01) | |
| C12M 1/40 | (2006.01) | |
| C12M 3/00 | (2006.01) | |
| C12M 1/34 | (2006.01) | |
| C12M 1/36 | (2006.01) | |

(52) U.S. Cl.
CPC .......... *C12P 19/34* (2013.01); *C12M 21/18* (2013.01); *C12M 23/44* (2013.01); *C12M 29/04* (2013.01); *C12M 29/14* (2013.01); *C12M 29/18* (2013.01); *C12M 41/26* (2013.01); *C12M 41/32* (2013.01); *C12M 41/48* (2013.01); *C12Q 1/6844* (2013.01)

(58) Field of Classification Search
CPC .. A61K 31/519; A61K 2300/00; A61K 45/06; C12Q 1/6844; C12Q 2521/119; C12Q 2525/117; C12Q 2527/113; C12Q 2527/137; C12P 19/34
See application file for complete search history.

(56) References Cited

U.S. PATENT DOCUMENTS

| | | |
|---|---|---|
| 6,586,218 B2 | 7/2003 | Milburn et al. |
| 2005/0032730 A1 | 2/2005 | Von der Mulbe et al. |
| 2005/0059624 A1 | 3/2005 | Hoerr et al. |
| 2005/0064465 A1 | 3/2005 | Dettloff et al. |
| 2005/0250723 A1 | 11/2005 | Hoerr et al. |
| 2006/0188490 A1 | 8/2006 | Hoerr et al. |
| 2008/0025944 A1 | 1/2008 | Hoerr et al. |
| 2008/0267873 A1 | 10/2008 | Hoerr et al. |
| 2009/0324584 A1 | 12/2009 | Hoerr et al. |
| 2010/0048883 A1 | 2/2010 | Ketterer et al. |
| 2010/0189729 A1 | 7/2010 | Hoerr et al. |
| 2010/0203076 A1 | 8/2010 | Fotin-Mleczek et al. |
| 2010/0291156 A1 | 11/2010 | Barner et al. |
| 2010/0305196 A1 | 12/2010 | Probst et al. |
| 2011/0053829 A1 | 3/2011 | Baumhof et al. |
| 2011/0250225 A1 | 10/2011 | Fotin-Mleczek et al. |

(Continued)

FOREIGN PATENT DOCUMENTS

| | | |
|---|---|---|
| CN | 102597264 | 7/2012 |
| WO | WO 1995/008626 | 3/1995 |

(Continued)

OTHER PUBLICATIONS

Gruegelsiepe, H. et al., Enzymatic RNA Synthesis Using Bacteriophage T7 RNA Polymerase, Handbook of RNA Biochemistry, ed. R. K. Hartmann, Part I.1, pp. 3-21 (Year: 2005).*

(Continued)

*Primary Examiner* — Teresa E Strzelecka
(74) *Attorney, Agent, or Firm* — Parker Highlander PLLC

(57) ABSTRACT

The present invention relates to a method for synthesizing an RNA molecule of a given sequence, comprising the step of determining the fraction (1) for each of the four nucleotides G, A, C and U in said RNA molecule, and the step of synthesizing said RNA molecule by in vitro transcription in a sequence-optimized reaction mix, wherein said sequence-optimized reaction mix comprises the four ribonucleoside triphosphates GTP, ATP, CTP and UTP, wherein the fraction (2) of each of the four ribonucleoside triphosphates in the sequence-optimized reaction mix corresponds to the fraction (1) of the respective nucleotide in said RNA molecule, a buffer, a DNA template, and an RNA polymerase. Further, the present invention relates to a bioreactor (1) for synthesizing RNA molecules of a given sequence, the bioreactor (1) having a reaction module (2) for carrying out in vitro RNA transcription reactions in a sequence-optimized reaction mix, a capture module (3) for temporarily capturing the transcribed RNA molecules, and a control module (4) for controlling the infeed of components of the sequence-optimized reaction mix into the reaction module (2), wherein the reaction module (2) comprises a filtration membrane (21) for separating nucleotides from the reaction mix, and the control of the infeed of components of the sequence-optimized reaction mix by the control module (4) is based on a measured concentration of separated nucleotides.

18 Claims, 24 Drawing Sheets

Specification includes a Sequence Listing.

(56) References Cited

U.S. PATENT DOCUMENTS

| | | |
|---|---|---|
| 2012/0021043 A1 | 1/2012 | Kramps et al. |
| 2012/0258046 A1 | 10/2012 | Mutzke |
| 2013/0129754 A1 | 5/2013 | Thess et al. |
| 2013/0142818 A1 | 6/2013 | Baumhof et al. |
| 2013/0259879 A1 | 10/2013 | Baumhof et al. |
| 2013/0280283 A1 | 10/2013 | Lorenz et al. |
| 2013/0295043 A1 | 11/2013 | Kallen et al. |
| 2013/0336998 A1 | 12/2013 | Kallen et al. |
| 2015/0037326 A1 | 2/2015 | Butler-Ransohoff et al. |
| 2015/0050302 A1 | 2/2015 | Thess |
| 2015/0057340 A1 | 2/2015 | Thess et al. |
| 2015/0093413 A1 | 4/2015 | Thess et al. |
| 2015/0118183 A1 | 4/2015 | Baumhof |
| 2015/0118264 A1 | 4/2015 | Baumhof et al. |
| 2015/0165006 A1 | 6/2015 | Thess et al. |
| 2015/0184195 A1 | 7/2015 | Thess et al. |
| 2015/0218554 A1 | 8/2015 | Thess |
| 2015/0306249 A1 | 10/2015 | Baumhof et al. |
| 2015/0320847 A1 | 11/2015 | Thess et al. |
| 2016/0130345 A1 | 5/2016 | Fotin-Mleczek et al. |
| 2016/0166668 A1 | 6/2016 | Kallen et al. |
| 2016/0166678 A1 | 6/2016 | Kallen et al. |
| 2016/0166710 A1 | 6/2016 | Baumhof |
| 2016/0166711 A1 | 6/2016 | Schnee et al. |
| 2016/0168207 A1 | 6/2016 | Kramps et al. |
| 2016/0168227 A1 | 6/2016 | Kallen et al. |
| 2016/0235864 A1 | 8/2016 | Schlake et al. |
| 2016/0304883 A1 | 10/2016 | Grund et al. |
| 2016/0304938 A1 | 10/2016 | Wochner |
| 2016/0326575 A1 | 11/2016 | Von der Mulbe et al. |
| 2016/0331844 A1 | 11/2016 | Fotin-Mleczek et al. |
| 2017/0014496 A1 | 1/2017 | Fotin-Mleczek et al. |
| 2017/0029847 A1 | 2/2017 | Thess |

FOREIGN PATENT DOCUMENTS

| | | |
|---|---|---|
| WO | WO 2004/022574 | 3/2004 |
| WO | WO 2006/004648 | 1/2006 |
| WO | WO 2011/048198 | 4/2011 |
| WO | WO 2015/149944 | 10/2015 |
| WO | WO 2016/091391 | 6/2016 |
| WO | WO 2016/097065 | 6/2016 |
| WO | WO 2016/107877 | 7/2016 |

OTHER PUBLICATIONS

Ambion Catalog No. AM8110G-AM8140G, Ribonucleic Acid Triphospates, p. 1 (Year: 2007).*

Jani, B. et al., In vitro Transcription and Capping of Gaussia Luciferase mRNA followed by HeLa Cell Transfection, J. Vis. Exp., vol. 61, e3702, pp. 1-9 (Year: 2012).*

Munroe, D. et al., mRNA Poly(a) TAil, a 3' Enhancer of Translational Initiation, Mol. Cel. Biol., vol. 10, pp. 3441-3455 (Year: 1990).*

Kern et al., "Application of solution equilibrium analysis to in vitro RNA transcription," *Biotechnology Progress*, 13(6):747-756, 1997.

PCT International Search Report and Written Opinion issued in International Application No. PCT/EP2015/001164, dated Sep. 22, 2015.

Gößringer et al. "Enzymatic RNA synthesis using bacteriophage T7 RNA polymerase," *Handbook of RNA Biochemistry*, Second Edition, pp. 3-27, 2014.

Melton et al., "Efficient in vitro synthesis of biologically active RNA and RNA hybridization probes from plasmids containing a bacteriophage SP6 promoter," *Nucleic Acids Research*, 12(18):7035-7056, 1984.

Schneider et al., "Measuring Control of Transcription Initiation by Changing Concentrations of Nucleotids and Their Derivatives", *Methods Enzymol.*, 370:606-617, 2003.

* cited by examiner

SEQ ID NO. 1: R1871 HsPSCA

GGGAGAAAGCUUACCAUGAAGGCCGUGCUGCUCGCGCUGCUGAUGGCCGGCCUGGCCCUGCAGCCGGGGACCGCC
CUGCUGUGCUACAGCUGCAAGGCCCAGGUCUCGAACGAGGACUGCCUGCAGGUGGAGAACUGCACGCAGCUGGGC
GAGCAGUGCUGGACCGCCCGGAUCCGCGCCGUGGGCCUGCUCACCGUGAUCAGCAAGGGCUGCAGCCUGAACUGC
GUGGACGACAGCCAGGACUACUACGUGGGCAAGAAGAACAUCACCUGCUGCGACACCGACCUGUGCAACGCCAGC
GGCGCCCACGCCCUGCAGCCCGCGGCCGCCAUCCUGGCCCUGCUGCCCGCCCUGGGCCUGCUGCUCUGGGGCCCC
GGCCAGCUGUGACCACUAGUUAUAAGACUGACUAGCCCGAUGGGCCUCCCAACGGGCCCUCCUCCCCUCCUUGCA
CCGAGAUUAAUAAAAAAAAAAAAAAAAAAAAAAAAAAAAAAAAAAAAAAAAAAAAAAAAAAAAAAAAAAAAAAAA
UGCAUCCCCCCCCCCCCCCCCCCCCCCCCCCCCAAAGGCUCUUUUCAGAGCCACCAGAAUU

Fig. 1

SEQ ID NO. 2: R2988 PpLuc

GGGAGAAAGCUUACCAUGGAGGACGCCAAGAACAUCAAGAAGGGCCCGGCGCCCUUCUACCCGCUGGAGGACGGG
ACCGCCGGCGAGCAGCUCCACAAGGCCAUGAAGCGGUACGCCCUGGUGCCGGGCACGAUCGCCUUCACCGACGCC
CACAUCGAGGUCGACAUCACCUACGCGGAGUACUUCGAGAUGAGCGUGCGCCUGGCCGAGGCCAUGAAGCGGUAC
GGCCUGAACACCAACCACCGGAUCGUGGUGUGCUCGGAGAACAGCCUGCAGUUCUUCAUGCCGGUGCUGGGCGCC
CUCUUCAUCGGCGUGGCCGUCGCCCCGGCGAACGACAUCUACAACGAGCGGGAGCUGCUGAACAGCAUGGGGAUC
AGCCAGCCGACCGUGGUGUUCGUGAGCAAGAAGGGCCUGCAGAAGAUCCUGAACGUGCAGAAGAAGCUGCCCAUC
AUCCAGAAGAUCAUCAUCAUGGACAGCAAGACCGACUACCAGGGCUUCCAGUCGAUGUACACGUUCGUGACCAGC
CACCUCCCGCCGGGCUUCAACGAGUACGACUUCGUCCCGGAGAGCUUCGACCGGGACAAGACCAUCGCCCUGAUC
AUGAACAGCAGCGGCAGCACCGGCCUGCCGAAGGGGGUGGCCCUGCCGCACCGGACCGCCUGCGUGCGCUUCUCG
CACGCCCGGGACCCCAUCUUCGGCAACCAGAUCAUCCCGGACACCGCCAUCCUGAGCGUGGUGCCGUUCCACCAC
GGCUUCGGCAUGUUCACGACCCUGGGCUACCUCAUCUGCGGCUUCCGGGUGGUCCUGAUGUACCGGUUCGAGGAG
GAGCUGUUCCUGCGGAGCCUGCAGGACUACAAGAUCCAGAGCGCGCUGCUCGUGCCGACCCUGUUCAGCUUCUUC
GCCAAGAGCACCCUGAUCGACAAGUACGACCUGUCGAACCUGCACGAGAUCGCCAGCGGGGCGCCCCGCUGAGC
AAGGAGGUGGGCGAGGCCGUGGCCAAGCGGUUCCACCUCCCGGGCAUCCGCCAGGGCUACGGCCUGACCGAGACC
ACGAGCGCGAUCCUGAUCACCCCCGAGGGGGACGACAAGCCGGGCGCCGUGGGCAAGGUGGUCCCGUUCUUCGAG
GCCAAGGUGGUGGACCUGGACACCGGCAAGACCCUGGGCGUGAACCAGCGGGGCGAGCUGUGCGUGCGGGGGCCG
AUGAUCAUGAGCGGCUACGUGAACAACCCGGAGGCCACCAACGCCCUCAUCGACAAGGACGGCUGGCUGCACAGC
GGCGACAUCGCCUACUGGGACGAGGACGAGCACUUCUUCAUCGUCGACCGGCUGAAGUCGCUGAUCAAGUACAAG
GGCUACCAGGUGGCGCCGGCCGAGCUGGAGAGCAUCCUGCUCCAGCACCCCAACAUCUUCGACGCCGGCGUGGCC
GGGCUGCCGGACGACGACGCCGGCGAGCUGCCGGCCGCGGUGGUGGUGCUGGAGCACGGCAAGACCAUGACGGAG
AAGGAGAUCGUCGACUACGUGGCCAGCCAGGUGACCACCGCCAAGAAGCUGCGGGGCGGCGUGGUGUUCGUGGAC
GAGGUCCCGAAGGGCCUGACCGGGAAGCUCGACGCCCGGAAGAUCCGCGAGAUCCUGAUCAAGGCCAAGAAGGGC
GGCAAGAUCGCCGUGUGAGGACUAGUUAUAAGACUGACUAGCCCGAUGGGCCUCCCAACGGGCCCUCCUCCCCUC
CUUGCACCGAGAUUAAUAAAAAAAAAAAAAAAAAAAAAAAAAAAAAAAAAAAAAAAAAAAAAAAAAAAAAAAAAA
AAAAAAUGCAUCCCCCCCCCCCCCCCCCCCCCCCCCCCCCCAAAGGCUCUUUUCAGAGCCACCAGAAUU

Fig. 2

SEQ ID NO. 3: R1626 EGFR/Mucin-1

GGGAGAAAGCUUACCAUGACCCCCGGCACCCAGAGCCCGUUCUUCCUGCUCCUGCUGCUCACGGUGCUGACCGUC
GUGACCGGGAUGCGGCCGAGCGGCACCGCCGGGGCGGCCCUGCUCGCCCUGCUGGCCGCCCUGUGCCCCGCCUCG
CGCGCGCUGGAGGAGAAGAAGGUGUGCCAGGGCACGAGCAACAAGCUGACCCAGCUCGGCACCUUCGAGGACCAC
UUCCUGAGCCUGCAGCGGAUGUUCAACAACUGCGAGGUCGUGCUGGGCAACCUGGAGAUCACCUACGUGCAGCGG
AACUACGACCUGAGCUUCCUCAAGACCAUCCAGGAGGUGGCCGGCUACGUGCUGAUCGCCCUGAACACCGUGGAG
CGGAUCCCGCUGGAGAACCUGCAGAUCAUCCGGGGCAACAUGUACUACGAGAACAGCUACGCCCUGGCCGUCCUC
AGCAACUACGACGCCAACAAGACGGGGCUGAAGGAGCUGCCGAUGCGGAACCUGCAGGAGAUCCUGCACGGCGCG
GUGCGCUUCUCGAACAACCCGGCCCUGUGCAACGUGGAGAGCAUCCAGUGGCGGGACAUCGUGAGCAGCGACUUC
CUCAGCAACAUGAGCAUGGACUUCCAGAACCACCUGGGCUCGUGCCAGAAGUGCGACCCGAGCUGCCCGAACGGC
AGCUGCUGGGGCGCCGGCGAGGAGAACUGCCAGAAGCUGACCAAGAUCAUCUGCGCCCAGCAGUGCAGCGGGCGG
UGCCGGGGCAAGAGCCCCAGCGACUGCUGCCACAACCAGUGCGCCGCCGGCUGCACCGGCCCGCGGGAGUCGGAC
UGCCUGGUGUGCCGGAAGUUCCGCGACGAGGCGACCUGCAAGGACACCUGCCCGCCGCUGAUGCUGUACAACCCG
ACCACGUACCAGAUGGACGUGAACCCGGAGGGCAAGUACAGCUUCGGCGCCACCUGCGUCAAGAAGUGCCCCCGG
AACUACGUGGUGACCGACCACGGGAGCUGCGUGCGGGCCUGCGGCGCCGACAGCUACGAGAUGGAGGAGGACGGC
GUGCGGAAGUGCAAGAAGUGCGAGGGCCCGUGCCGGAAGGUGUGCAACGGCAUCGGCAUCGGGGAGUUCAAGGAC
AGCCUCAGCAUCAACGCCACCAACAUCAAGCACUUCAAGAACUGCACCUCGAUCAGCGGCGACCUGCACAUCCUG
CCGGUCGCCUUCCGGGGCGACAGCUUCACCCACACGCCGCCGCUGGACCCGCAGGAGCUGGACAUCCUGAAGACC
GUGAAGGAGAUCACCGGCUUCCUCCUGAUCCAGGCGUGGCCCGAGAACCGCACCGACCUGCACGCCUUCGAGAAC
CUGGAGAUCAUCCGGGGCCGGACCAAGCAGCACGGCCAGUUCAGCCUGGCCGUGGUGAGCCUGAACAUCACCAGC
CUCGGGCUGCGGUCGCUGAAGGAGAUCAGCGACGGCGACGUGAUCAUCAGCGGCAACAAGAACCUGUGCUACGCC
AACACGAUCAACUGGAAGAAGCUGUUCGGCACCAGCGGCCAGAAGACCAAGAUCAUCAGCAACCGGGGCGAGAAC
AGCUGCAAGGCCACCGGGCAGGUGUGCCACGCCCUGUGCUCGCCGGAGGGCUGCUGGGGCCCGGAGCCGCGGGAC
UGCGUCAGCUGCCGCAACGUGAGCCGGGGCCGGGAGUGCGUGGACAAGUGCAACCUCCUGGAGGGCGAGCCGCGG
GAGUUCGUGGAGAACAGCGAGUGCAUCCAGUGCCACCCGGAGUGCCUGCCCCAGGCGAUGAACAUCACCUGCACC
GGCCGGGGGCCGGACAACUGCAUCCAGUGCGCCCACUACAUCGACGGCCCGCACUGCGUGAAGACGUGCCCGGCC
GGCGUGAUGGGCGAGAACAACACCCUGGUCUGGAAGUACGCCGACGCCGGCCACGUGUGCCACCUGUGCCACCCG
AACUGCACCUACGGCUGCACCGGGCCGGGCCUGGAGGGCUGCCCCACCAACGGCCCGAAGAUCCCGAGCAUCGCC
ACCGGCAUGGUGGGCGCGCUCCUGCUGCUGCUGGUGGUGGCCCUGGGGAUCGGCCUCUUCAUGCGGCGCCGGCAC
AUCGUGCGGAAGCGGACGCUGCGGCGGCUGCUGCAGGAGCGCGAGCUGGUCGAGCCGCUGACCCCGAGCGGCGAG
GCCCCGAACCAGGCCCUCCUGCGGAUCCUGAAGGAGACCGAGUUCAAGAAGAUCAAGGUGCUGGGCUCGGGCGCC
UUCGGCACCGUGUACAAGGGGCUGUGGAUCCCCGAGGGCGAGAAGGUGAAGAUCCCGGUGGCCAUCAAGGAGCUG
CGGGAGGCGACCAGCCCGAAGGCCAACAAGGAGAUCCUCGACGAGGCCUACGUGAUGGCCAGCGUCGACAACCCG
CACGUGUGCCGGCUGCUGGGCAUCUGCCUGACCAGCACGGUGCAGCUGAUCACCCAGCUGAUGCCGUUCGGCUGC
CUCCUGGACUACGUGCGGGAGCACAAGGACAACAUCGGCAGCCAGUACCUGCUGAACUGGUGCGUGCAGAUCGCC

Fig. 3

```
AAGGGCAUGAACUACCUGGAGGACCGGCGCCUGGUGCACCGGGACCUCGCCGCGCGGAACGUCCUGGUGAAGACC
CCGCAGCACGUGAAGAUCACCGACUUCGGGCUGGCCAAGCUGCUGGGCGCCGAGGAGAAGGAGUACCACGCCGAG
GGCGGCAAGGUGCCCAUCAAGUGGAUGGCCCUGGAGAGCAUCCUCCACCGGAUCUACACCCACCAGUCGGACGUG
UGGAGCUACGGCGUGACCGUCUGGGAGCUGAUGACGUUCGGCAGCAAGCCGUACGACGGGAUCCCGGCCAGCGAG
AUCAGCAGCAUCCUGGAGAAGGGCGAGCGGCUGCCGCAGCCGCCGAUCUGCACCAUCGACGUGUACAUGAUCAUG
GUGAAGUGCUGGAUGAUCGACGCGGACUCGCGGCCCAAGUUCCGCGAGCUGAUCAUCGAGUUCAGCAAGAUGGCC
CGGGACCCGCAGCGGUACCUGGUGAUCCAGGGCGACGAGCGGAUGCACCUCCCGAGCCCGACCGACAGCAACUUC
UACCGGGCCCUGAUGGACGAGGAGGACAUGGACGACGUGGUGGACGCCGACGAGUACCUGAUCCCGCAGCAGGGC
UUCUUCAGCAGCCCGUCGACCAGCCGGACCCCGCUGCUGAGCAGCCUGAGCGCCACCAGCAACAACUCGACGGUC
GCCUGCAUCGACCGCAACGGCCUCCAGAGCUGCCCCAUCAAGGAGGACAGCUUCCUGCAGCGGUACAGCAGCGAC
CCGACCGGCGCGCUGACCGAGGACAGCAUCGACGACACCUUCCUGCCGGUGCCGGAGUACAUCAACCAGUCGGUG
CCGAAGCGGCCCGCCGGGAGCGUGCAGAACCCGGUGUACCACAACCAGCCGCUGAACCCGGCCCCGAGCCGGGAC
CCGCACUACCAGGACCCCCACAGCACCGCCGUGGGCAACCCGGAGUACCUGAACACCGUCCAGCCGACGUGCGUG
AACAGCACCUUCGACAGCCCGGCCCACUGGGCCCAGAAGGGCUCGCACCAGAUCAGCCUCGACAACCCGGACUAC
CAGCAGGACUUCUUCCCGAAGGAGGCGAAGCCCAACGGCAUCUUCAAGGGCAGCACCGCCGAGAACGCCGAGUAC
CUGCGGGUGGCCCCGCAGAGCAGCGAGUUCAUCGGCGCCUCCGGCCACGCCAGCUCCACCCCCGGGGGCGAGAAG
GAGACGAGCGCCACCCAGCGGUCCAGCGUGCCCUCCAGCACCGAGAAGAACGCGGUCUCCAUGACCAGCUCCGUG
CUGAGCUCCCACAGCCCCGGGUCCGGCAGCUCCACGACCCAGGGCCAGGACGUGACCCUCGCCCCGGCCACCGAG
CCCGCCAGCGGGUCCGCCGCGACGUGGGGCCAGGACGUCACCAGCGUGCCCGUGACCCGCCCCGCCCUGGGGAGC
ACCACGCCGCCCGCCCACGACGUCACCUCCGCCCCCGACAACAAGCCCGCGCCGGGCAGCACCGCCCCCCCCGCC
CACGGGGUGACCUCCGCCCCCGACACGCGGCCGGCCCCCGGCAGCACCGCGCCCCCCGCCCACGGCGUGACCUCC
GCCCCGGACACCCGCCCGGCCCCCGGCAGCACCGCCCCCCCCGCCCACGGGGUGACCUCCGCCCCGGACACGCGG
CCCGCCCCGGCAGCACCGCCCCGCCCGCCCACGGCGUCACGUCCGCGCCCGACAACCGCCCCGCCCUGGGGAGC
ACCGCCCCGCCCGUGCACAACGUGACCUCCGCCAGCGGCUCCGCGAGCGGGUCCGCCAGCACCCUCGUCCACAAC
GGCACGUCCGCCCGGGCCACCACCACCCCCGCCAGCAAGUCCACGCCCUUCAGCAUCCCGUCCCACCACAGCGAC
ACCCCCACCACCCUGGCGUCCCACAGCACGAAGACCGACGCCUCCAGCACCCACCACUCCAGCGUGCCCCGCUG
ACCAGCUCCAACCACAGCACGUCCCCGCAGCUCAGCACCGGGGUGUCCUUCUUCUUCCUGAGCUUCCACAUCUCC
AACCUGCAGUUCAACAGCUCCCUCGAGGACCCCAGCACCGACUACUACCAGGAGCUGCAGCGGGACAUCUCCGAG
AUGUUCCUGCAGAUCUACAAGCAGGGCGGCUUCCUCGGGCUGAGCAACAUCAAGUUCCGCCCCGGCUCCGUCGUG
GUGCAGCUGACCCUCGCCUUCCGGGAGGGGACGAUCAACGUCCACGACGUGGAGACCCAGUUCAACCAGUACAAG
ACCGAGGCCGCCAGCCGCUACAACCUGACCAUCUCCGACGUGAGCGUCUCCGACGUGCCCUUCCCGUUCAGCGCG
CAGUCCGGCGCCGGCGUGCCCGGGGCCGUGUGCCAGUGCCGGCGCAAGAACUACGGGCAGCUCGACAUCUUCCCC
GCCCGGGACACGUACCACCCGAUGAGCGAGUACCCGACCUACCACACCCACGGCCGCUACGUCCCCCCCAGCUCC
ACCGACCGGAGCCCCUACGAGAAGGUGUCCGCCGGGAACGGCGGCAGCUCCCUGAGCUACACCAACCCGGCGGUG
GCCGCCGCCUCCGCCAACCUGGAGGACCAGGUGGACCCCCGGCUGAUCGACGGCAAGUGAGGACUAGUUAUAAGA
CUGACUAGCCCGAUGGGCCUCCCAACGGGCCCUCCUCCCCUCCUUGCACCGAGAUUAAUAAAAAAAAAAAAAAA
AAAAAAAAAAAAAAAAAAAAAAAAAAAAAAAAAAAAAAAAAAAAAAAAUAUUCCCCCCCCCCCCCCCCCCCCCC
CCCCCCCUCUAG
```

Fig. 3 continued

SEQ ID NO. 4: R2025

GGGAGAAAGCUCAAGCUUAUCCAAGUAGGCUGGUCACCUGUACAACGUAGCCGGUAUUUUUUUUUUUUUUUUUUU
UUUGACCGUCUCAAGGUCCAAGUUAGUCUGCCUAUAAAGGUGCGGAUCCACAGCUGAUGAAAGACUUGUGCGGUA
CGGUUAAUCUCCCCUUUUUUUUUUUUUUUUUUUUAGUAAAUGCGUCUACUGAAUCCAGCGAUGAUGCUGGCCCA
GAUCUUCGACCACAAGUGCAUAUAGUAGUCAUCGAGGGUCGCCUUUUUUUUUUUUUUUUUUUUUUUGGCCCAGUU
CUGAGACUUCGCUAGAGACUACAGUUACAGCUGCAGUAGUAACCACUGCGGCUAUUGCAGGAAAUCCCGUUCAGG
UUUUUUUUUUUUUUUUUUUCCGCUCACUAUGAUUAAGAACCAGGUGGAGUGUCACUGCUCUCGAGGUCUCACG
AGAGCGCUCGAUACAGUCCUUGGAAGAAUCUUUUUUUUUUUUUUUUUUUUGUGCGACGAUCACAGAGAACUUC
UAUUCAUGCAGGUCUGCUCUAG

Fig. 4

A
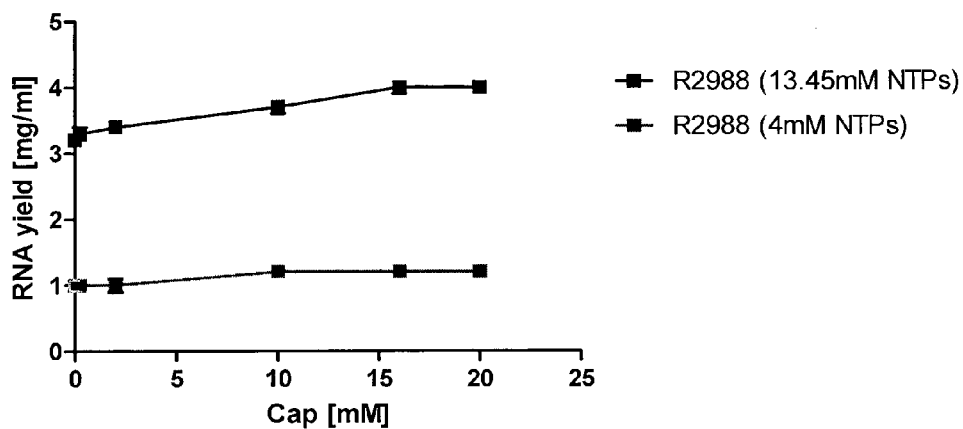
B
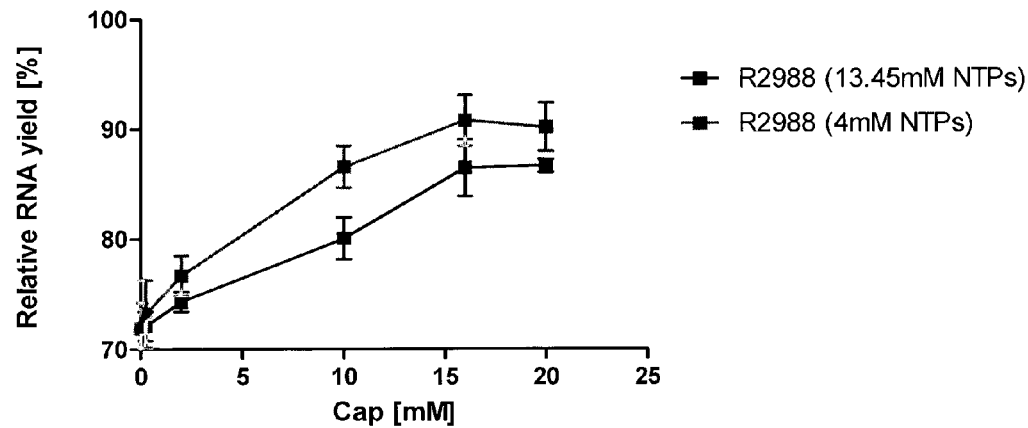
Fig. 13

A
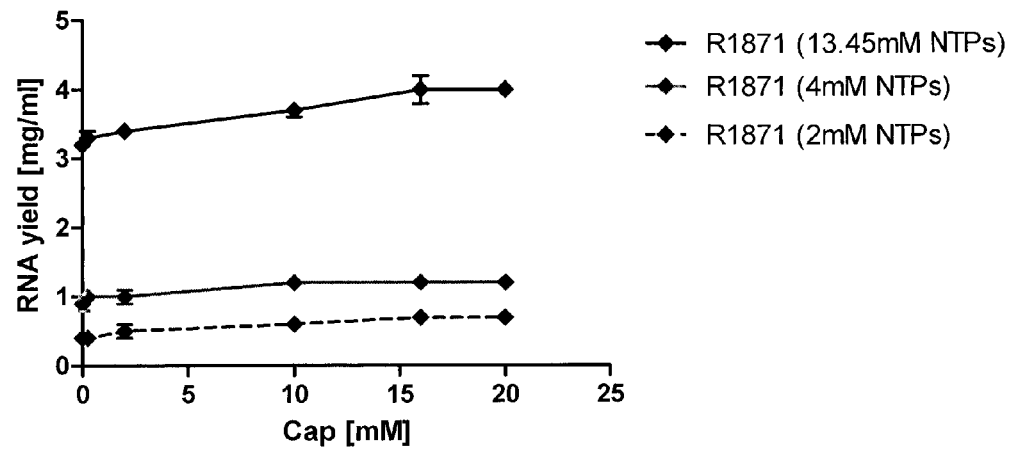
B
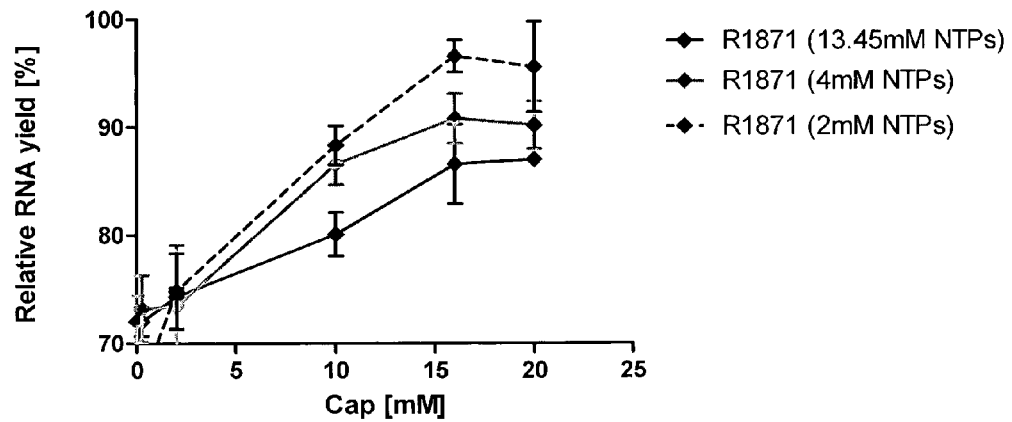
Fig. 14

A
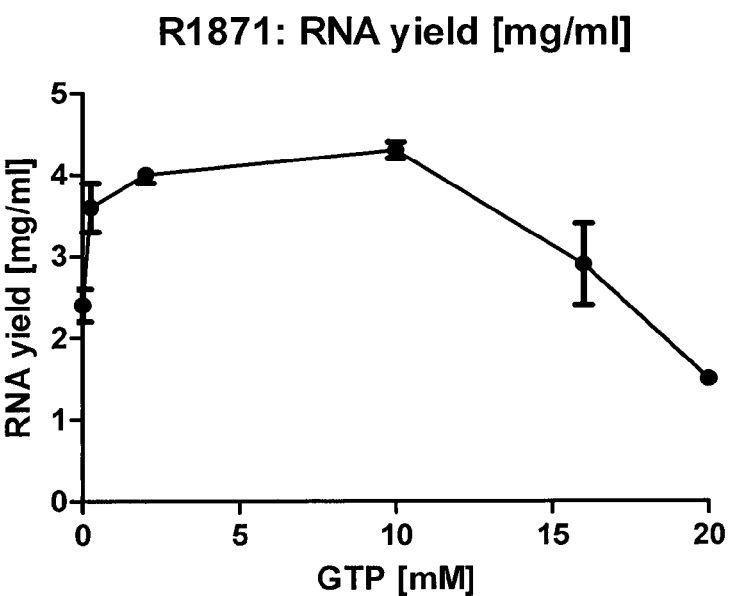
B
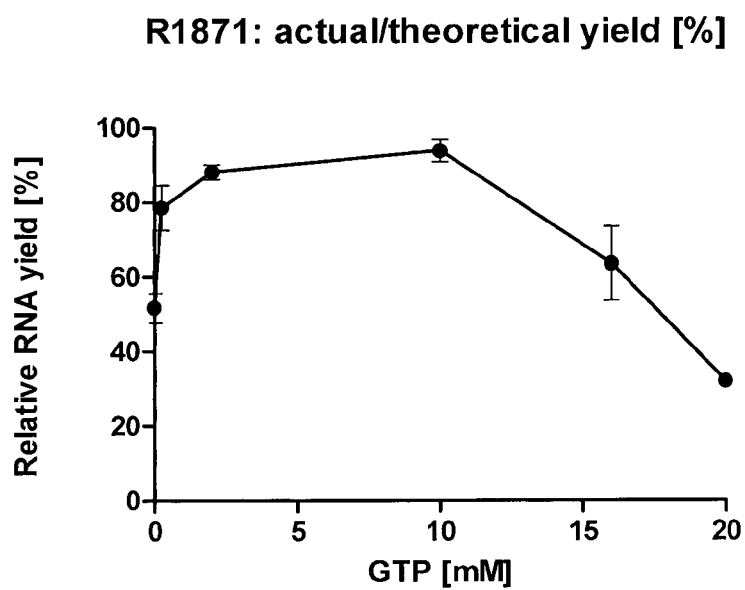
Fig. 15

A
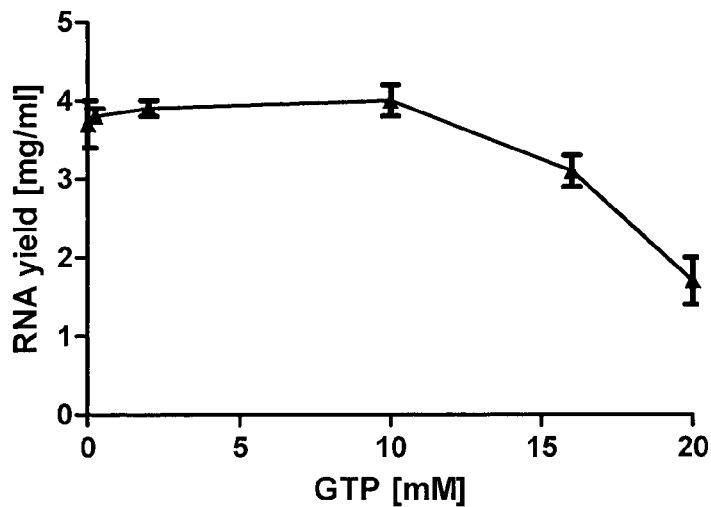
B
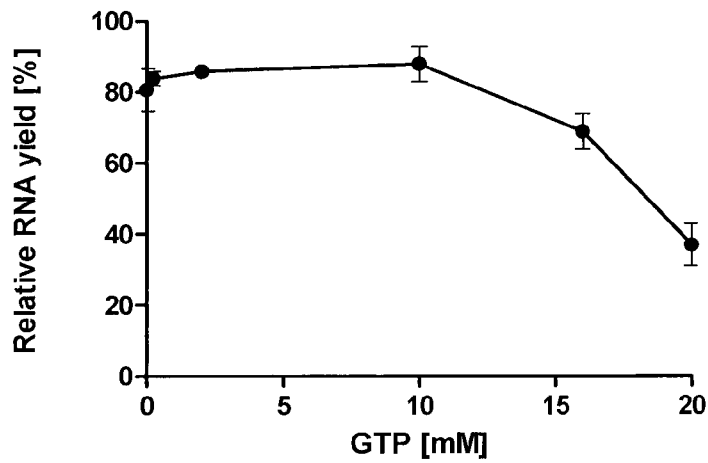
Fig. 16

A
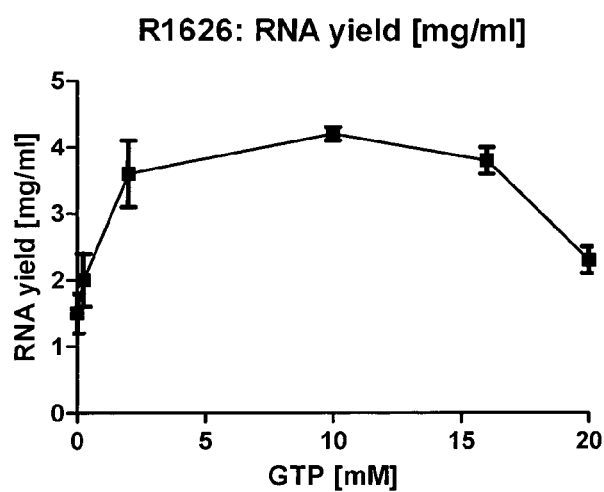
B
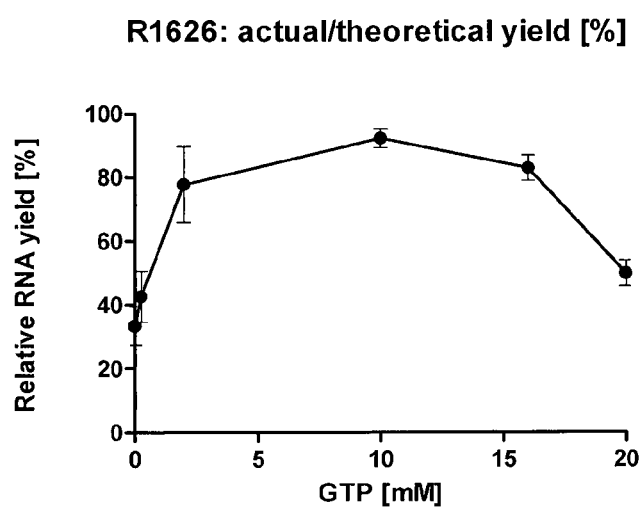
Fig. 17

SEQ ID NO. 6:

GGGGCGCUGCCUACGGAGGUGGCAGCCAUCUCCUUCUCGGCAUCAAGCUUACC<u>A</u>UGAAGG
CCAUCCUGGUGGUCCUCCUGUACACCUUCGCCACCGCGAACGCCGACACGCUGUGCAUCG
GCUACCACGCCAACAACAGCACCGACACCGUGGACACCGUGCUCGAGAAGAACGUCACGG
UGACCCACUCCGUGAACCUGCUGGAGGACAAGCACAACGGGAAGCUCUGCAAGCUGCGGG
GCGUCGCCCCGCUGCACCUCGGGAAGUGCAACAUCGCCGGCUGGAUCCUGGGGAACCCGG
AGUGCGAGAGCCUGUCCACCGCGAGCUCCUGGAGCUACAUCGUGGAGACCUCCAGCUCCG
ACAACGGCACGUGCUACCCCGGCGACUUCAUCGACUACGAGGAGCUCCGCGAGCAGCUGA
GCUCCGUGAGCUCCUUCGAGCGGUUCGAGAUCUUCCCCAAGACCAGCUCCUGGCCCAACC
ACGACAGCAACAAGGGGGUCACCGCCGCCUGCCCGCACGCCGGCGCGAAGUCCUUCUACA
GAACCUGAUCUGGCUCGUGAAGAAGGGGAACAGCUACCCCAAGCUGUCCAAGAGCUACA
UCAACGACAAGGGCAAGGAGGUGCUGGUCCUCUGGGGGAUCCACCACCCCAGCACCUCCG
CCGACCAGCAGAGCCUGUACCAGAACGCCGACGCCUACGUGUUCGUGGGCUCCAGCCGCU
ACUCCAAGAAGUUCAAGCCCGAGAUCGCCAUCCGGCCGAAGGUCCGCGACCAGGAGGGCC
GGAUGAACUACUACUGGACGCUGGUGGAGCCCGGGGACAAGAUCACCUUCGAGGCGACCG
GCAACCUCGUGGUCCCCCGCUACGCCUUCGCCAUGGAGCGGAACGCCGGGAGCGGCAUCA
UCAUCUCCGACACCCCCGUGCACGACUGCAACACGACCUGCCAGACCCCGAAGGGCGCCA
UCAACACCAGCCUGCCCUUCCAGAACAUCCACCCCAUCACGAUCGGGAAGUGCCCCAAGU
ACGUGAAGUCCACCAAGCUGCGCCUCGCGACCGGCCUGCGGAACGUCCCGAGCAUCCAGU
CCCGCGGGCUGUUCGGCGCCAUCGCCGGGUUCAUCGAGGGCGGCUGGACCGGGAUGGUGG
ACGGCUGGUACGGGUACCACCACCAGAACGAGCAGGGCAGCGGGUACGCCGCCGACCUCA
AGUCCACGCAGAACGCGAUCGACGAGAUCACCAACAAGGUGAACAGCGUCAUCGAGAAGA
UGAACACCCAGUUCACCGCCGUGGGCAAGGAGUUCAACCACCUGGAGAAGCGGAUCGAGA
ACCUGAACAAGAAGGUCGACGACGGCUUCCUCGACAUCUGGACGUACAACGCCGAGCUGC
UGGUGCUCCUGGAGAACGAGCGCACCCUGGACUACCACGACUCCAACGUGAAGAACCUCU
ACGAGAAGGUCCGGAGCCAGCUGAAGAACAACGCCAAGGAGAUCGGGAACGGCUGCUUCG
AGUUCUACCACAAGUGCGACAACACCUGCAUGGAGUCCGUGAAGAACGGGACCUACGACU
ACCCCAAGUACAGCGAGGAGGCCAAGCUGAACCGCGAGGAGAUCGACGGCGUGAAGCUCG
AGUCCACGCGGAUCUACCAGAUCCUGGCGAUCUACAGCACCGUCGCCAGCUCCCUGGUGC
UCGUGGUCAGCCUGGGGGCCAUCUCCUUCUGGAUGUGCAGCAACGGCUCCCUGCAGUGCC
GCAUCUGCAUCUGACCACUAGUGCAUCACAUUUAAAAGCAUCUCAGCCUACCAUGAGAAU
AAGAGAAAGAAAAUGAAGAUCAAUAGCUUAUUCAUCUCUUUUUCUUUUUCGUUGGUGUAA
AGCCAACACCCUGUCUAAAAAACAUAAAUUUCUUUAAUCAUUUUGCCUCUUUUCUCUGUG
CUUCAAUUAAUAAAAAUGGAAAGAACCUAGAUCUAAAAAAAAAAAAAAAAAAAAAAAAAA
AAAAAAAAAAAAAAAAAAAAAAAAAAAAAAAAAAAAAAUGCAUCCCCCCCCCCCCCCC
CCCCCCCCCCCCCCCAAAGGCUCUUUUCAGAGCCACCAGAAUU

Fig. 20

METHODS AND MEANS FOR ENHANCING RNA PRODUCTION

This application is a national phase application under 35 U.S.C. § 371 of International Application No. PCT/EP2015/001164, filed Jun. 10, 2015, which claims benefit of International Application No. PCT/EP2014/001577, filed Jun. 10, 2014, the entire contents of each of which are hereby incorporated by reference.

The present invention relates inter alia to a method for synthesizing an RNA molecule of a given sequence, as well as to reactors for performing said method.

Therapeutic ribonucleic acid (RNA) molecules represent an emerging class of drugs. RNA-based therapeutics include mRNA molecules encoding antigens for use as vaccines (Fotin-Mleczek et al. 2012. J. Gene Med. 14(6):428-439). In addition, it is envisioned to use RNA molecules for replacement therapies, e.g. providing missing proteins such as growth factors or enzymes to patients (Karikó et al., 2012. Mol. Ther. 20(5):948-953; Kormann et al., 2012. Nat. Biotechnol. 29(2):154-157). Furthermore, the therapeutic use of noncoding immunostimulatory RNA molecules (WO2009/095226) and other noncoding RNAs such as microRNAs and long noncoding RNAs is considered (Esteller, 2011. Nat. Rev. Genet. 12(12):861-74).

Successful protein expression from transfected RNA depends on transfection efficiency, RNA stability and translation efficiency. The 5' cap structure and the 3' poly(A) tail are important features for the efficient translation of mRNA and protein synthesis in eukaryotic cells. Newly synthesized mRNAs are modified with a cap structure when the transcript reaches a length of 20 to 30 nucleotides. First, the 5' terminal nucleotide pppN is converted to 5' GpppN by a bi-functional capping enzyme containing both RNA 5'-triphosphatase and guanylyltransferase activities. Then the GpppN part is methylated by a second enzyme with (guanine-7)-methyltransferase activity to form the monomethylated m7GpppN type 0 cap structure. The type 0 cap is then converted to an m7GpppN type 1 structure in the nucleus by 2'-O-methylation (Tcherepanova et al., 2008. BMC Mol. Biol. 9:90).

Short RNA molecules can be synthesized by chemical methods whereas long RNAs are typically produced by in vitro transcription reactions containing a suitable DNA template with a bacteriophage-derived promoter, an RNA polymerase, for example bacteriophage SP6, T3 or T7 RNA polymerase and ribonucleoside triphosphates (NTPs). Principally, 5' cap structures can be introduced by two protocols into in vitro transcribed RNA.

In the first protocol, capping occurs concurrently with the initiation of transcription (co-transcriptional capping). In this approach, a dinucleotide cap analog such as m7G(5')ppp(5')G (m7G) is to be added to the reaction mixture. The DNA template is usually designed in such a way that the first nucleotide transcribed is a guanosine. The cap analog directly competes with GTP for incorporation as initial nucleotide (start nucleotide), and is incorporated as readily as any other nucleotide (WO2006/004648). To favor the incorporation of the cap analog, a molar excess of the cap analog over GTP is typically used (e.g. at a 4:1 ratio) and the GTP concentration is reduced compared to the other ribonucleoside triphosphates ATP, CTP and UTP. Under these conditions GTP usually becomes the limiting factor for the synthesis of RNA molecules. Consequently, a high proportion of the other NTPs (usually between 40 to 70%) are not used for RNA synthesis but wasted. With this approach, the RNA yield is typically limited to about 1 mg/ml (WO2006/004648).

In the second protocol, capping is done in a separate enzymatic reaction after in vitro transcription (post-transcriptional or enzymatic capping). Vaccinia Virus Capping Enzyme (VCE) possesses all three enzymatic activities necessary to synthesize a m7G cap structure (RNA 5'-triphosphatase, guanylyltransferase, and guanine-7-methyltransferase). Using GTP as substrate the VCE reaction yields RNA caps in the correct orientation. In addition, a type 1 cap can be created by adding a second Vaccinia enzyme, 2' O methyltransferase, to the capping reaction (Tcherepanova et al., 2008. BMC Mol. Biol. 9:90).

It has been reported that RNA transcribed in vitro by phage polymerases can contain multiple contaminants, including double-stranded RNA molecules generated by self-complementary 3' extension and short RNA molecules produced by abortive transcription initiation events.

RNA molecules synthesized by T7 RNA polymerase during run-off transcription of linearized DNA templates can be longer than the coded RNA (Triana-Alonso et al., 1995, JBC; 270(11): 6298-6307). After leaving the DNA template, the RNA polymerase can bind a transcript to the template site and the 3'-end of the transcript to the product site and extend it, if the 3'-end is not part of a stable secondary structure (self-complementary 3' extension). This effect seems to be especially sensitive to the UTP concentration and a reduction exclusively of the UTP concentration leads to faithful transcription. However, lowering the UTP concentration can also affect the RNA yield. Especially if RNA contains a poly(A) tail, as is common in RNAs such as mRNAs, an excess of unincorporated UTP in the transcription reaction can result in RNA-template dependent incorporation of uridine nucleotides opposite of the poly-A-sequence, resulting in double-stranded RNA molecules which can activate the innate immune response and decrease protein synthesis (Kariko et al., 2011, Nucleic Acids Res.; 39(21): e142).

In addition to the desired full-length RNA molecule, in vitro transcription reactions can also yield smaller oligoribonucleotides which are the result of abortive transcription initiation events (Milligan, et al., 1987. Nucleic Acid Res. 15(21): 8783-8798). These abortive (premature) transcripts are short RNA molecules prematurely released from the ternary complex consisting of RNA polymerase, DNA template, and nascent RNA chain. Typically, most abortive transcripts are two to eight nucleotides in length and are formed due to abortive cycling during initiation. Interestingly, an increase in abortive transcription was observed when NTP concentrations are lower than approximately 2 mM (Kern et al., 1999. Biotechnol. Prog. 15, 174-184). Abortive transcripts are undesirable because their synthesis consumes valuable NTPs and reduces the yield of full-length product.

For the successful development of RNA therapeutics the production of RNA molecules as active pharmaceutical ingredients must be efficient in terms of yield, quality, safety and costs, especially when RNA is produced at a large scale and full-length or full-length capped RNA molecules are required. Several approaches were described for increasing the production of RNA molecules by in vitro transcription. The use of high NTP concentrations is expected to increase the yield of RNA molecules. Alternatively, for the efficient synthesis of capped RNA molecules the adjustment of the ratio of the cap analog to GTP has been suggested.

Standard nucleotide concentrations for in vitro transcription reactions typically range from 1.5 to 16 mM (Milligan, et al., 1987. Nucleic Acid Res. 15(21): 8783-8798; Sampson & Uhlenbeck, 1988. Proc. Natl. Acad. Sci. USA 85(4):1033-7; Cunningham & Ofengand 1990. Biotechniques 9(6):713-4; Weitzmann et al. 1990, Nucleic Acids Res. 18(12):3515-20; Gurevich et al., 1991. Anal. Biochem. 195(2):207-13). NTP concentrations up to 40 mM have been reported to be possible if $Mg^{++}$ concentrations are adjusted accordingly, resulting in increased RNA yield (U.S. Pat. No. 5,256,555).

Several high yield transcription kits are commercially available, e.g. T7 High Yield RNA synthesis kit (New England Biolabs, Ipswich, Mass., USA), TranscriptAid™ T7 High Yield Transcription kit (Thermo Scientific, Waltham, Mass., USA), MEGAscript® High Yield Transcription Kit (Life Technologies, Carlsbad, Calif., USA), or AmpliCap-Max™ T7 High Message Maker kit (Epicentre, Madison, Wis., USA). For all kits, high total NTP working concentrations of 30 to 40 mM are suggested for standard transcription reactions. For the synthesis of capped mRNAs, GTP concentrations range between 1.5 mM and 2 mM GTP.

Although generally high nucleotide concentrations are recommended in order to maximize the RNA yield of in vitro transcription reactions, the use of high NTP concentrations can also have disadvantages. For example, with high initial NTP concentrations and sufficiently high $Mg^{++}$ concentrations (e.g. $Mg(OAc)_2$) high RNA yields can be obtained. However, at these high concentrations a higher fraction of NTPs may be incorporated into short abortive transcripts (Kern et al., 1997. Biotechnol. Prog. 13, 747-756).

To produce capped mRNA co-transcriptionally in the presence of cap analog, economic reasons require lower NTP working concentrations, as cap analog has to be used in excess over GTP and is a major cost factor. Higher cap analog to GTP ratios will lead to a higher proportion of capped RNA but for yield and economic reasons, a 4:1 ratio is usually suggested (New England Biolabs, Capped RNA synthesis (E2040), https://www.neb.com/protocols/1/01/01/capped-rna-synthesis-e2040).

For example, for the transcription of capped RNAs, the manufacturer's instructions for the T7 High Yield RNA synthesis kit suggest using 2 mM GTP with a 4:1 excess of cap analog over GTP. Yields per 20 µl reaction are indicated as 40-50 µg RNA, corresponding to 2-2.5 mg/ml, with approximately 80% capped RNA transcripts (New England Biolabs, Capped RNA synthesis (E2040), https://www.neb.com/protocols/1/01/01/capped-rna-synthesis-e2040).

To compensate for the limited yield resulting from the low GTP concentrations, yields of capped RNA have been increased by supplementing the reaction with the competing nucleotide (GTP, or ATP in case A-cap is used) in such a way that a ratio between 1:1 and 1:50 GTP to cap analog is maintained. With this approach the amount of capped RNA produced per reaction could be doubled (WO2006/004648).

In vitro transcription reactions are typically performed as batch reactions in which all components are combined and then incubated to allow the synthesis of RNA molecules until the reaction terminates. In addition, fed-batch reactions were developed to increase the efficiency of the in vitro transcription reaction (Kern et al., 1997. Biotechnol. Prog. 13, 747-756; Kern et al., 1999. Biotechnol. Prog. 15, 174-184). In a fed-batch system all components are combined, but then additional amounts of some of the reagents are added over time (e.g. NTPs and magnesium) to maintain constant reaction conditions. The fed-batch strategy yielded a 100% improvement in RNA per unit of RNA polymerase or DNA template for a very short 38 base pair DNA template. This method was only used for the synthesis of non-capped RNA molecules with a triphosphate at the 5' terminus.

The use of a bioreactor (transcription reactor) for the synthesis of RNA molecules by in vitro transcription has been reported (WO1995/08626). The bioreactor is configured such that reactants are delivered via a feed line to the reactor core and RNA products are removed by passing through an ultrafiltration membrane (having a nominal molecular weight cut-off, e.g., 100,000 daltons) to the exit stream.

In summary, the yield of capped RNA molecules from in vitro transcription reactions mainly dependents on two factors, the total NTP concentration available for incorporation into the RNA molecule and the cap analog:GTP ratio. For co-transcriptional capping, GTP concentrations are usually reduced compared to the other NTPs. This fact limits the possible transcription yield, especially for templates with high GC-content.

In view of the above, there is a continued need for improved and economical means and methods of RNA production, especially for the production of full-length capped RNA molecules that can be translated into proteins.

SUMMARY OF THE INVENTION

The present invention relates inter alia to a method for synthesizing an RNA molecule of a given sequence, comprising the following steps:
a) determining the fraction (1) for each of the four nucleotides G, A, C and U in said RNA molecule, and
b) synthesizing said RNA molecule by in vitro transcription in a sequence-optimized reaction mix, wherein said sequence-optimized reaction mix comprises the four ribonucleotides GTP, ATP, CTP and UTP, wherein the fraction (2) of each of the four ribonucleotides in the sequence-optimized reaction mix corresponds to the fraction (1) of the respective nucleotide in said RNA molecule, a buffer, a DNA template, and an RNA polymerase.

The present invention also relates to a bioreactor for synthesizing RNA molecules of a given sequence, the bioreactor having a reaction module for carrying out in vitro RNA transcription reactions in a sequence-optimized reaction mix, a capture module for temporarily capturing the transcribed RNA molecules, and a control module for controlling the infeed of components of the sequence-optimized reaction mix into the reaction module, wherein the reaction module comprises a filtration membrane for separating nucleotides from the sequence-optimized reaction mix, and the control of the infeed of components of the sequence-optimized reaction mix by the control module is based on a measured concentration of separated nucleotides.

DEFINITIONS

For the sake of clarity and readability the following definitions are provided. Any technical feature mentioned for these definitions may be read on each and every embodiment of the invention. Additional definitions and explanations may be specifically provided in the context of these embodiments as discussed and explained further below.

5'-Cap structure: A 5' cap is typically a modified nucleotide, particularly a guanine nucleotide, added to the 5' end of an RNA molecule. Preferably, the 5' cap is added using a 5'-5'-triphosphate linkage. A 5' cap may be methylated, e.g.

m7GpppN, wherein N is the terminal 5' nucleotide of the nucleic acid carrying the 5' cap, typically the 5'-end of an RNA. The naturally occurring 5' cap is m7GpppN.

Further examples of 5'cap structures include glyceryl, inverted deoxy abasic residue (moiety), 4',5' methylene nucleotide, 1-(beta-D-erythrofuranosyl) nucleotide, 4'-thio nucleotide, carbocyclic nucleotide, 1,5-anhydrohexitol nucleotide, L-nucleotides, alpha-nucleotide, modified base nucleotide, threo-pentofuranosyl nucleotide, acyclic 3',4'-seco nucleotide, acyclic 3,4-dihydroxybutyl nucleotide, acyclic 3,5 dihydroxypentyl nucleotide, 3'-3'-inverted nucleotide moiety, 3'-3'-inverted abasic moiety, 3'-2'-inverted nucleotide moiety, 3'-2'-inverted abasic moiety, 1,4-butanediol phosphate, 3'-phosphoramidate, hexylphosphate, aminohexyl phosphate, 3'-phosphate, 3'phosphorothioate, phosphorodithioate, or bridging or non-bridging methylphosphonate moiety.

Particularly preferred 5' cap structures are CAP1 (methylation of the ribose of the adjacent nucleotide of m7G), CAP2 (methylation of the ribose of the $2^{nd}$ nucleotide downstream of the m7G), CAP3 (methylation of the ribose of the $3^{rd}$ nucleotide downstream of the m7G), CAP4 (methylation of the ribose of the $4^{th}$ nucleotide downstream of the m7G), A 5' cap structure may be formed by a cap analog.

Cap analog: A cap analog refers to a non-extendable di-nucleotide that has cap functionality which means that it facilitates translation or localization, and/or prevents degradation of the RNA molecule when incorporated at the 5' end of the RNA molecule. Non-extendable means that the cap analog will be incorporated only at the 5'terminus because it does not have a 5' triphosphate and therefore cannot be extended in the 3' direction by a template-dependent RNA polymerase.

Cap analogs include, but are not limited to, a chemical structure selected from the group consisting of m7GpppG, m7GpppA, m7GpppC; unmethylated cap analogs (e.g., GpppG); dimethylated cap analog (e.g., m2,7GpppG), trimethylated cap analog (e.g., m2,2,7GpppG), dimethylated symmetrical cap analogs (e.g., m7Gpppm7G), or anti reverse cap analogs (e.g., ARCA; m7,2'OmeGpppG, m7,2'dGpppG, m7,3'OmeGpppG, m7,3'dGpppG and their tetraphosphate derivatives) (Stepinski et al., 2001. RNA 7(10):1486-95). Examples of cap analogs are shown in Table 1.

TABLE 1

Cap analogs (D1 and D2 denote counterpart diastereoisomers)

| Triphosphate cap analog | Tetraphosphate cap analog |
|---|---|
| $m^7Gp_3G$ | $m^7Gp_4G$ |
| $m_2^{7,3'-O}Gp_3G$ | $b^7Gp_4G$ |
| $b^7Gp_3G$ | $b^7m^{3'-O}Gp_4G$ |
| $e^7Gp_3G$ | $m_2^{2,7}Gp_4G$ |
| $m_2^{2,7}Gp_3G$ | $m_3^{2,2,7}Gp_4G$ |
| $m_3^{2,2,7}Gp_3G$ | $b^7m^2Gp_4G$ |
| $m^7Gp_32'dG$ | $m7Gp^4m^7G$ |
| $m^7Gp_3m^{2'-O}G$ | |
| $m^7Gp_3m^7G$ | |
| $m_2^{7,2'-O}Gp_3G$ | |
| $m_2^{7,2'-O}GpppsG$ (D1) | |
| $m_2^{7,2'-O}GpppsG$ (D2) | |
| $m_2^{7,2'-O}GppspG$ (D1) | |
| $m_2^{7,2'-O}GppspG$ (D2) | |
| $m_2^{7,2'-O}GpsppG$ (D1) | |
| $m_2^{7,2'-O}GpsppG$ (D2) | |

Further cap analogs have been described previously (U.S. Pat. No. 7,074,596, WO2008/016473, WO2008/157688, WO2009/149253, WO2011/015347, and WO2013/059475). The synthesis of $N^7$-(4-chlorophenoxyethyl) substituted dinucleotide cap analogs has been described recently (Kore et al., 2013. Bioorg. Med. Chem. 21(15):4570-4).

Particularly preferred cap analogs are G[5']ppp[5']G, m7G[5']ppp[5']G, $m_3^{2,2,7}$G[5']ppp[5']G, $m_2^{7,3'-O}$G[5']ppp[5']G (3'-ARCA), $m_2^{7,2'-O}$GpppG (2'-ARCA), $m_2^{7,2'-O}$GppspG D1 (β-S-ARCA D1) and $m_2^{7,2'-O}$GppspG D2 (β-S-ARCA D2).

Nucleic acid: The term nucleic acid means any DNA- or RNA-molecule and is used synonymously with polynucleotide. Furthermore, modifications or derivatives of the nucleic acid as defined herein are explicitly included in the general term "nucleic acid". For example, peptide nucleic acid (PNA) is also included in the term "nucleic acid".

Monocistronic RNA: A monocistronic RNA may typically be an RNA, preferably an mRNA, that comprises only one open reading frame. An open reading frame in this context is a sequence of several nucleotide triplets (codons) that can be translated into a peptide or protein.

Bi-/multicistronic RNA: RNA, preferably mRNA, that typically may have two (bicistronic) or more (multicistronic) open reading frames (ORF). An open reading frame in this context is a sequence of several nucleotide triplets (codons) that can be translated into a peptide or protein.

Immunostimulatory RNA: An immunostimulatory RNA (isRNA) in the context of the invention may typically be a RNA that is able to induce an innate immune response. An isRNA usually does not have an open reading frame and thus does not provide a peptide-antigen but elicits an innate immune response, e.g. by binding to pathogen-associated molecular patterns (PAMP) receptors (e.g. Toll-like-receptor (TLR) or other intracellular RNA sensors (e.g. RIG-I, MDA-5 or PKR).

Nucleotide analogs: Nucleotide analogs are nucleotides structurally similar (analog) to naturally occurring nucleotides which include phosphate backbone modifications, sugar modifications, or modifications of the nucleobase.

Nucleic acid synthesis: Nucleic acid molecules used according to the invention as defined herein may be prepared using any method known in the art, including synthetic methods such as e.g. solid phase synthesis, in vivo propagation (e.g. in vivo propagation of viruses), as well as in vitro methods, such as in vitro transcription reactions.

According to the invention the RNA molecule is prepared by in vitro transcription of a corresponding DNA molecule. This DNA template preferably comprises a suitable promoter, e.g. a T7 or SP6 promoter, for in vitro transcription, which is followed by the desired nucleotide sequence coding for the RNA molecule to be prepared and a termination signal for in vitro transcription. The DNA molecule, which forms the template of the at least one RNA of interest, may be prepared by fermentative proliferation and subsequent isolation as part of a plasmid which can be replicated in bacteria. Plasmids which may be mentioned as suitable for the present invention are e.g. the plasmids pUC18, pUC19, pBR322, pT7 Ts (GenBank accession number U26404; Lai et al., Development 1995, 121: 2349 to 2360), pGEM® series, e.g. pGEM®-1 (GenBank accession number X65300; from Promega) and pSP64 (GenBank accession number X65327); cf. also Mezei and Storts, Purification of PCR Products, in: Griffin and Griffin (ed.), PCR Technology: Current Innovation, CRC Press, Boca Raton, Fla., 2001.

RNA: RNA is the usual abbreviation for ribonucleic acid. It is a nucleic acid molecule, i.e. a polymer consisting of nucleotides. These nucleotides are usually adenosine-monophosphate, uridine-monophosphate, guanosine-monophosphate and cytidine-monophosphate monomers which are connected to each other along a so-called backbone. The backbone is formed by phosphodiester bonds between the sugar, i.e. ribose, of a first and a phosphate moiety of a second, adjacent monomer. The specific succession of the monomers is called the RNA-sequence.

Messenger RNA (mRNA): In eukaryotic cells, transcription is typically performed inside the nucleus or the mitochondria. In vivo, transcription of DNA usually results in the so-called premature RNA which has to be processed into so-called messenger RNA, usually abbreviated as mRNA. Processing of the premature RNA, e.g. in eukaryotic organisms, comprises a variety of different posttranscriptional modifications such as splicing, 5'-capping, polyadenylation, export from the nucleus or the mitochondria and the like. The sum of these processes is also called maturation of mRNA. The mature messenger RNA usually provides the nucleotide sequence that may be translated into an amino acid sequence of a particular peptide or protein. Typically, a mature mRNA comprises a 5' cap, a 5'UTR, an open reading frame, a 3'UTR and a poly(A) sequence. In the context of the present invention, an mRNA may also be an artificial molecule, i.e. a molecule not occurring in nature. This means that the mRNA in the context of the present invention may, e.g., comprise a combination of a 5'UTR, open reading frame, 3'UTR and poly(A) sequence, which does not occur in this combination in nature.

Self-replicating RNA (Replicons): Self-replicating RNA are delivery vectors based on alphaviruses which have been developed from Semliki Forest virus (SFV), Sindbis (SIN) virus, and Venezuelan equine encephalitis (VEE) virus. Alphaviruses are single stranded RNA viruses in which heterologous genes of interest may substitute for the alphavirus' structural genes. By providing the structural genes in trans, the replicon RNA is packaged into replicon particles (RP) which may be used for gene therapy purposes or genetic vaccination (see for example Vander Veen et al., 2012. Alphavirus replicon vaccines. Animal Health Research Reviews, p. 1-9). After entry into the host cell, the genomic viral RNA initially serves as an mRNA for translation of the viral nonstructural proteins (nsPs) required for initiation of viral RNA amplification. RNA replication occurs via synthesis of a full-length minus-strand intermediate that is used as the template for synthesis of additional genome-length RNAs and for transcription of a plus-strand subgenomic RNA from an internal promoter. Such RNA may then be considered as self-replicating RNA, since the non-structural proteins responsible for replication (and transcription of the heterologous genes) are still present in such replicon. Such alphavirus vectors are referred to as "replicons."

Sequence of a nucleic acid molecule: The sequence of a nucleic acid molecule is typically understood to be the particular and individual order, i.e. the succession of its nucleotides.

Open reading frame: An open reading frame (ORF) in the context of the invention may typically be a sequence of several nucleotide triplets which may be translated into a peptide or protein. An open reading frame preferably contains a start codon, i.e. a combination of three subsequent nucleotides coding usually for the amino acid methionine (ATG or AUG), at its 5'-end and a subsequent region which usually exhibits a length which is a multiple of 3 nucleotides. An ORF is preferably terminated by a stop codon (e.g., TAA, TAG, TGA). Typically, this is the only stop codon of the open reading frame. Thus, an open reading frame in the context of the present invention is preferably a nucleotide sequence, consisting of a number of nucleotides that may be divided by three, which starts with a start codon (e.g. ATG or AUG) and which preferably terminates with a stop codon (e.g., TAA, TGA, or TAG or UAA, UAG, UGA, respectively). The open reading frame may be isolated or it may be incorporated in a longer nucleic acid sequence, for example in a vector or an mRNA. An open reading frame may also be termed "protein coding region" or "coding region".

Sequence-optimized reaction mix: A reaction mix for use in an in vitro transcription reaction of an RNA molecule of a given sequence comprising the four nucleoside triphosphates (NTPs) GTP, ATP, CTP and UTP, wherein the fraction (2) of each of the four nucleoside triphosphates (NTPs) in the sequence-optimized reaction mix corresponds to the fraction (1) of the respective nucleotide in said RNA molecule, a buffer, a DNA template, and an RNA polymerase. If a ribonucleotide is not present in said RNA molecule, the corresponding nucleoside triphosphate is also not present in the sequence-optimized reaction mix.

Sequence-optimized nucleoside triphosphate (NTP) mix: A mixture of nucleoside triphosphates (NTPs) for use in an in vitro transcription reaction of an RNA molecule of a given sequence comprising the four nucleoside triphosphates (NTPs) GTP, ATP, CTP and UTP, wherein the fraction (2) of each of the four nucleoside triphosphates (NTPs) in the sequence-optimized nucleoside triphosphate (NTP) mix corresponds to the fraction (1) of the respective nucleotide in said RNA molecule. If a ribonucleotide is not present in the RNA molecule, the corresponding nucleoside triphosphate is also not present in the sequence-optimized nucleoside triphosphate (NTP) mix.

Modified nucleoside triphosphate: The term "modified nucleoside triphosphate" as used herein refers to chemical modifications comprising backbone modifications as well as sugar modifications or base modifications. These modified nucleoside triphosphates are also termed herein as (nucleotide) analogs.

In this context, the modified nucleoside triphosphates as defined herein are nucleotide analogs/modifications, e.g. backbone modifications, sugar modifications or base modifications. A backbone modification in connection with the present invention is a modification, in which phosphates of the backbone of the nucleotides are chemically modified. A sugar modification in connection with the present invention is a chemical modification of the sugar of the nucleotides. Furthermore, a base modification in connection with the present invention is a chemical modification of the base moiety of the nucleotides. In this context nucleotide analogs or modifications are preferably selected from nucleotide analogs which are applicable for transcription and/or translation.

Sugar Modifications

The modified nucleosides and nucleotides, which may be used in the context of the present invention, can be modified in the sugar moiety. For example, the 2' hydroxyl group (OH) can be modified or replaced with a number of different "oxy" or "deoxy" substituents. Examples of "oxy"-2' hydroxyl group modifications include, but are not limited to, alkoxy or aryloxy (—OR, e.g., R=H, alkyl, cycloalkyl, aryl, aralkyl, heteroaryl or sugar); polyethyleneglycols (PEG), —O(CH$_2$CH$_2$O)nCH$_2$CH$_2$OR; "locked" nucleic acids (LNA) in which the 2' hydroxyl is connected, e.g., by a methylene bridge, to the 4' carbon of the same ribose sugar; and amino groups (—O-amino, wherein the amino group, e.g., NRR, can be alkylamino, dialkylamino, heterocyclyl, arylamino, diarylamino, heteroarylamino, or diheteroaryl amino, ethylene diamine, polyamino) or aminoalkoxy.

"Deoxy" modifications include hydrogen, amino (e.g. $NH_2$; alkylamino, dialkylamino, heterocyclyl, arylamino, diaryl amino, heteroaryl amino, diheteroaryl amino, or amino acid); or the amino group can be attached to the sugar through a linker, wherein the linker comprises one or more of the atoms C, N, and O.

The sugar group can also contain one or more carbons that possess the opposite stereochemical configuration than that of the corresponding carbon in ribose. Thus, a modified nucleotide can include nucleotides containing, for instance, arabinose as the sugar.

Backbone Modifications

The phosphate backbone may further be modified in the modified nucleosides and nucleotides. The phosphate groups of the backbone can be modified by replacing one or more of the oxygen atoms with a different substituent. Further, the modified nucleosides and nucleotides can include the full replacement of an unmodified phosphate moiety with a modified phosphate as described herein. Examples of modified phosphate groups include, but are not limited to, phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. The phosphate linker can also be modified by the replacement of a linking oxygen with nitrogen (bridged phosphoroamidates), sulfur (bridged phosphorothioates) and carbon (bridged methylene-phosphonates).

Base Modifications

The modified nucleosides and nucleotides, which may be used in the present invention, can further be modified in the nucleobase moiety. Examples of nucleobases found in RNA include, but are not limited to, adenine, guanine, cytosine and uracil. For example, the nucleosides and nucleotides described herein can be chemically modified on the major groove face. In some embodiments, the major groove chemical modifications can include an amino group, a thiol group, an alkyl group, or a halo group.

In particularly preferred embodiments of the present invention, the nucleotide analogs/modifications are selected from base modifications, which are preferably selected from 2-amino-6-chloropurineriboside-5'-triphosphate, 2-Aminopurine-riboside-5'-triphosphate; 2-aminoadenosine-5'-triphosphate, 2'-Amino-2'-deoxycytidine-triphosphate, 2-thiocytidine-5'-triphosphate, 2-thiouridine-5'-triphosphate, 2'-Fluorothymidine-5'-triphosphate, 2'-O-Methyl-inosine-5'-triphosphate 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-Bromo-2'-deoxycytidine-5'-triphosphate, 5-Bromo-2'-deoxyuridine-5'-triphosphate, 5-iodocytidine-5'-triphosphate, 5-Iodo-2'-deoxycytidine-5'-triphosphate, 5-iodouridine-5'-triphosphate, 5-Iodo-2'-deoxyuridine-5'-triphosphate, 5-methylcytidine-5'-triphosphate, 5-methyluridine-5'-triphosphate, 5-Propynyl-2'-deoxycytidine-5'-triphosphate, 5-Propynyl-2'-deoxyuridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, or puromycin-5'-triphosphate, xanthosine-5'-triphosphate. Particular preference is given to nucleotides for base modifications selected from the group of base-modified nucleotides consisting of 5-methylcytidine-5'-triphosphate, 7-deazaguanosine-5'-triphosphate, 5-bromocytidine-5'-triphosphate, and pseudouridine-5'-triphosphate.

In some embodiments, modified nucleosides include pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine.

In some embodiments, modified nucleosides include 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine.

In other embodiments, modified nucleosides include 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine.

In other embodiments, modified nucleosides include inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In some embodiments, the nucleotide can be modified on the major groove face and can include replacing hydrogen on C-5 of uracil with a methyl group or a halo group.

In specific embodiments, a modified nucleoside is 5'-O-(1-Thiophosphate)-Adenosine, 5'-O-(1-Thiophosphate)-Cytidine, 5'-O-(1-Thiophosphate)-Guanosine, 5'-O-(1-Thiophosphate)-Uridine or 5'-O-(1-Thiophosphate)-Pseudouridine.

In further specific embodiments the modified nucleotides include nucleoside modifications selected from 6-aza-cytidine, 2-thio-cytidine, α-thio-cytidine, Pseudo-iso-cytidine, 5-aminoallyl-uridine, 5-iodo-uridine, N1-methyl-pseudouridine, 5,6-dihydrouridine, α-thio-uridine, 4-thio-uridine, 6-aza-uridine, 5-hydroxy-uridine, deoxy-thymidine, 5-methyl-uridine, Pyrrolo-cytidine, inosine, α-thio-guanosine, 6-methyl-guanosine, 5-methyl-cytidine, 8-oxo-guanosine, 7-deaza-guanosine, N1-methyl-adenosine, 2-amino-6-Chloro-purine, N6-methyl-2-amino-purine, Pseudo-iso-cytidine, 6-Chloro-purine, N6-methyl-adenosine, α-thio-adenosine, 8-azido-adenosine, 7-deaza-adenosine.

Further modified nucleotides have been described previously (WO2013052523).

Yield: Yield, also referred to as a reaction yield, is the amount of product obtained in a chemical or enzymatic reaction. The absolute yield can be given as the weight in grams or in moles (molar yield). The relative yield, fractional yield, or percentage yield, which serve to measure the effectiveness of a synthetic procedure, are calculated by dividing the amount of the obtained product by the theoretical yield (the unit of measure for both must be the same).

relative yield=(actual yield)/(theoretical yield)

Actual yield: The actual yield refers to the amount of the product obtained in a chemical reaction.

Theoretical yield: The theoretical yield is the maximum amount of product that can be produced in a perfectly efficient chemical or enzymatic reaction. In reality, most reactions are not perfectly efficient—the reaction's actual yield is usually less than the theoretical yield. The theoretical yield is calculated based on the molar amount of the limiting reactant, taking into account the stoichiometry of the reaction. For the calculation it is usually assumed that there is only one reaction involved.

RNA yield: The RNA yield is the amount of RNA product obtained in an in vitro transcription reaction. The RNA yield can be expressed as the RNA concentration (g/ml or mol/l). Multiplication of the RNA concentration with the reaction volume gives the absolute amount of RNA (in grams or moles).

Actual RNA yield: The actual RNA yield is the experimentally determined amount of RNA product in an in vitro transcription reaction at a defined time point, e.g. the yield after completion of the reaction. For example, the RNA concentration can be determined via absorbance measurement at 260 nm using a spectrophotometer (Kolitz et al., 2013. Methods Enzymol. 530:331-6). One absorbance unit at 260 nm corresponds to 40 ng/µl of RNA (1 A260=40 ng/µl RNA).

Theoretical RNA yield: The theoretical RNA yield is the maximal possible RNA yield based on the available NTPs in the in vitro transcription reaction. In a standard transcription reaction with equal concentrations of the four NTPs (ATP, GTP, CTP, UTP) typically the nucleotide which corresponds to the most frequent nucleotide in the RNA sequence becomes the limiting factor. In a sequence-optimized transcription reaction using a sequence-optimized NTP mix for the RNA sequence of interest none of the individual nucleotides becomes the limiting factor.

To calculate the theoretical RNA yield for a transcription reaction, the amount of each NTP (in mol) present at the start of the transcription reaction is divided by the number of the respective nucleotide present in the sequence of the RNA molecule resulting in the possible number of RNA molecules which can be synthesized (in mol). Multiplying by the molecular mass of the RNA yields the theoretical RNA yield in mass units (gram). In a standard transcription reaction using equal concentrations of each NTP typically the NTP which corresponds to the most frequent nucleotide in the RNA sequence becomes the limiting factor. By contrast, in a sequence-optimized transcription reaction no NTP will become the limiting factor because all types of NTPs are present at the same ratio as the corresponding nucleotides in sequence of the RNA molecule.

Relative RNA yield: The relative RNA yield, fractional RNA yield, or percentage RNA yield, which serve to measure the efficiency of an in vitro transcription reaction, are calculated by dividing the amount of the obtained RNA product (actual RNA yield) by the theoretical RNA yield (the unit of measure for both must be the same):

relative RNA yield=(actual RNA yield)/(theoretical RNA yield)

To express the efficiency of an in vitro transcription reaction, the percent RNA yield can be calculated:

% RNA yield=(actual RNA yield)/(theoretical RNA yield)×100

DETAILED DESCRIPTION OF THE INVENTION

In a first aspect, the present invention relates to a method for synthesizing an RNA molecule of a given sequence, comprising the following steps:
a) determining the fraction (1) for each of the four nucleotides G, A, C and U in said RNA molecule, and
b) synthesizing said RNA molecule by in vitro transcription in a sequence-optimized reaction mix, wherein said sequence-optimized reaction mix comprises the four ribonucleoside triphosphates (NTPs) GTP, ATP, CTP and UTP, wherein the fraction (2) of each of the four ribonucleoside triphosphates (NTPs) in the reaction mix corresponds to the fraction (1) of the respective nucleotide in said RNA molecule, a buffer, a DNA template, and an RNA polymerase.

In the context of the present invention and as shown in Example 1 and FIGS. 5 and 6, it has been found that the use of a sequence-optimized reaction mix containing the four ribonucleoside triphosphates (NTPs) GTP, ATP, CTP and UTP for the production of an RNA molecule with a given sequence by in vitro transcription results in higher RNA product yield and less unincorporated and therefore wasted NTPs compared to a non-optimized reaction mix with equimolar initial concentrations of all four NTPs. This aspect is especially valuable when difficult to synthesize and therefore expensive modified nucleotides are used. In the sequence-optimized NTP mix GTP, ATP, CTP and UTP are represented at a fraction which corresponds to the fraction of said nucleotides G, A, C and U occurring in said RNA sequence. In sequence-optimized in vitro transcription reactions, it is envisaged that the four NTPs are consumed to the same extent and transcription continues until the NTPs are used up, thus wasting less material.

Furthermore, it is expected, that the abovementioned possibility of the synthesis of RNA molecules which are longer than the coded RNA, for example due to self-complementary 3' extension (Triana-Alonso et al., 1995, JBC; 270(11): 6298-6307), is avoided when using sequence-optimized NTP mixes because no excess UTP remains at the end of the reaction. Especially if RNA contains a poly(A) tail, as is common in RNAs such as mRNAs, an excess of unincorporated UTP in the transcription reaction can result in RNA-template dependent incorporation of uridine nucleotides opposite of the poly-A-sequence, resulting in double-stranded RNA molecules which can activate the innate immune response and decrease protein synthesis (Kariko et al., 2011, Nucleic Acids Res.; 39(21): e142).

As it will be explained in detail below, methods for the production of RNA molecules using in vitro transcription are known in the art. It is also known to use nucleotide analogs to improve for example the stability of the RNA molecule. The present invention concerns the concentration of the ribonucleoside triphosphates (NTPs) in the reaction mix of the in vitro transcription reaction.

Consequently, in a first step of the method of the present invention, the fraction (1) of each of the four nucleotides G, A, C and U in said RNA molecule is determined. This can be performed by any method known in the art, e.g. by simple counting of the number of nucleotides or by using computer-based methods.

The fraction (1) of each of the nucleotides can then be expressed by any suitable term, including number, percentage, mole fraction or molar percent. The mole fraction or molar fraction ($x_i$) is defined as the amount of a constituent (expressed in moles), $n_i$, divided by the total amount of all constituents in a mixture, $n_{tot}$. The sum of all the mole fractions is equal to 1. The same concept expressed with a denominator of 100 is the mole percent or molar percentage (mol %).

Based on the determination of the fraction of each of the nucleotides in said RNA molecule, in a further step of the method of the present invention, said RNA molecule is synthesized by in vitro transcription in a sequence-optimized reaction mix, wherein said sequence-optimized reaction mix comprises the four ribonucleoside triphosphates (NTPs) GTP, ATP, CTP and UTP or analogs thereof, and wherein the fraction (2) of each of the four ribonucleoside triphosphates (NTPs) in the sequence-optimized reaction mix corresponds to the fraction (1) of the respective nucleotide in said RNA molecule.

In a preferred embodiment, step b) of the method of the invention comprises the steps of b1) preparing a sequence-optimized ribonucleoside triphosphate (NTP) mix comprising the four ribonucleoside triphosphates (NTPs) GTP, ATP, CTP and UTP, wherein the fraction (2) of each of the four ribonucleoside triphosphates (NTPs) in the sequence-optimized ribonucleoside triphosphate (NTP) mix corresponds to the fraction (1) of the respective nucleotide in said RNA molecule, and b2) synthesizing said RNA molecule by in vitro transcription in a sequence-optimized reaction mix comprising the sequence-optimized ribonucleoside triphosphate (NTP) mix of step (b1), a buffer, a DNA template, and an RNA polymerase.

Consequently, in this preferred embodiment, a sequence-optimized ribonucleoside triphosphate (NTP) mix is prepared based on the determination of fraction (1), which is then added to the reaction mix. All definitions indicated above with respect to the sequence-optimized reaction mix, and especially those made with respect to the issue "fraction (1) corresponds to fraction (2)" also apply to the sequence-optimized ribonucleoside triphosphate (NTP) mix.

In this context, the person skilled in the art will understand that if said RNA molecule does not contain all nucleotides G, A, C, and U, respectively, the same will also apply to the sequence-optimized ribonucleoside triphosphate (NTP) mix and to the sequence-optimized reaction mix.

According to the invention, "fraction (1) corresponds to fraction (2)" means that the fraction of the ribonucleoside triphosphates (NTPs) in the sequence-optimized NTP mix or in the sequence-optimized reaction mix has been adapted to the fraction of the nucleotides in the RNA molecule. The skilled person will understand that there is no need that fraction (2) exactly mirrors fraction (1), but that it is required that the individual fraction (2) of each ribonucleoside triphosphate in the sequence-optimized NTP mix or in the sequence-optimized reaction mix reflects the fraction (1) of the corresponding nucleotide in said RNA molecule.

For assessing in more detail the relationship between fraction (1) and fraction (2), the following may be considered for the definition of the term "fraction (1) corresponds to fraction (2)":

a) With respect to the fraction of the ribonucleoside triphosphate in the sequence-optimized NTP mix or in the sequence-optimized reaction mix which corresponds to the first nucleotide of the RNA molecule to be synthesized, it is, according to one embodiment of the present invention, possible that fraction (2) is in the range of fraction (1), e.g. that fraction (1) and fraction (2) differ by not more than 25%, 20%, 15%, 10%, 7%, 5% or by a value between 0.1% and 5%.

b) With respect to the other ribonucleoside triphosphates present in the sequence-optimized NTP mix or in the sequence-optimized reaction mix which do not correspond to the first nucleotide of said RNA molecule, fraction (2) is preferably in the range of fraction (1), e.g. fraction (1) and fraction (2) differ by not more than 25%, 20%, 15%, 10%, 7%, 5% or by a value between 0.1% and 5%.

In a preferred embodiment of the invention, a start nucleotide is added to the sequence-optimized NTP mix or to the sequence-optimized reaction mix before the start of the in vitro transcription. A start nucleotide is a nucleotide which corresponds to the first nucleotide of said RNA molecule (+1 position). The start nucleotide may be especially added to increase the initiation rate of the RNA polymerase. Said start nucleotides are also known in the art and include a nucleoside monophosphate, a nucleoside diphosphate, a nucleoside triphosphate. The start nucleotide can be a mononucleotide, a dinucleotide or a trinucleotide. In case that the first nucleotide of said RNA molecule is a G, the start nucleotide is preferably GTP or GMP.

In a preferred embodiment of the invention, said start nucleotide is a dinucleotide. In an even more preferred embodiment the start nucleotide is a cap analog.

In a preferred embodiment, the cap analog is selected from the group consisting of G[5']ppp[5']G, m$^7$G[5']ppp[5']G, m$_2$$^{2,2,3}$G[5']ppp[5']G, m$_2$$^{7,3'-O}$G[5']ppp[5']G (3'-ARCA), m$_2$$^{7,2'-O}$GpppG (2'-ARCA), m$_2$$^{7,2'-O}$GppspG D1 (β-S-ARCA D1) and m$_2$$^{7,2'-O}$GppspG D2 (β-S-ARCA D2).

According to another, preferred embodiment, however, in the sequence-optimized NTP mix or in the sequence-optimized reaction mix, the start nucleotide corresponding to the first nucleotide of said RNA molecule is added in excess compared to the fraction of that nucleotide in said RNA molecule which is found at the first position of said RNA molecule.

Preferably the start nucleotide is added with an initial concentration in the range of about 1 to 20 mM, 1 to 17.5 mM, 1 to 15 mM, 1 to 12.5 mM, 1 to 10 mM, 1 to 7.5 mM, 1 to 5 mM or 1 to 2.5 mM. Even more preferred the start nucleotide is added with an initial concentration of about 5 to 20 mM or 7.5 to 17.5 mM.

In a preferred, exemplary embodiment of the above, the first nucleotide of the RNA molecule is G, the start nucleotide is a cap analog of G and the corresponding ribonucleoside triphosphate is GTP. In this embodiment, the cap analog is present in the reaction mix in an excess, in comparison to GTP. Preferably the cap analog is added with an initial concentration in the range of about 1 to 20 mM, 1 to 17.5 mM, 1 to 15 mM, 1 to 12.5 mM, 1 to 10 mM, 1 to 7.5 mM, 1 to 5 mM or 1 to 2.5 mM. Even more preferred the cap analog is added with an initial concentration of about 5 to 20 mM, 7.5 to 20 mM, 10 to 20 mM or 12.5 to 20 mM.

Methods for in vitro transcription are known in the art (Geall et al., 2013. Semin. Immunol. 25(2): 152-159; Brunelle et al., 2013. Methods Enzymol. 530:101-14). Reagents used in said method typically include:
1) a linearized DNA template with a promoter sequence that has a high binding affinity for its respective RNA polymerase such as bacteriophage-encoded RNA polymerases,
2) ribonucleoside triphosphates (NTPs) for the four bases (adenine, cytosine, guanine and uracil);
3) a cap analog as defined above (e.g. m7G(5')ppp(5')G (m7G));
4) a DNA-dependent RNA polymerase (e.g. T7, T3 or SP6 RNA polymerase);
5) a ribonuclease (RNase) inhibitor to inactivate any contaminating RNase;
6) a pyrophosphatase to degrade pyrophosphate, which may inhibit transcription;
7) $MgCl_2$, which supplies $Mg^{2+}$ as a co-factor for the polymerase;
8) a buffer to maintain a suitable pH value, which can also contain antioxidants and polyamines such as spermidine at optimal concentrations.

According to a preferred embodiment, the sequence-optimized reaction mix used for the inventive method for synthesizing an RNA molecule of a given sequence comprises a buffer selected from the group consisting of 4-(2-hydroxyethyl)-1-piperazineethanesulfonic acid (HEPES) and tris(hydroxymethyl)aminomethane (Tris). Preferably the buffer is used at a concentration from 10 to 100 mM, 10 to 75 mM, 10 to 50 mM, 10 to 40 mM, 10 to 30 mM or 10 to 20 mM. The pH value of the buffer can be adjusted with, for example, NaOH, KOH or HCl. Preferably the buffer has a pH value from 6 to 8.5, from 6.5 to 8.0, from 7.0 to 7.5, even more preferred 7.5. Most preferred is a buffer selected from the group consisting of 80 mM HEPES/KOH, pH 7.5 and 40 mM Tris/HCl, pH 7.5.

According to a preferred embodiment of the invention, the RNA polymerase comprised in the sequence-optimized reaction mix is selected from the group consisting of T3, T7 and SP6 RNA polymerase. Preferably, the concentration of the RNA polymerase is from about 1 to 100 nM, 1 to 90 nM, 1 to 80 nM, 1 to 70 nM, 1 to 60 nM, 1 to 50 nM, 1 to 40 nM, 1 to 30 nM, 1 to 20 nM, or about 1 to 10 nM. Even more preferred, the concentration of the RNA polymerase is from about 10 to 50 nM, 20 to 50 nM, or 30 to 50 nM. Most preferred is a RNA polymerase concentration of about 40 nM. In this context a concentration of 500 to 10000 U/ml of the RNA polymerase is preferred. More preferred is a concentration of 1000 to 7500 U/ml and most preferred is a concentration of 2500 to 5000 Units/ml of the RNA polymerase. The person skilled in the art will understand that the choice of the RNA polymerase concentration is influenced by the concentration of the DNA template.

According to a preferred embodiment of the invention, the concentration of the DNA template comprised in the sequence-optimized reaction mix is in a range from about 1 to 50 nM, 1 to 40 nM, 1 to 30 nM, 1 to 20 nM, or about 1 to 10 nM. Even more preferred the concentration of the DNA template is from about 10 to 30 nM. Most preferred the concentration of the DNA template is about 20 nM. In this context it is particularly preferred to have a concentration of the DNA template of about 1 to 200 µg/ml and more preferably of about 10 to 100 µg/ml, and most preferably of about 20 to 50 µg/ml (e.g. 25 or 50 µg/ml).

According to a preferred embodiment of the invention, the sequence-optimized reaction mix comprises pyrophosphatase. Preferably, the concentration of the pyrophosphatase is from about 1 to 20 units/ml, 1 to 15 units/ml, 1 to 10 units/ml, 1 to 5 units/ml, or 1 to 2.5 units/ml. Even more preferred the concentration of the pyrophosphatase is about 1 unit/ml or is about 5 units/ml.

According to a preferred embodiment of the invention, the sequence-optimized reaction mix comprises $Mg^{++}$ ions. Preferably, the $Mg^{++}$ ions are provided in the form of $MgCl_2$ or $Mg(OAc)_2$. Preferably, the initial free $Mg^{++}$ concentration is from about 1 to 100 mM, 1 to 75 mM, 1 to 50 mM, 1 to 25 mM, or 1 to 10 mM. Even more preferred the initial free $Mg^{++}$ concentration is from about 10 to 30 mM or about 15 to 25 mM. Most preferred is an initial free $Mg^{++}$ concentration of about 24 mM. The person skilled in the art will understand that the choice of the $Mg^{++}$ concentration is influenced by the initial total NTP concentration.

According to a preferred embodiment of the invention, the sequence-optimized reaction mix comprises a reducing agent to keep the RNA polymerase in its active state. Preferably, the reducing agent is selected from the group consisting of dithiothreitol (DTT), dithioerythritol (DTE), Tris(2-carboxyethyl)phosphine (TCEP) and β-mercaptoethanol. Preferably the concentration of the reducing reagent is from about 1 to 50 mM, 1 to 40 mM, 1 to 30 mM, or 1 to 20 mM, or 1 to 10 mM. Even more preferred the concentration of the reducing reagent is from 10 to 50 mM or 20 to 40 mM. Most preferred is a sequence-optimized reaction mix comprising 40 mM of DTT.

According to a preferred embodiment of the invention, the sequence-optimized reaction mix comprises a polyamine. Preferably, the polyamine is selected from the group consisting of spermine and spermidine. Preferably the concentration of the polyamine is from about 1 to 25 mM, 1 to 20 mM, 1 to 15 mM, 1 to 10 mM, 1 to 5 mM, or about 1 to 2.5 mM. Even more preferred the concentration of the polyamine is about 2 mM. Most preferred is a sequence-optimized reaction mix comprising 2 mM of spermidine.

According to a preferred embodiment of the invention, the sequence-optimized reaction mix comprises a ribonuclease inhibitor. Preferably, the concentration of the ribonuclease inhibitor is from about 1 to 500 units/ml, 1 to 400 units/ml, 1 to 300 units/ml, 1 to 200 units/ml, or 1 to 100 units/ml. Even more preferred the concentration of the ribonuclease inhibitor is about 200 units/ml.

According to a preferred embodiment of the invention, the initial total NTP concentration in the sequence-optimized NTP mix or sequence-optimized reaction mix is less than 20 mM, less than 15 mM, less than 10 mM, less than 7.5 mM, less than 5.0 mM or less than 2.5 mM.

According to the invention, the term initial total nucleotide concentration means the total concentration of NTPs, e.g. the sum of the concentrations of ATP, GTP, CTP and/or UTP, present initially in the sequence-optimized NTP mix or sequence-optimized reaction mix when the various components of the sequence-optimized reaction mix have been assembled in the final volume for carrying out the in vitro transcription reaction. Naturally, as the reaction proceeds, the nucleotides will be incorporated into the RNA molecule and consequently the concentration of the total nucleotides will be progressively reduced from its initial value.

An important aspect of the present invention is that the use of a sequence-optimized NTP mix or sequence-optimized reaction mix leads to an increased efficiency of RNA synthesis even at low initial total nucleotide concentrations (e.g. at 2 mM). By contrast, it has previously been suggested that for an increased RNA yield high concentrations of total nucleotides, in the order of 12 mM to 40 mM, are necessary (U.S. Pat. No. 6,586,218).

Furthermore, it is expected that the synthesis of short abortive RNA molecules is decreased when low initial total nucleotide concentrations (e.g. 2.5 mM) in a sequence-optimized NTP mix or sequence-optimized reaction mix are used. By contrast, an increase in abortive transcription was observed when NTP concentrations of a standard equimolar NTP mix were lowered below approximately 2 mM (Kern et al., 1999. Biotechnol. Prog. 15, 174-184).

Another preferred embodiment of the invention relates to the form in which the NTPs are added to the sequence-optimized NTP mix or sequence-optimized reaction mix. The ribonucleoside triphosphates (NTPs) GTP, ATP, CTP and UTP or analogs thereof may be provided with a monovalent or divalent cation as counterion. Preferably the monovalent cation is selected from the group consisting of $Li^+$, $Na^+$, $K^+$, $NH_4^+$ or tris(hydroxymethyl)-aminomethane (Tris). Preferably, the divalent cation is selected from the group consisting of $Mg^{++}$, $Ba^{++}$ and $Mn^{++}$.

According to a most preferred embodiment of the invention, the NTP counter ion is tris(hydroxymethyl)-aminomethane (Tris).

Bacteriophage RNA polymerases are known to be sensitive to salt inhibition. The negative impact of high NaCl concentrations on RNA yields has been described (e.g. Kern & Davis, 1997. Biotechnol. Prog., 13, 747-756; U.S. Pat. No. 6,586,218 B2). High concentrations of Na-NTPs, especially as consequence when pursuing a NTP feeding strategy, could therefore result in decreased RNA yields. This limitation can be circumvented by using Tris-nucleotides, because the RNA polymerase activity is less affected by high Tris concentrations compared to high Na concentrations. As shown in Example 5 and FIG. 12, the RNA yield is more sensitive to the addition of Na compared to Tris.

It is known in the art that instead of the ribonucleoside triphosphates GTP, ATP, GTP and UTP, respectively, modified nucleoside triphosphates (analogs) can also be used in in vitro transcription reactions, e.g. to enhance the stability of the RNA. As shown in Example 3 and FIG. 8, part or all of the UTP in a sequence-optimized NTP mix or in a sequence-optimized reaction mix can be replaced by pseudo-UTP.

Consequently, according to a preferred embodiment of the invention, a part or all of at least one ribonucleoside triphosphate in the sequence-optimized NTP mix or in the sequence-optimized reaction mix is replaced by a modified nucleoside triphosphate.

In a preferred embodiment of the invention, said modified nucleoside triphosphate is selected from the group consisting of pseudouridine-5'-triphosphate, 1-methylpseudouridine-5'-triphosphate, 2-thiouridine-5'-triphosphate, 4-thiouridine-5'-triphosphate and 5-methylcytidine-5'-triphosphate.

The person skilled in the art will understand that it is only possible before the start of the in vitro transcription to exactly establish the concentrations of the individual components of the sequence-optimized NTP mix or of the sequence-optimized reaction mix. Consequently, in a preferred embodiment of the present invention, the numbers and fractions as defined above reflect the initial conditions present in the sequence-optimized reaction mix or in the sequence-optimized NTP mix before the start of the transcription.

According to another preferred embodiment of the invention, in the course of the in vitro transcription the sequence-optimized reaction mix is supplemented with the sequence-optimized ribonucleoside triphosphate (NTP) mix as defined herein.

In the context of the present invention, it has been found that the RNA yield can be further increased by feeding additional amounts of the sequence-optimized NTP mix into the in vitro transcription reaction (NTP feed). As shown in Example 1 and FIG. 6, adding additional sequence-optimized NTP mix significantly increases the RNA yield.

The fresh sequence-optimized NTP mix is added in such a way that the desired ratio of the cap analog to the corresponding nucleotide e.g. GTP (e.g. 4:1) is maintained. Preferably, the fresh sequence-optimized NTP mix is added at the end of the in vitro transcription reaction, when all nucleotides in the sequence-optimized reaction mix are consumed. The ratio of the remaining cap analog to the freshly added corresponding nucleotide e.g. GTP (e.g. 4:1) can be approximately maintained because close to 100% of the cap analog remains at the end of the transcription reaction because only one cap analog can be incorporated per RNA molecule. This strategy results in the same capping efficiency, increased yields (>4.5-fold, depending on RNA sequence) and dramatically reduced costs. In addition, the increased NTP content prevents precipitation of RNA molecules during transcription, as is commonly seen for standard NTP concentrations (both in standard and sequence-optimized reactions).

The sequence-dependent incorporation of NTPs also allows monitoring of the progress of the in vitro transcription reaction. As shown in Example 6 and FIG. 13, the progress of the in vitro transcription reaction can be monitored by separating the unincorporated nucleotides from the in vitro transcription reaction and measuring the absorbance at 260 nm. The reason is that the decrease in the total concentration of all four NTPs directly correlates with the amount of RNA synthesized. This approach would not be possible as straightforwardly if a standard NTP mix with the same ratio of nucleoside triphosphates is used. A decrease in absorption at 260 nm can directly be translated into RNA molecules produced if NTPs are separated from RNA and DNA to avoid interference, e.g. by filtration through a membrane with a low molecular weight cut-off.

Methods for the quantification of nucleic acids and nucleotides are known in the art.

Spectroscopic methods for nucleic acid quantification include traditional absorbance measurements (Kolitz et al., 2013. Methods Enzymol. 530:331-6) and more sensitive fluorescence techniques using fluorescent dyes such as ethidium bromide and a fuorometer with a suitable excitation wavelength (e.g. 302 or 546 nm) (Gallagher, 2011. Current Protocols in Molecular Biology. 93:A.3D.1-A.3D.14). Consequently, in a preferred embodiment of the invention, the synthesizing of said RNA molecule by in vitro transcription is followed by separating and quantifying the unincorporated NTPs.

According to a preferred embodiment of the invention, said RNA molecule is selected from the group consisting of non-coding and coding RNA molecules.

A non-coding RNA (ncRNA) molecule is a functional RNA molecule that is not translated into a peptide or protein. Non-coding RNA molecules include highly abundant and functionally important RNAs such as transfer RNA (tRNA) and ribosomal RNA (rRNA), as well as RNAs such as snoRNAs, microRNAs, siRNAs, snRNAs, exRNAs, and piRNAs and the long ncRNAs that include examples such as Xist and HOTAIR (Esteller, 2011. Nat. Rev. Genet. 12(12): 861-74). Furthermore non-coding RNA molecules include immunostimulatory RNA (isRNA) molecules.

Preferably, the immunostimulatory RNA may be a linear single-stranded RNA. Even more preferred, the immunostimulatory RNA may be a long linear single-stranded non-coding RNA. In this context it is particularly preferred that the isRNA carries a triphosphate at its 5'-end.

The immunostimulatory RNA (isRNA) may comprise any RNA sequence known to be immunostimulatory, including, without being limited thereto, RNA sequences representing and/or encoding ligands of TLRs, preferably selected from human family members TLR1 to TLR10 or murine family members TLR1 to TLR13, more preferably selected from human family members TLR1 to TLR10, even more preferably from TLR7 and TLR8, ligands for intracellular receptors for RNA (such as RIG-I, MDA-5 or PKR) (Meylan and Tschopp, 2006. Mol. Cell 22, 561-569), or any other immunostimulatory RNA sequence. Furthermore, immunostimulatory RNA molecules may include any other RNA capable of eliciting an innate immune response. Without being limited thereto, such an immunostimulatory RNA may include ribosomal RNA (rRNA), transfer RNA (tRNA), messenger RNA (mRNA), and viral RNA (vRNA). Preferably the immunostimulatory RNA is a non-coding RNA. Such an immunostimulatory RNA may comprise a length of 1000 to 5000, of 500 to 5000, of 5 to 5000, or of 5 to 1000, 5 to 500, 5 to 250, of 5 to 100, of 5 to 50 or of 5 to 30 nucleotides.

According to a further particularly preferred embodiment, such immunostimulatory RNA molecules consist of or comprise RNA of formula (I):

(N$_u$G$_l$X$_m$G$_n$N$_v$)$_a$,     (formula (I))

wherein:
G is guanosine (guanine), uridine (uracil) or an analog of guanosine (guanine) or uridine (uracil), preferably guanosine (guanine) or an analog thereof;
X is guanosine (guanine), uridine (uracil), adenosine (adenine), thymidine (thymine), cytidine (cytosine), or an analog of these nucleotides (nucleosides), preferably uridine (uracil) or an analog thereof;
N is a nucleic acid sequence having a length of about 4 to 50, preferably of about 4 to 40, more preferably of about 4 to 30 or 4 to 20 nucleic acids, each N independently being selected from guanosine (guanine), uridine (uracil), adenosine (adenine), thymidine (thymine), cytidine (cytosine) or an analog of these nucleotides (nucleosides);
a is an integer from 1 to 20, preferably from 1 to 15, most preferably from 1 to 10;
l is an integer from 1 to 40,
    wherein when l=1, G is guanosine (guanine) or an analog thereof,
        when l>1, at least 50% of these nucleotides (nucleosides) are guanosine (guanine) or an analog thereof;
m is an integer and is at least 3;
    wherein when m=3, X is uridine (uracil) or an analog thereof, and
        when m>3, at least 3 successive uridines (uracils) or analogs of uridine (uracil) occur;
n is an integer from 1 to 40,
    wherein when n=1, G is guanosine (guanine) or an analog thereof,
        when n>1, at least 50% of these nucleotides (nucleosides) are guanosine (guanine) or an analog thereof;
u,v may be independently from each other an integer from 0 to 50,
    preferably wherein when u=0, v≥1, or
        when v=0, u≥1;
wherein the nucleic acid molecule of formula (I) has a length of at least 50 nucleotides, preferably of at least 100 nucleotides, more preferably of at least 150 nucleotides, even more preferably of at least 200 nucleotides and most preferably of at least 250 nucleotides.

According to a most preferred embodiment, the RNA molecule according to formula (I) may be selected from e.g. the following sequence:

```
                                           (R2025; SEQ ID NO: 4)
GGGAGAAAGCUCAAGCUUAUCCAAGUAGGCUGGUCACCUGUACAACGUAG

CCGGUAUUUUUUUUUUUUUUUUUUUUUUGACCGUCUCAAGGUCCAAGUUA

GUCUGCCUAUAAAGGUGCGGAUCCACAGCUGAUGAAAGACUUGUGCGGUA

CGGUUAAUCUCCCCUUUUUUUUUUUUUUUUUUUUAGUAAAUGCGUCUAC

UGAAUCCAGCGAUGAUGCUGGCCCAGAUCUUCGACCACAAGUGCAUAUAG

UAGUCAUCGAGGGUCGCCUUUUUUUUUUUUUUUUUUUUUUGGCCCAGUU

CUGAGACUUCGCUAGAGACUACAGUUACAGCUGCAGUAGUAACCACUGCG

GCUAUUGCAGGAAAUCCCGUUCAGGUUUUUUUUUUUUUUUUUUUUCCGC

UCACUAUGAUUAAGAACCAGGUGGAGUGUCACUGCUCUCGAGGUCUCACG

AGAGCGCUCGAUACAGUCCUUGGAAGAAUCUUUUUUUUUUUUUUUUUUU

UUGUGCGACGAUCACAGAGAACUUCUAUUCAUGCAGGUCUGCUCUAG
```

A coding RNA is a functional RNA molecule that can be translated into a peptide or protein. Preferably the coding RNA molecule comprises at least one open reading frame coding for at least one peptide or protein.

In this context the coding RNA molecule can comprise one (monocistronic), two (bicistronic) or more (multicistronic) open reading frames (ORF). The coding RNA molecule can be a messenger RNA (mRNA) molecule, viral RNA molecule or self-replicating RNA molecule (replicon). Preferably the RNA molecule is an mRNA.

According to a preferred embodiment of the invention, said RNA molecule is longer than 100 nucleotides. It is equally preferred that the RNA has a length between 100 and 15.000 nucleotides, 100 and 12.500 nucleotides, 100 and 10.000 nucleotides, 100 and 7.500 nucleotides, 100 and 5.000 nucleotides, 100 and 2.500 nucleotides, 100 and 1.500 nucleotides, or 100 and 1.000 nucleotides.

In a preferred embodiment of the invention, said synthesizing of an RNA molecule of a given sequence is performed as a large scale synthesis.

According to the present invention, the term "large scale" refers to a reaction yield of said RNA molecule in the order of milligram quantities, preferably of at least one gram.

According to a preferred embodiment of the present invention, the in vitro transcription reaction is carried out in a bioreactor, also referred to as a transcription reactor or RNA reactor for large-scale synthesis of RNA. Therefore, the bioreactor can be adapted to carry out the above described method of the present invention.

According to the present invention, such a bioreactor for synthesizing RNA molecules of a given sequence, preferably on a large scale, is a modularly designed in vitro transcription reactor system, comprising a reaction module for carrying out in vitro RNA transcription reactions in a sequence-optimized reaction mix, a capture module for temporarily capturing the transcribed RNA molecules, and a control module for controlling the infeed of components of the sequence-optimized reaction mix into the reaction module. Here, the reaction module comprises a filtration membrane for separating nucleotides from the reaction mix, and the control of the infeed of the components of the sequence-optimized reaction mix by the control module is based on a measured concentration of separated nucleotides.

The term bioreactor or transcription reactor as used herein refers to a chamber or test tube or column wherein an in vitro transcription reaction is carried out under specified conditions. The bioreactor may be thermally regulated to maintain accurately a specific temperature, usually between 4 and 40° C. The bioreactor may be configured with an inflow or feed line and an exit port. The bioreactor may be a stirred-cell with provision for variable rates of stirring.

According to the present invention, the bioreactor comprises a filtration membrane for separating nucleotides from the reaction mix, in particular for separating nucleotides and other low molecular weight components from the sequence-optimized reaction mix. The introduction of a filtration membrane in such a flow system, for example an ultrafiltration membrane, is used for separation of high molecular weight components, such as e.g. proteins and/or polynucleotides, from low molecular weight components, such as nucleotides. The filtration membrane serves to selectively retain the immobilized DNA template, the RNA polymerase and the synthesized RNA molecules in the reactor core of the reaction module whereas smaller molecules such as nucleotides (NTPs) can pass the filtration membrane into a separate smaller compartment of the reaction module, i.e. the filtration compartment. The nucleotide concentration can then be measured, for example, by spectroscopic analysis in the separated fluid containing the low molecular weight components. Alternatively, the nucleotide concentration can be measured by an online HPLC system. The application of a sequence-optimized NTP mix in this reactor system allows the real-time measurement of the nucleotide concentration during the in vitro transcription reaction to monitor the progress of the in vitro transcription reaction.

Suitable filtration membranes can consist of various materials known to a person skilled in the art (van de Merbel, 1999. J. Chromatogr. A 856(1-2):55-82). For example, membranes may consist of regenerated or modified cellulose or of synthetic materials. The latter include polysulfone (PSU), polyacrylo-nitrile (PAN), polymethylmethacrylate (PMMA), mixtures of polyarylether-sulfones, polyvinylpyrrolidone and polyamide (Polyamix®). For example, The polysulfones include polyethersulfone [poly(oxy-1,4-phenylsulfonyl-1,4-phenyl), abbreviated PES]. In some exemplary embodiments, polyethersulfone may be utilized as a semipermeable membrane for the use according to the disclosure. In some cases PES membranes include increased hydrophilicity (and/or the improved wettability of the membrane with water) compared to PSU membranes. In some embodiments, the wettability of PES membranes can, for example, be further increased by the inclusion of the water-soluble polymer polyvinylpyrrolidone.

An important parameter that influences the flux of molecules across the filtration membrane is the pore size or pore-size distribution. A filtration membrane is usually characterized by its molecular weight cut-off (MWCO) value, i.e. a specific size limitation, which is defined as the molecular mass of the smallest compound, which is retained for more than 90%. For each application, a proper MWCO value needs to be selected so that high molecular weight compounds are sufficiently retained, but at the same time a rapid transport of the analyte is ensured. The filtration membrane of the bioreactor of the present invention may have a MWCO in a range from 10 to 100 kDa, 10 to 75 kDa, 10 to 50 kDa, 10 to 25 kDA or 10 to 15 kDa. Even more preferred, the filtration membrane has a MWCO in a range of approximately 10 to 50 kDa. Preferably, the filtration membrane is selected from the group of regenerated cellulose, modified cellulose, polysulfone (PSU), polyacrylonitrile (PAN), polymethylmethacrylate (PMMA), polyvinyl alcohol (PVA) and polyarylethersulfone (PAES).

According to a preferred embodiment of the present invention, the bioreactor comprises a DNA template immobilized on a solid support as basis for the RNA transcription reaction. The immobilization of the DNA template allows the repeated usage of the template and reduces the contamination of the RNA product by residual DNA. In addition, the immobilization makes the use of DNAse dispensable for the removal of the DNA template from the final RNA product. The DNA template, which is preferably immobilized on a solid support in the reaction core of the reaction module, can represent a chemically synthesized DNA molecule, an isolated DNA restriction fragment, a plasmid or an amplified DNA molecule, for example by an amplification process such as the polymerase chain reaction (PCR). The DNA template can be a double-stranded duplex or a unit that comprises a double-stranded promoter region upstream of a single-stranded RNA coding region. The DNA template may be modified with a ligand for immobilization to a solid support at the 5' end, the 3' end, or at an internal nucleotide of a DNA strand.

According to the invention, the term "solid support" relates to every undissolved support being able to immobilize a DNA molecule on its surface. The solid support may be selected from the group consisting of agarose, modified agarose, sepharose, polystyrene, latex, cellulose, and ferro- or ferrimagnetic particles. Methods and strategies for choosing appropriate solid supports and for coupling DNA molecules to said solid supports are known in the art (see e.g. Arndt-Jovin et al. 1975. Eur. J. Biochem. 54(2):411-8; Kerrigan et al., 2001. Current Protocols in Molecular Biology. 24:12.10.1-12.10.18; WO1995/08626). The immobilization of the DNA template on the solid support can be via a covalent linkage or a non-covalent linkage. Preferably, the immobilization of the DNA template occurs through a non-covalent linkage. For example, the immobilization of a DNA template to a solid support can occur through a non-covalent biotin-streptavidin interaction. The non-coding strand of the DNA template can be modified with a 5'-terminal biotin group which functions to immobilize the DNA strand to a solid support matrix comprising streptavidin protein. The complementary RNA-coding strand of the DNA template can remain non-immobilized. It is also possible to immobilize DNA templates to solid supports through other types of non-covalent linkages, e.g., poly(A)-poly(T), and poly(G)-poly(C) interactions. Equally preferred, the immobilization of the DNA template occurs through a covalent linkage, e.g., ester linkage or derivative thereof. In general, before coupling, the solid support can contain active groups such as NHS, carbodimide etc. to enable the coupling reaction with the DNA molecule. The DNA molecule can be coupled to the solid support by direct coupling (e.g. using functional groups such as amino-, sulfhydryl-, carboxyl-, hydroxyl-, aldehyde-, and ketone groups). The linkage to the solid support material may involve spacers to optimize the spatial separation of the DNA template from the support.

The spacer may be provided by insertion of additional nucleotides at the 5' end of the DNA template.

According to a preferred embodiment of the present invention, the capture module of the bioreactor comprises a resin/solid phase to capture the transcribed RNA molecules and to separate the transcribed RNA molecules from other soluble components of the sequence-optimized transcription reaction mix. Preferably, the capture module comprises means for purifying the captured transcribed RNA molecules, e.g. by a washing process or the like. Further preferably, the capture module comprises means for eluting the captured transcribed RNA molecules, preferably by means of an elution buffer.

According to a further preferred embodiment, the bioreactor further comprises a reflux module for returning the residual filtrated sequence-optimized reaction mix, i.e. the other soluble components of the sequence-optimized transcription reaction mix besides the transcribed RNA molecules, to the reaction module from the capture module after capturing the transcribed RNA molecules, preferably wherein the means for returning the residual filtrated sequence-optimized reaction mix is a pump. Here, the reflux module preferably comprises immobilized enzymes, such as pyrophosphatase, or resin to capture disruptive components, such as phosphate.

In a preferred embodiment, the bioreactor comprises at least one ion-selective electrode. In the context of the present invention, the term 'ion-selective electrode' relates to a transducer (e.g. a sensor) that converts the activity of a specific ion dissolved in a solution into an electrical potential, wherein the electrical potential may be measured, for instance, by using a volt meter or a pH meter. In particular, the term 'ion-selective electrode' as used herein comprises a system, which comprises or consists of a membrane having selective permeability, wherein the membrane typically separates two electrolytes. An ion-selective electrode as used herein typically comprises a sensing part, which preferably comprises a membrane having selective permeability and a reference electrode. The membrane is typically an ion-selective membrane, which is characterized by different permeabilities for different types of ions. Preferably, the at least one ion-selective electrode of the bioreactor comprises a membrane selected from the group consisting of a glass membrane, a solid state membrane, a liquid based membrane, and a compound membrane.

In preferred embodiments, the bioreactor as described herein comprises at least one ion-selective electrode, wherein the at least one ion-selective electrode comprises or consists of a system comprising a membrane, preferably a membrane as described herein, more preferably an electrochemical membrane, having different permeabilities for different types of ions, wherein the membrane, preferably a membrane as described herein, more preferably an electrochemical membrane, preferably separates two electrolytes. In one embodiment, the membrane comprises or consists of a layer of a solid electrolyte or an electrolyte solution in a solvent immiscible with water. The membrane is preferably in contact with an electrolyte solution on one or both sides. In a preferred embodiment, the ion-selective electrode comprises an internal reference electrode. Such internal reference electrode may be replaced in some embodiments, for example by a metal contact or by an insulator and a semiconductor layer.

An ion-selective electrode permits highly sensitive, rapid, exact and non-destructive measurement of ion activities or ion concentrations in different media. Apart from direct measurements of ion activities or ion concentrations they can serve, in particular by using a calibration curve, for continuous monitoring of concentration changes, as elements for control of dosage of agents or as very accurate indicator electrodes in potentiometric titrations.

In preferred embodiments, the bioreactor comprises at least one ion-selective electrode, preferably as described herein, for measuring the concentration of one or more types of ions in at least one compartment of the bioreactor. For example, the at least one ion-selective electrode may be used to measure the concentration of one or more types of ions in a reaction module, a control module or a reflux module of the bioreactor. Preferably, the at least one ion-selective electrode is used for measuring the concentration of one or more types of ions in the reaction module, more preferably in the reaction core or in the filtration compartment. Furthermore, the at least one ion-selective electrode may be comprised in a sensor unit of the bioreactor, preferably as defined herein. The ion-selective electrode may be located in the bioreactor itself, on the bioreactor or outside of the bioreactor (e.g. connected to the bioreactor by a bypass). In the context of the present invention, the phrase 'the bioreactor comprises at least one ion-selective electrode' may thus refer to a situation, where the at least one ion-selective electrode is a part of the bioreactor, or to a situation, where the at least one ion-selective electrode is a separate physical entity with respect to the bioreactor, but which is used in connection with the bioreactor.

According to some embodiments, the bioreactor comprises at least one ion-selective electrode, preferably as described herein, for measuring the concentration of one or more types of ions in a liquid comprised in at least one compartment of the bioreactor, wherein the ion is preferably selected from the group consisting of $H^+$, $Na^+$, $K^+$, $Mg^{2+}$, $Ca^{2+}$, $Cl^-$ and $PO_4^{3-}$.

According to some embodiments, the bioreactor comprises at least one ion-selective electrode, preferably as described herein, which is connected to a potentiometer, preferably a multi-channel potentiometer (for instance, a CITSens Ion Potentiometer 6-channel, high-resolution; C-CIT Sensors AG, Switzerland).

In a preferred embodiment, the bioreactor comprises at least one ion-selective electrode, wherein the at least one ion-selective electrode is preferably a tube electrode, more preferably selected from the group consisting of a $Mg^{2+}$ selective tube electrode, a $Na^+$ selective tube electrode, a $Cl^-$ selective tube electrode, a $PO_4^{3-}$ selective tube electrode, a pH-selective tube electrode and a $Ca^{2+}$ selective tube electrode, preferably used in connection with a potentiometer. Even more preferably, the bioreactor comprises at least one ion-selective electrode, wherein the at least one ion-selective electrode is preferably selected from the group consisting of a CITSens Ion $Mg^{2+}$ selective mini-tube electrode, a CITSens Ion $Na^+$ selective mini-tube electrode, a CITSens Ion $Cl^-$ selective mini-tube electrode, a CITSens Ion $PO_4^{3-}$ selective mini-tube electrode, a CITSens Ion pH-selective mini-tube electrode and a CITSens Ion $Ca^{2+}$ selective mini-tube electrode (all from C-CIT Sensors AG, Switzerland), preferably in connection with a potentiometer, more preferably with a multi-channel ptentiometer, such as a CITSens Ion Potentiometer 6-channel, high-resolution (C-CIT Sensors AG, Switzerland).

Ion-selective electrodes have numerous advantages for practical use. For example, they do not affect the tested solution, thus allowing non-destructive measurements. Furthermore, ion-selective electrodes are mobile, suitable for direct determinations as well as titration sensors, and cost effective. The major advantage of the use of an ion-selective electrode in a bioreactor (e.g. a transcription reactor) is the possibility to measure in situ without sample collection and in a non-destructive manner.

According to a preferred embodiment of the present invention, the bioreactor, or more precisely the control module of the bioreactor comprises a sensor unit for the analysis of critical process parameters, such as pH-value, conductivity and nucleotide concentration in the sequence-optimized reaction mix. Preferably, the sensor unit of the bioreactor comprises a sensor, such as an UV flow cell for UV 260/280 nm, for the real-time measurement of the nucleotide concentration during the in vitro transcription reaction. Preferably, the sensor of the sensor unit measures the nucleotide concentration, as a process parameter, by photometric analysis.

According to a preferred embodiment of the present invention, the bioreactor comprises a control module. Data collection and analyses by the control module allows the control of the integrated pump system (actuator) for repeated feeds of components of the sequence-optimized NTP mix or components of the sequence-optimized reaction mix, e.g. buffer components, RNA polymerase or nucleotides. Tight controlling and regulation allows to perform the in vitro transcription reaction under an optimal steady-state condition resulting in high product yield. Preferably the control module controls the addition of the sequence-optimized ribonucleoside triphosphate (NTP) mix to the sequence-optimized reaction mix, preferably wherein said bioreactor comprises an actuator for addition of the sequence-optimized ribonucleoside triphosphate (NTP) mix to the sequence-optimized reaction mix. Further, the actuator can also add other reaction components of the sequence-optimized reaction mix, such as a buffer components, or $Mg^{++}$, to the in vitro transcription reaction mix. According to a further preferred embodiment of the present invention, the bioreactor operates in a semi-batch mode or in a continuous mode. The term semi-batch as used herein refers to the operation of the in vitro transcription reaction as a repetitive series of transcription reactions. For example, the reaction is allowed to proceed for a finite time at which point the product is removed, new reactants added, and the complete reaction repeated. The term continuous-flow as used herein refers to a reaction that is carried out continually in a bioreactor core with supplemental reactants constantly added through an input feed line and products constantly removed through an exit port. A continuous-flow reactor controls reagent delivery and product removal through controlled device flow rates, which is advantageous for reactions with reagent limitations and inhibitory products.

In another aspect, the present invention relates to an RNA molecule obtainable by the inventive method as disclosed herein. Preferably, the RNA obtained by the inventive method is characterized by a reduced immunostimulatory activity in comparison to RNA obtained by prior art methods, in particular as compared to RNA obtained by an in vitro transcription method, wherein the NTP mix is not optimized with respect to the transcript sequence, such as a method using a standard equimolar NTP mix.

In a further aspect, the present invention also relates to the use of a sequence-optimized ribonucleoside triphosphate (NTP) mix optimized for an RNA molecule of a given sequence for the synthesis of said RNA molecule. All definitions and specific embodiments relating to the sequence-optimized ribonucleoside triphosphate (NTP) mix made above with respect to the method of the invention also apply to said use of the invention.

Especially, according to a preferred embodiment of the invention, the sequence-optimized NTP mix has been optimized by a method comprising the steps of:
a) determining the fraction (1) of each of the four nucleotides G, A, C and U in said RNA molecule, and
b) preparing the sequence-optimized ribonucleoside triphosphate (NTP) mix comprising the four ribonucleoside triphosphates (NTPs)GTP, ATP, CTP and UTP, wherein the fraction (2) of each of the four ribonucleoside triphosphates in the sequence-optimized ribonucleoside triphosphate (NTP) mix corresponds to the fraction (1) of the respective nucleotide in said RNA molecule.

In a further aspect, the present invention also relates to a sequence-optimized ribonucleoside triphosphate (NTP) mix for the synthesis of an RNA molecule of a given sequence comprising the four nucleoside triphosphates GTP, ATP, CTP and UTP, wherein the fraction (2) of each of the four nucleoside triphosphates in the sequence-optimized ribonucleoside triphosphate (NTP) mix corresponds to the fraction (1) of the respective nucleotide in said RNA molecule.

In a further aspect, the present invention also relates to a kit comprising a sequence-optimized ribonucleoside triphosphate (NTP) mix optimized for an RNA molecule of a given sequence as defined above. The sequence-optimized NTP mix can be provided in one tube containing all four types of NTPs (GTP, ATP, CTP and UTP) or each NTP in a separate tube. All definitions or specific embodiments made above with respect to the method of the invention also apply to said kit of the invention.

BRIEF DESCRIPTION OF THE FIGURES

The figures shown in the following are merely illustrative and shall describe the present invention in a further way. These figures shall not be construed to limit the present invention thereto.

FIG. 1: G/C optimized mRNA sequence of R1871 coding for *Homo sapiens* prostate stem cell antigen (HsPSCA), which corresponds to SEQ ID NO: 1.

FIG. 2: G/C optimized mRNA sequence of R2988 coding for *Photinus pyralis* luciferase (PpLuc), which corresponds to SEQ ID NO: 2.

FIG. 3: G/C optimized mRNA sequence of R1626 coding for *Homo sapiens* Mucin-1 signal peptide/epidermal growth factor receptor/Mucin-1 fusion protein (EGFR/Mucin-1), which corresponds to SEQ ID NO: 3.

FIG. 4: Non-coding immunostimulatory RNA sequence of R2025, which corresponds to SEQ ID NO: 4.

(A) The RNA yield of standard transcription reactions reaches after about 30 minutes a plateau of approx. 1.4 mg/ml RNA for the 5337 nucleotide long RNA encoding EGFR/Mucin-1 (R1626) and of approx. 1.8 mg/ml RNA for the 589 nucleotide long RNA encoding HsPSCA (R1871).

(B) The RNA yield of sequence-optimized transcription reactions is significantly higher compared to standard transcription reactions. After 60 minutes (R1626) and 120 minutes (R1871) both RNAs reach a similar plateau of approximately 3.9 mg/ml RNA. Mean and standard deviation of triplicates are shown.

Figure 6:
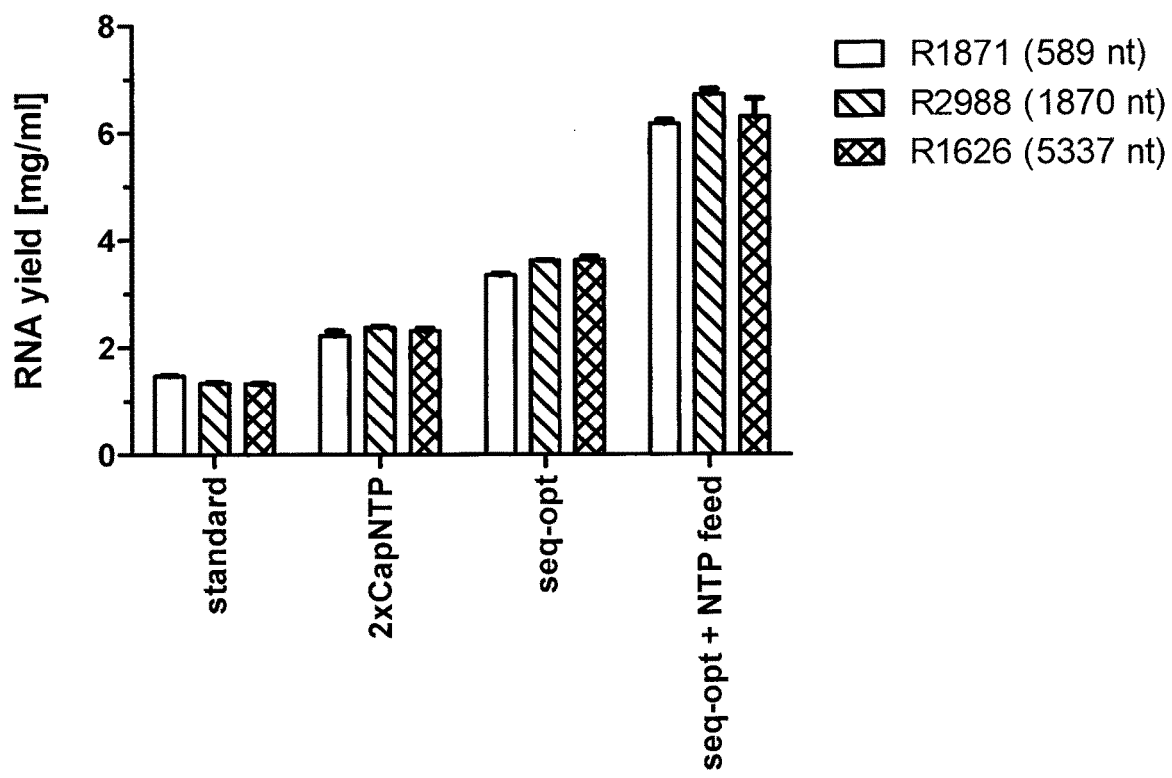

FIG. 6: Comparison of RNA yields obtained from using standard and sequence-optimized nucleotide (CapNTP) mixes for mRNA encoding HsPSCA (R1871), Luciferase (PpLuc, R2988) and EGFR/Mucin-1 (R1626). The experiment was performed as described in Example 1 (reaction time 5 hours).

The RNA yields for the three different RNA molecules of different lengths are roughly the same for each type of transcription reaction. However, different yields are obtained depending on the nucleotide mix used for the in vitro transcription.

Standard transcription (equal NTP concentration for each NTP) yields about 1.5 mg/ml RNA, transcription with a twofold concentrated Cap-NTP mix (2×CapNTP) about 3.0 mg/ml RNA, sequence-optimized (seq-opt) transcription about 3.9 mg/ml RNA and sequence-optimized transcription with NTP feed about 6.75 mg/ml RNA. Mean and standard deviation of triplicates are shown.

Figure 7:
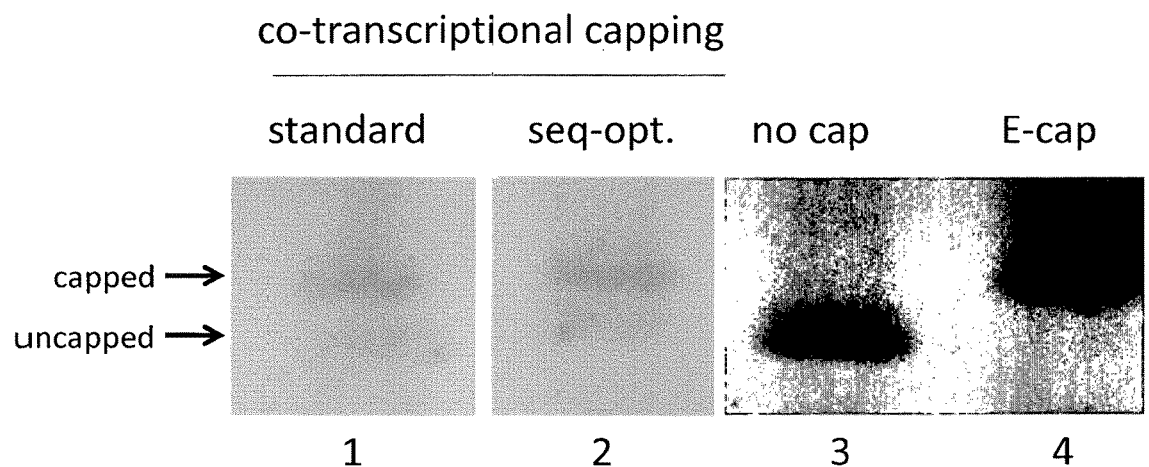

FIG. 7: Analysis of capping efficiency achieved by standard and sequence-optimized in vitro transcription of *Photinus pyralis* Luciferase (PpLuc) mRNA.

RNAs were cleaved with the hammerhead ribozyme HHNUH2d as described in example 2 and the resulting RNA fragments were separated by denaturing polyacrylamide gel electrophoresis (dPAGE). Non-capped (no cap) and enzymatically capped (E-cap) RNAs served as controls.

Comparable capping efficiencies were achieved when using standard and sequence-optimized NTP mixes for the synthesis of mRNAs encoding *Photinus pyralis* Luciferase (PpLuc).

Figure 8:
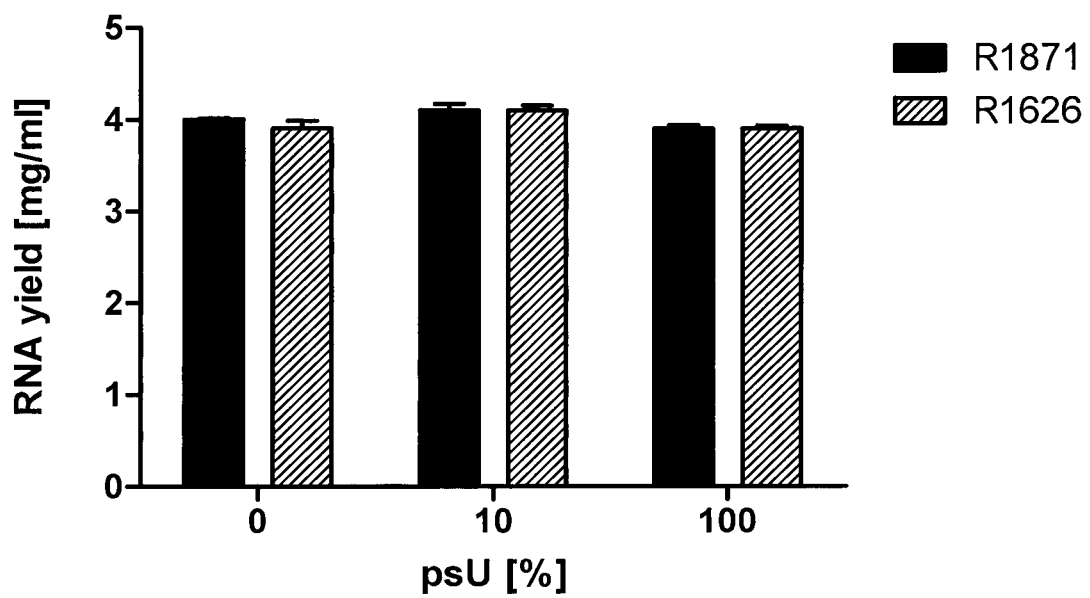

FIG. 8: Comparison of RNA yields using UTP and pseudo-UTP in sequence-optimized CapNTP mixes for Mucin-1 signal peptide/epidermal growth factor receptor/Mucin-1 fusion protein (EGFR/Mucin-1) mRNA (R1626) and prostate stem cell antigen (HsPSCA) mRNA (R1871). The experiments were performed as described in Example 3. In the mixes UTP was replaced with 0%, 10%, or 100% pseudo-UTP (psU) as indicated. The mean and standard deviation of triplicates are shown.

Figure 9:
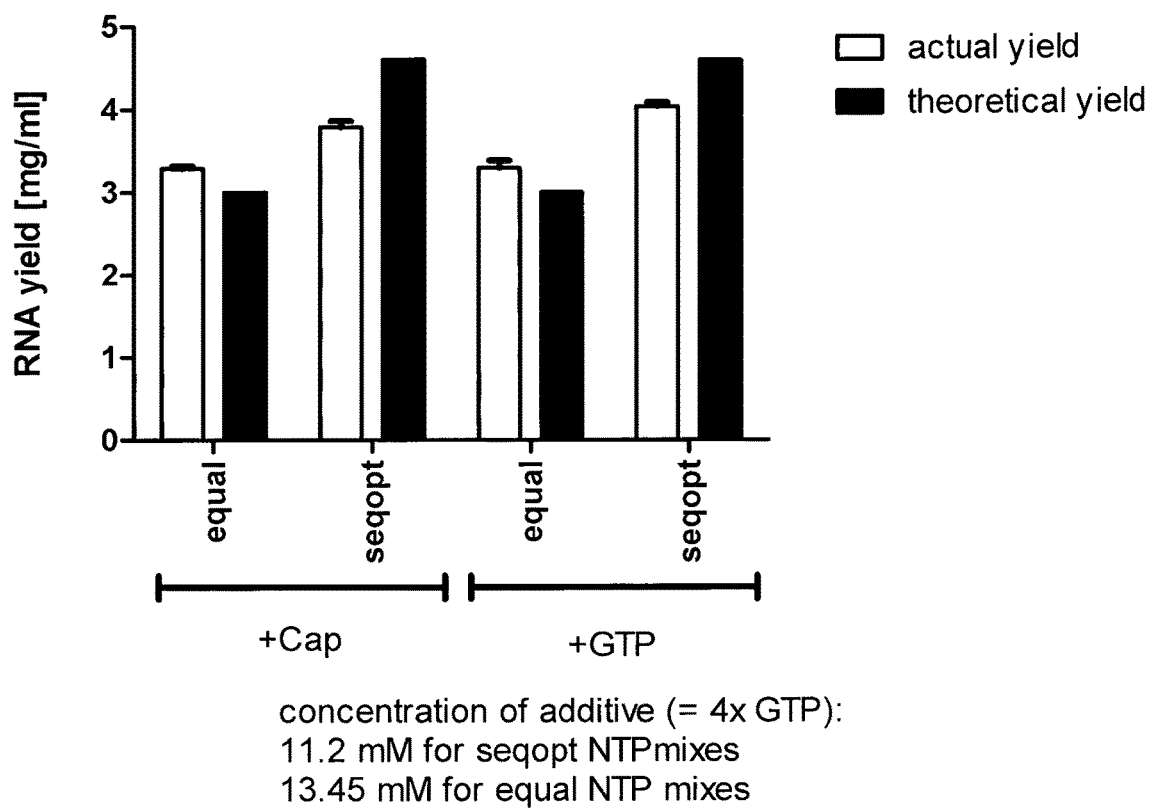

FIG. 9: Comparison of theoretical and actual RNA yields for the noncoding immunostimulatory RNA R2025 using standard (equal) and sequence-optimized (seqopt) NTP mixes in the presence of additional nucleotides (13.45 mM total NTP concentration; 13.45 mM cap or GTP for equal mixes (4-fold excess over GTP); 11.2 mM cap or GTP for sequence-optimized NTP mixes (4-fold excess over GTP)). White bars: actual yields. Black bars: theoretical yields. The experiments were performed as described in Example 4. Mean and standard deviation of triplicates are shown.

Figure 10:
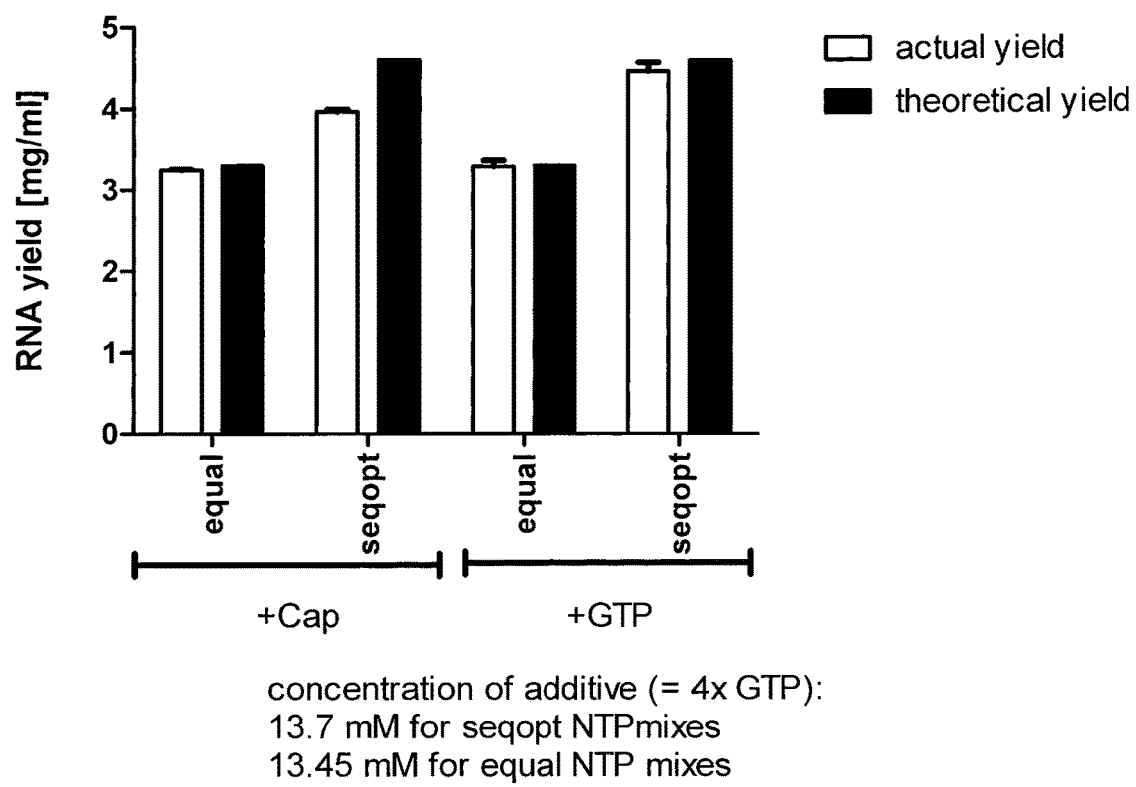

FIG. 10: Comparison of theoretical and actual RNA yields for the mRNA encoding *Homo sapiens* prostate stem cell antigen (HsPSCA) (R1871) using standard (equal) and sequence-optimized NTP ratios in the presence of additional nucleotides (13.45 mM total NTP concentration; 13.45 mM cap or GTP for equal mixes (4-fold excess over GTP); 13.7 mM cap or GTP for sequence-optimized NTP mixes (4-fold excess over GTP)). White bars: actual yields. Black bars: theoretical yields. The experiments were performed as described in Example 4.

Figure 11:
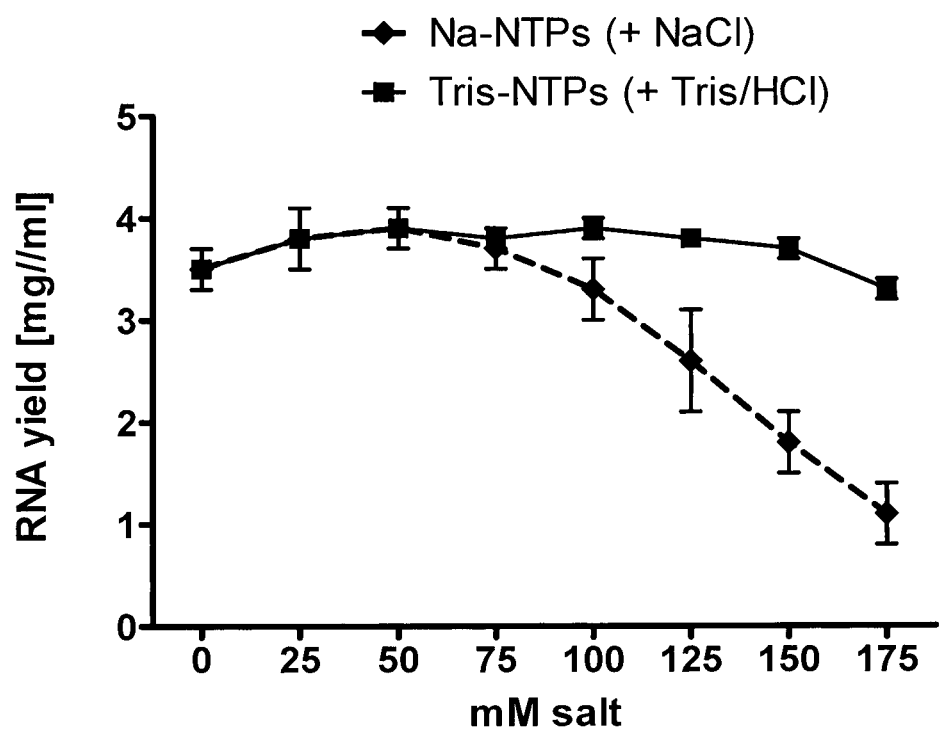

FIG. 11: Transcription efficiencies using sequence-optimized NTP mixes of Na-NTPs or Tris-NTPs, in the presence of respective added salts (NaCl; Tris/HCl, pH7.5). The experiment was performed as described in Example 5.

Figure 12:
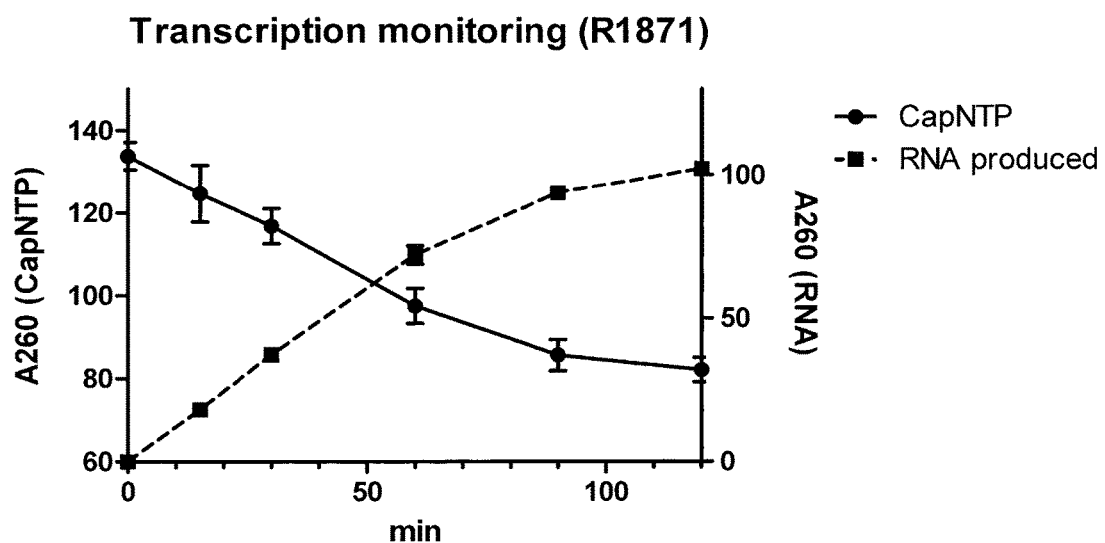

FIG. 12: Monitoring of the progress of the sequence-optimized transcription reaction by measuring the amount of produced RNA and the consumption of nucleotide mix. The experiment was performed as described in Example 6.

FIG. 13: RNA yields for mRNA encoding *Photinus pyralis* luciferase (PpLuc) (R2988) depending on cap concentration. The mRNA was synthesized by in vitro transcription using total NTP concentrations of 4 mM and 13.45 mM of the PpLuc sequence-optimized NTP mix in the presence of varying concentrations of cap analog. The experiment was performed as described in Example 7. (A) Actual RNA [mg/ml]. (B) Relative RNA yield [%].

FIG. 14: RNA yields for mRNA encoding *Homo sapiens* prostate stem cell antigen (HsPSCA) (R1871) depending on cap concentration. The mRNA was synthesized by in vitro transcription using total NTP concentrations of 2 mM, 4 mM and 13.45 mM of the HsPSCA sequence-optimized NTP mix in the presence of varying concentrations of cap analog. The experiment was performed as described in Example 7. (A) Actual RNA yield [mg/ml]. (B) Relative RNA yield [%].

FIG. 15: RNA yields for mRNA encoding *Homo sapiens* prostate stem cell antigen (HsPSCA) (R1871) depending on GTP start nucleotide concentration. The mRNA was synthesized by in vitro transcription using total NTP concentrations of 13.45 mM of the HsPSCA sequence-optimized NTP mix to which GTP start nucleotide was added up to a concentration of 20 mM. The experiment was performed as described in Example 8. (A) Actual RNA yield [mg/ml]. (B) Relative RNA yield [%].

FIG. 16: RNA yields for mRNA encoding *Photinus pyralis* luciferase (PpLuc) (R2988) depending on GTP start nucleotide concentration. The mRNA was synthesized by in vitro transcription using total NTP concentrations of 13.45 mM of the PpLuc sequence-optimized NTP mix to which GTP start nucleotide was added up to a concentration of 20 mM. The experiment was performed as described in Example 8. (A) Actual RNA yield [mg/ml]. (B) Relative RNA yield [%].

FIG. 17: RNA yields for mRNA encoding EGFR/Mucin-1 (R1626) depending on GTP start nucleotide concentration. The mRNA was synthesized by in vitro transcription using total NTP concentrations of 13.45 mM of the EGFR/Mucin-1 sequence-optimized NTP mix to which GTP start nucleotide was added up to a concentration of 20 mM. The experiment was performed as described in Example 8. (A) Actual RNA yield [mg/ml]. (B) Relative RNA yield [%].

Figure 18:
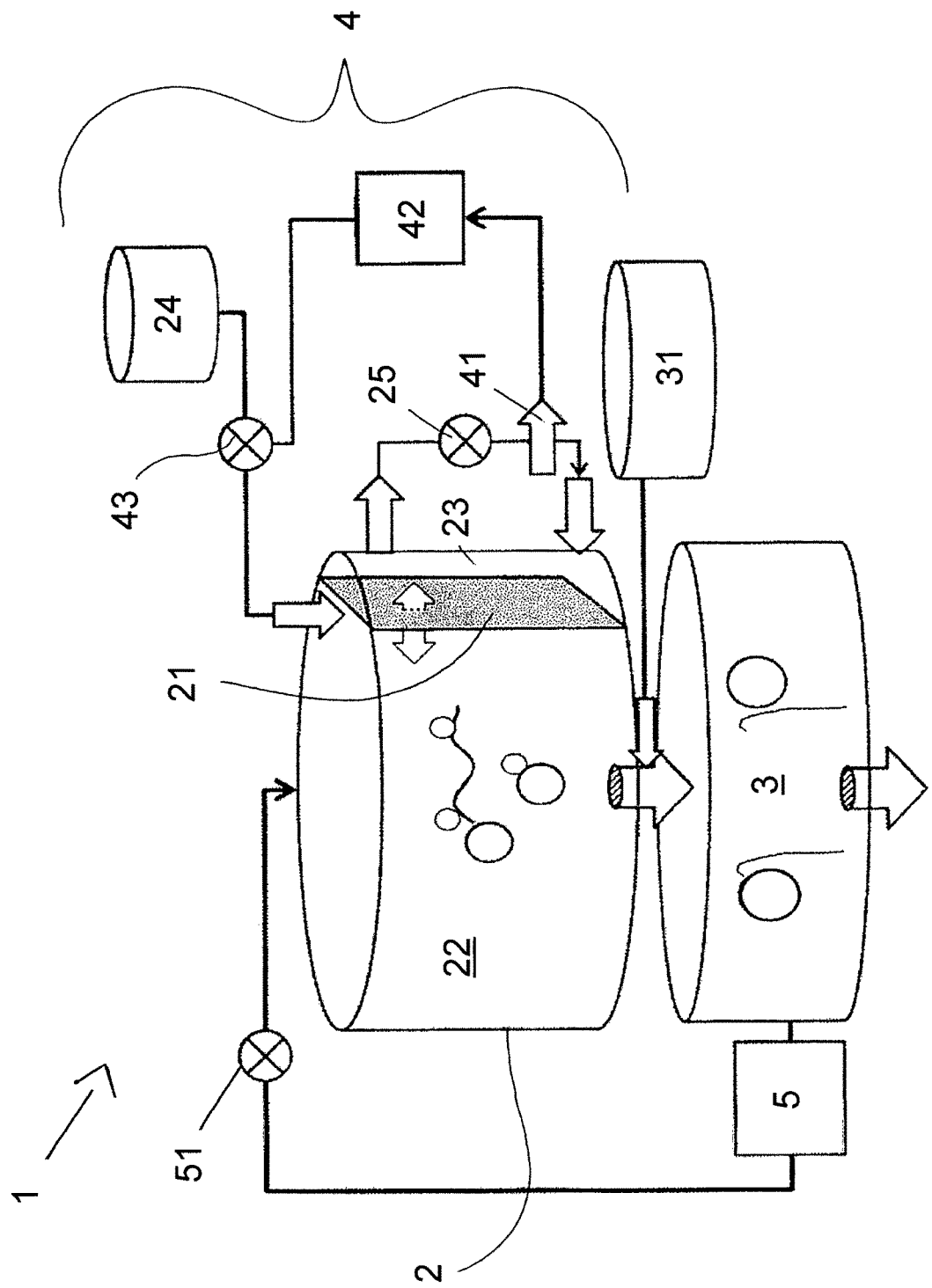

FIG. 18: Bioreactor in a schematic illustration, including modules for continuous or semi-batch process, with resin-immobilized linear DNA as template for the transcription reaction.

Figure 19:
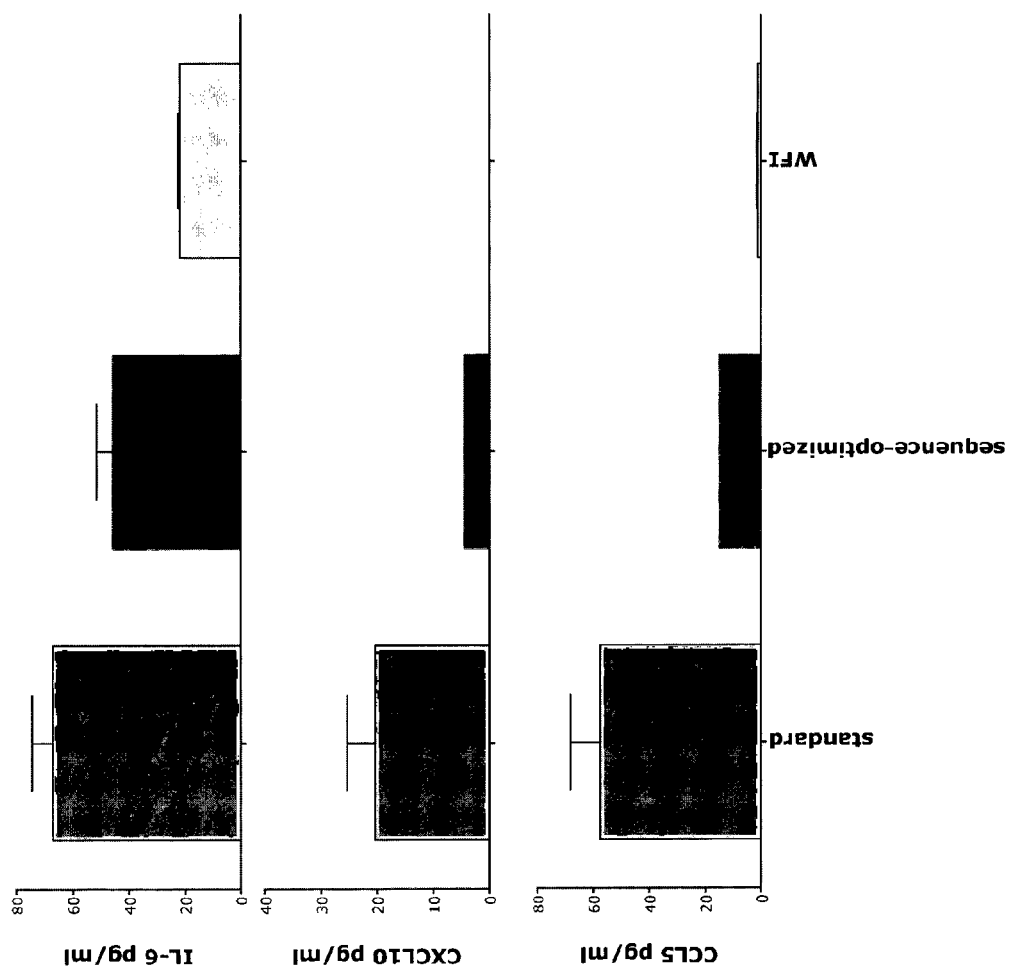

FIG. 19: Reduced immunostimulation by RNA synthesized with a sequence-optimized NTP mix compared to a standard equimolar NTP mix. Cytokine and chemokine levels in cell supernatants were measured as described in Example 10.

FIG. 20: G/C optimized mRNA sequence encoding HA from Influenza A H1N1 (Netherlands 2009), which corresponds to SEQ ID NO: 6 (Example 11).

Figure 21:
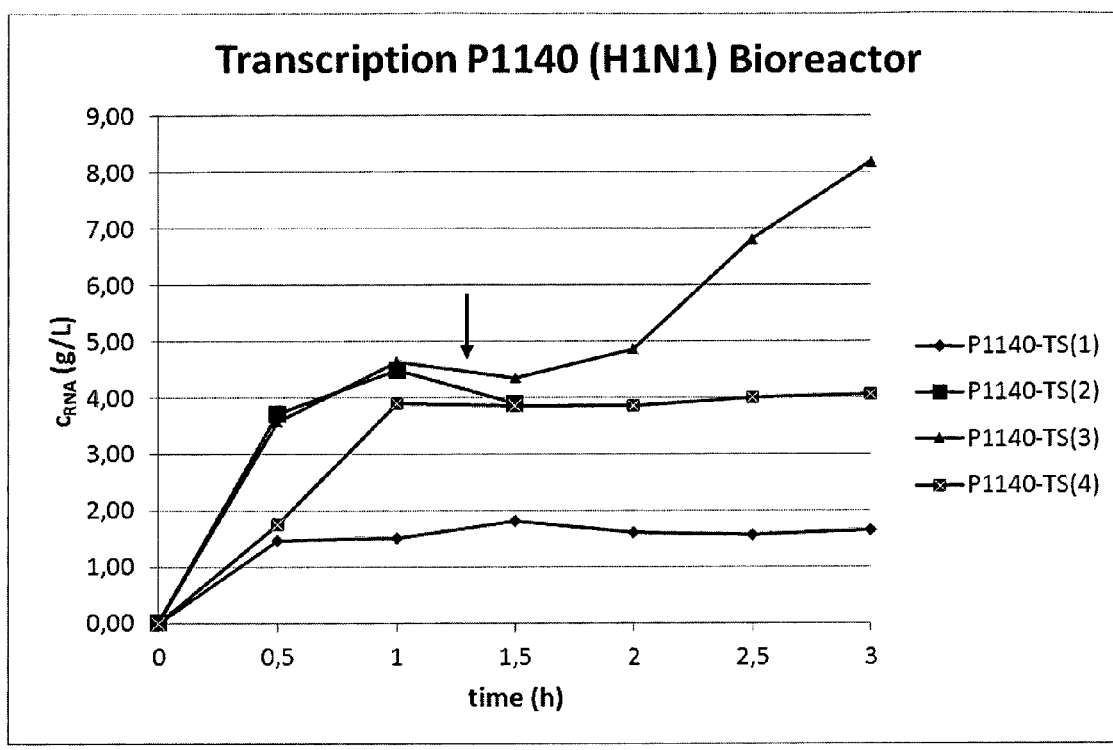

FIG. 21: RNA yields over time for mRNA encoding HA (Example 11). The RNA yield at different time points is shown for RNA obtained by in vitro transcription in a bioreactor using a standard NTP mix (TS(1)), by sequence-optimized transcription in a bioreactor without feed (TS(2)), by sequence-optimized transcription in a bioreactor with feed (TS(3)), or by sequence-optimized transcription in a bioreactor with reduced T7 RNA polymerase concentration and reduced template concentration (TS(4)), respectively.

Figure 22:
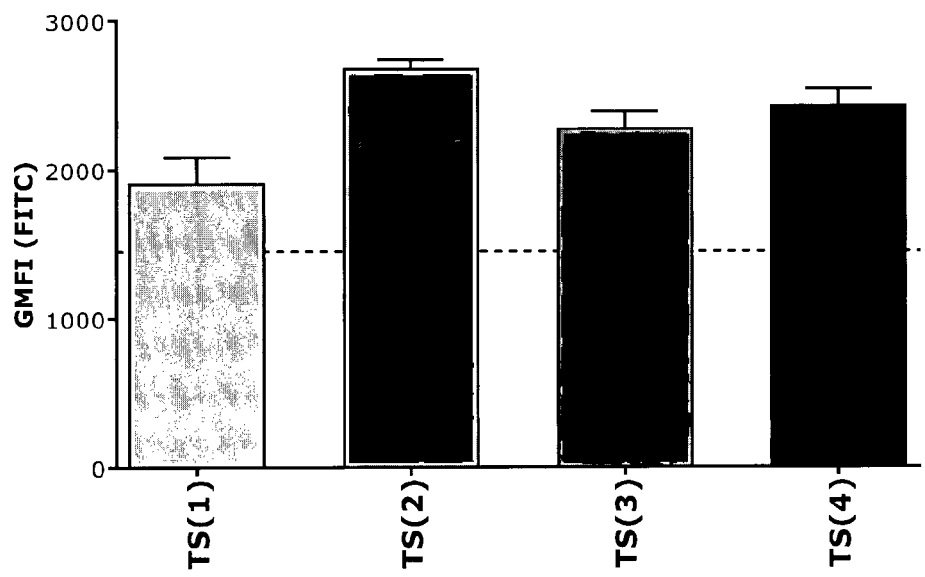

FIG. 22: Surface expression of the HA protein as determined by using flow cytometric analysis (Example 11). The geometric mean of fluorescence intensity (GMFI) was determined for cells transfected with RNA obtained by in vitro transcription in a bioreactor using a standard NTP mix (TS(1)), by sequence-optimized transcription in a bioreactor without feed (TS(2)), by sequence-optimized transcription in a bioreactor with feed (TS(3)), or by sequence-optimized transcription in a bioreactor with reduced T7 RNA polymerase concentration and reduced template concentration (TS(4)), respectively.

Figure 23:
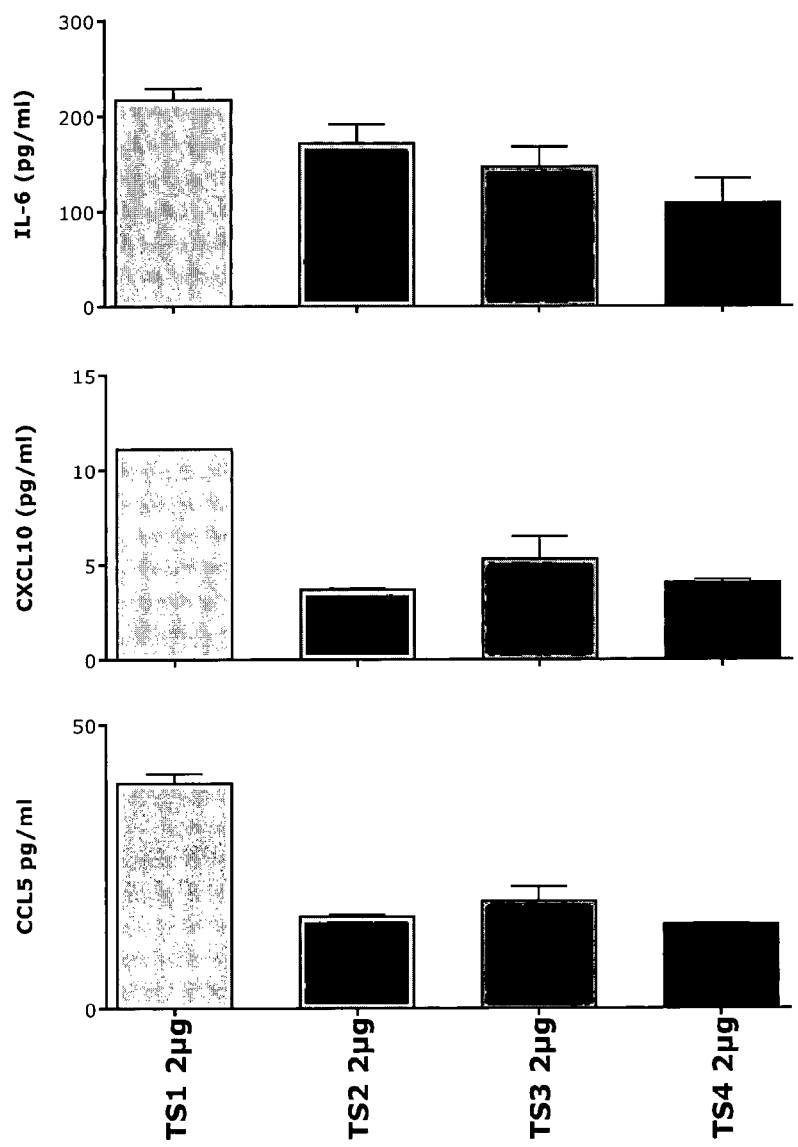

FIG. 23: Immunostimulation by RNA synthesized by in vitro transcription in a bioreactor using a standard NTP mix (TS(1)), by sequence-optimized transcription in a bioreactor without feed (TS(2)), by sequence-optimized transcription in a bioreactor with feed (TS(3)), or by sequence-optimized transcription in a bioreactor with reduced T7 RNA polymerase concentration and reduced template concentration (TS(4)), respectively. Cytokine and chemokine levels in cell supernatants were measured as described in Example 11.

EXAMPLES

The examples shown in the following are merely illustrative and shall describe the present invention in a further way. These examples shall not be construed to limit the present invention thereto.

Example 1: Preparation of the mRNA

1. Preparation of DNA and mRNA Constructs

For the present example DNA sequences encoding *Homo sapiens* prostate stem cell antigen (HsPSCA) mRNA (R1871), *Photinus pyralis* Luciferase (PpLuc) mRNA (R2988) and Mucin-1 signal peptide/epidermal growth factor receptor/Mucin-1 fusion protein (EGFR/Mucin-1) (R1626) were prepared and used for subsequent in vitro transcription reactions.

According to a first preparation, a vector for in vitro transcription was constructed containing a T7 promoter followed by a sequence coding for the above mentioned proteins. The constructs were prepared by modifying the wild type coding sequence by introducing a GC-optimized sequence for stabilization, followed by a stabilizing sequence derived from the alpha-globin-3'-UTR (muag (mutated alpha-globin-3'-UTR)), a stretch of 64 adenosines (poly-A-sequence), a stretch of 30 cytosines (poly-C-sequence), and a histone stem loop.

In addition, a vector for in vitro transcription was constructed containing a T7 promoter followed by the sequence encoding an immunostimulatory RNA (R2025), which does not encode a protein.

The RNA constructs and their nucleotide compositions are listed in Table 1 and Table 2, respectively.

TABLE 1

RNAs

| Description | Identifier (R number) | Sequence | SEQ ID No. |
|---|---|---|---|
| HsPSCA mRNA | R1871 | FIG. 1 | 1 |
| PpLuc mRNA | R2988 | FIG. 2 | 2 |
| EGFR/Mucin-1 mRNA | R1626 | FIG. 3 | 3 |
| Non-coding RNA | R2025 | FIG. 4 | 4 |

TABLE 2

Nucleotide composition of RNAs

| RNA | Length (nt) | G | C | A | U |
|---|---|---|---|---|---|
| HsPSCA | 589 | 150 (25.5%) | 205 (34.8%) | 154 (26.1%) | 80 (13.6%) |
| PpLuc | 1870 | 571 (30.5%) | 604 (32.3%) | 428 (22.9%) | 267 (14.3%) |
| EGFR/Mucin-1 | 5337 | 1630 (30.5%) | 1967 (36.9%) | 1086 (20.3%) | 654 (12.3%) |
| Non-coding RNA | 547 | 114 (20.8%) | 111 (20.2%) | 112 (20.5%) | 210 (38.4%) |

2. In Vitro Transcription

The respective DNA plasmids prepared according to paragraph 1 were transcribed in vitro using T7 polymerase. Subsequently the mRNA was purified using PureMessenger® (CureVac, Tübingen, Germany; WO2008/077592A1).

The standard transcription reaction volume was 20 μl. For subsequent HPLC purification of mRNAs, e.g. for cap analysis, 1 ml reactions were set up.

Linearized DNA plasmid templates (50 μg/ml) were transcribed at 37° C. for three hours (or as indicated) in 80 mM HEPES/KOH, pH 7.5, 24 mM $MgCl_2$, 2 mM spermidine, 40 mM DTT, 5 U/ml pyrophosphatase (Thermo Fisher Scientific), 200 U/ml Ribolock RNase inhibitor (Thermo Fisher Scientific), 5000 U/ml T7 RNA polymerase (Thermo Fisher Scientific). Ribonucleoside triphosphates (NTPs) were added according to sections 3 to 7 below, respectively. Following transcription, the DNA template was removed by DNaseI digestion (Roche) (100 U/ml, 1 mM $CaCl_2$, 30 minutes at 37° C.).

RNAs were precipitated in 2.86 M LiCl in a 3.45-fold reaction volume for 16 hours at −20° C., followed by centrifugation (30 minutes, 16.000 g, 4° C.). Pellets were washed in five transcription reaction volumes of 75% ethanol (invert tubes, centrifuge 5 minutes, 16.000 g, 4° C.), dried and re-dissolved in 2.5 transcription reaction volumes $H_2O$. RNA yields were determined via absorbance measurement at 260 nm using a NanoDrop® Spectrophotometer. One absorbance unit at 260 nm corresponds to 40 ng/μl of RNA (1 A260=40 ng/μl RNA).

To determine the number of incorporated nucleotides, the total amount of RNA produced was converted to the number of molecules produced by dividing by the molecular mass. Multiplying by the number of the respective nucleotide present in the sequence yielded the incorporated nucleotides. To determine the remaining nucleotides (in %) at the end of the transcription reaction, this number was divided by the number of nucleotides available, according to:

$$NTP(\text{remaining})[\%] = \left[1 - \frac{RNA \text{ yield} * \text{number of } NTP \text{ in } mRNA}{[NTP \text{ (start)}] * \text{reaction volume}}\right] * 100 \quad \text{Equation (1)}$$

RNA yield indicates the number of molecules produced per reaction (nmol). The NTP starting concentration [NTP (start)] is indicated in mM, the reaction volume in μl. To calculate the remaining concentration of the respective nucleotides, NTPs available at the beginning of the reaction were multiplied by the percentage of remaining NTPs at the end of a transcription reaction (see above) according to:

$$NTP(\text{remaining})[mM] = NTP(\text{start})[mM] * NTP(\text{remaining})[\%] \quad \text{Equation (2):}$$

3. Standard In Vitro Transcription in the Presence of Cap Analog

For the production of 5'-capped RNAs using cap analog, standard transcription was carried out with 5.8 mM m7G(5')ppp(5')G cap analog, 4 mM ATP, 4 mM CTP, 4 mM UTP, and 1.45 mM GTP (all Thermo Fisher Scientific) (see Table 3). The cap analog and GTP were used at a ratio of 4:1.

TABLE 3

Nucleotide concentrations (mM) for standard in vitro transcription reactions

| RNA | CAP | G | C | A | U |
|---|---|---|---|---|---|
| HsPSCA | 5.8 | 1.45 | 4 | 4 | 4 |
| PpLuc | 5.8 | 1.45 | 4 | 4 | 4 |
| EGFR/Mucin-1 | 5.8 | 1.45 | 4 | 4 | 4 |

TABLE 4

Amount of nucleotides remaining at the end of standard transcription reactions (after 2.5 hours, in percent of nucleotides at the start of the reaction)

| RNA | CAP | G | C | A | U |
|---|---|---|---|---|---|
| HsPSCA | 99.86 | 17.35 | 59.05 | 69.24 | 84.02 |
| PpLuc | 99.96 | 16.39 | 67.94 | 77.28 | 85.83 |
| EGFR/Mucin-1 | 99.99 | 16.37 | 63.42 | 79.80 | 87.84 |

TABLE 5

Nucleotide concentrations (mM) remaining at the end of a standard in vitro transcription reaction (after 2.5 hours)

| RNA | CAP | G | C | A | U |
|---|---|---|---|---|---|
| HsPSCA | 5.79 | 0.25 | 2.36 | 2.77 | 3.36 |
| PpLuc | 5.80 | 0.24 | 2.72 | 3.09 | 3.43 |
| EGFR/Mucin-1 | 5.80 | 0.24 | 2.54 | 3.19 | 3.51 |

The typical yield of RNA transcripts in a standard transcription is about 1.5 mg/ml reaction.

4. In Vitro Transcription in the Presence of Cap Analog Using Double Concentrations of Cap Analog and NTPs (2xCapNTP)

Cap analog and NTP concentrations were doubled compared to standard transcription conditions, so that reactions were carried out in 11.6 mM m7G(5')ppp(5')G cap analog, 8 mM ATP, 8 mM CTP, 8 mM UTP, and 2.9 mM GTP (all Thermo Fisher Scientific) (see Table 3). The cap analog and GTP were used at a ratio of 4:1.

TABLE 6

Nucleotide concentrations (mM) for 2xCapNTP in vitro transcription reactions

| RNA | CAP | G | C | A | U |
|---|---|---|---|---|---|
| HsPSCA | 11.6 | 2.9 | 8 | 8 | 8 |
| PpLuc | 11.6 | 2.9 | 8 | 8 | 8 |
| EGFR/Mucin-1 | 11.6 | 2.9 | 8 | 8 | 8 |

TABLE 7

Amount of nucleotides remaining at the end of 2xCapNTP transcription reactions (after 2.5 hours, in percent of nucleotides at the start of the reaction)

| RNA | CAP | G | C | A | U |
|---|---|---|---|---|---|
| HsPSCA | 99.87 | 23.45 | 62.08 | 71.51 | 85.20 |
| PpLuc | 99.96 | 17.93 | 68.53 | 77.70 | 86.09 |
| EGFR/Mucin-1 | 99.99 | 20.15 | 65.07 | 80.72 | 88.39 |

The typical yield of a transcription using double concentrations of cap analog and NTPs is about 3 mg/ml reaction.

5. Sequence-optimized In Vitro Transcription in the Presence of Cap Analog

For sequence-optimized in vitro transcription reactions the concentration of ribonucleoside triphosphates (NTPs) was calculated for each individual sequence according to the nucleotide composition of the sequence (Table 2) so that the total concentration of all for NTPs was 13.45 mM as in standard transcription reactions. The concentration of the cap analog was four times higher than the calculated concentration for GTP so that a cap/GTP ratio of 4:1 was obtained.

TABLE 8

Nucleotide concentrations (mM) for sequence-optimized in vitro transcription

| RNA | CAP | G | C | A | U |
|---|---|---|---|---|---|
| HsPSCA | 13.6 | 3.4 | 4.7 | 3.5 | 1.8 |
| PpLuc | 16.4 | 4.1 | 4.3 | 3.1 | 1.9 |
| EGFR/Mucin-1 | 16.4 | 4.1 | 5.0 | 2.7 | 1.7 |

TABLE 9

Amount of nucleotides remaining at the end of sequence-optimized transcription (after 2.5 hours, in percent of nucleotides at the start of the reaction)

| RNA | CAP | G | C | A | U |
|---|---|---|---|---|---|
| HsPSCA | 99.86 | 14.83 | 14.71 | 14.57 | 14.83 |
| PpLuc | 99.96 | 14.62 | 14.72 | 14.76 | 14.85 |
| EGFR/Mucin-1 | 99.99 | 14.60 | 14.82 | 14.51 | 15.04 |

TABLE 10

Nucleotide concentrations (mM) remaining at the end of a sequence-optimized in vitro transcription reaction (after 2.5 hours)

| RNA | CAP | G | C | A | U |
|---|---|---|---|---|---|
| HsPSCA | 13.58 | 0.51 | 0.69 | 0.51 | 0.27 |
| PpLuc | 16.39 | 0.60 | 0.64 | 0.45 | 0.29 |
| EGFR/Mucin-1 | 16.40 | 0.60 | 0.74 | 0.40 | 0.25 |

The typical RNA yield of a transcription using sequence-optimized cap analog and NTPs is about 3.9 mg/ml reaction.

6. Sequence-optimized In Vitro Transcription in the Presence of Cap Analog with NTP Feed For sequence-optimized in vitro transcription reactions the concentration of ribonucleoside triphosphates (NTPs) was calculated for each individual sequence according to the nucleotide composition of the sequence (Table 2) so that the total concentration of all for NTPs was 13.45 mM as in standard transcriptions. The concentration of the cap analog was four times higher than the calculated concentration for GTP so that a cap/GTP ratio of 4:1 was obtained (see Table 7).

For the NTP feed, 13.45 mM NTPs without cap analog were added (in a volume of 2.69 µl) to the reaction mix after 2.5 hours. As at this time point >99% of cap analog was still present in the transcription reaction, the 4:1 Cap/GTP ratio could be retained.

TABLE 11

Amount of nucleotides remaining at the end of sequence-optimized transcription with NTP feed (after 5 h, in percent of nucleotides at the start of the reaction)

| RNA | CAP | G | C | A | U |
|---|---|---|---|---|---|
| HsPSCA | 99.75 | 26.3 | 26.2 | 26.1 | 26.3 |
| PpLuc | 99.94 | 26.1 | 26.2 | 26.2 | 26.3 |
| EGFR/Mucin-1 | 99.98 | 26.1 | 26.3 | 26.0 | 26.5 |

The typical RNA yield of a transcription using sequence-optimized cap analog and NTPs followed by NTP feed is around 6.75 mg/ml reaction.

7. Standard In Vitro Transcription of Non-capped RNAs

For the production of non-capped, 5' triphosphate RNAs, transcription was carried out in the presence of 4 mM of each ATP, GTP, CTP and UTP (all Thermo Fisher Scientific). Non-capped RNAs were used as control in the capping analysis assay (FIG. 7).

8. Enzymatic Capping of mRNA

Enyzmatic capping was performed using the ScriptCap™ m7G Capping System (Cellscript, Madison, Wis., USA) according to the manufacturer's instructions. In brief, per reaction, 60 µg of non-capped RNAs were heat-denatured (10 minutes, 65° C.) in a volume of 68.5 µl and immediately cooled on ice (5 minutes). Following addition of reaction components (1× ScriptCap Capping buffer, 1 mM GTP, 0.1 mM SAM, 1000 U/ml ScripGuard RNase Inhibitor, 400 U/ml ScriptCap Capping Enzyme) to a final volume of 100 µl, reactions were incubated for 1 hour at 37° C. RNAs were precipitated in 2.86 M LiCl in a 3.45-fold reaction volume for 16 hours at −20° C., followed by centrifugation (30 minutes, 16.000 g, 4° C.). Pellets were washed in 0.5 reaction volumes 75% ethanol (invert, centrifuge 5 minutes, 16000 g, 4° C.), dried and re-dissolved in $H_2O$. Enzymatically capped RNAs were used as control in the capping analysis assay (FIG. 7).

9. Results

The RNA yield of standard and sequence-optimized in vitro transcription reactions was determined at defined time points for up to two hours as described above (paragraph 2).

Figure 5:
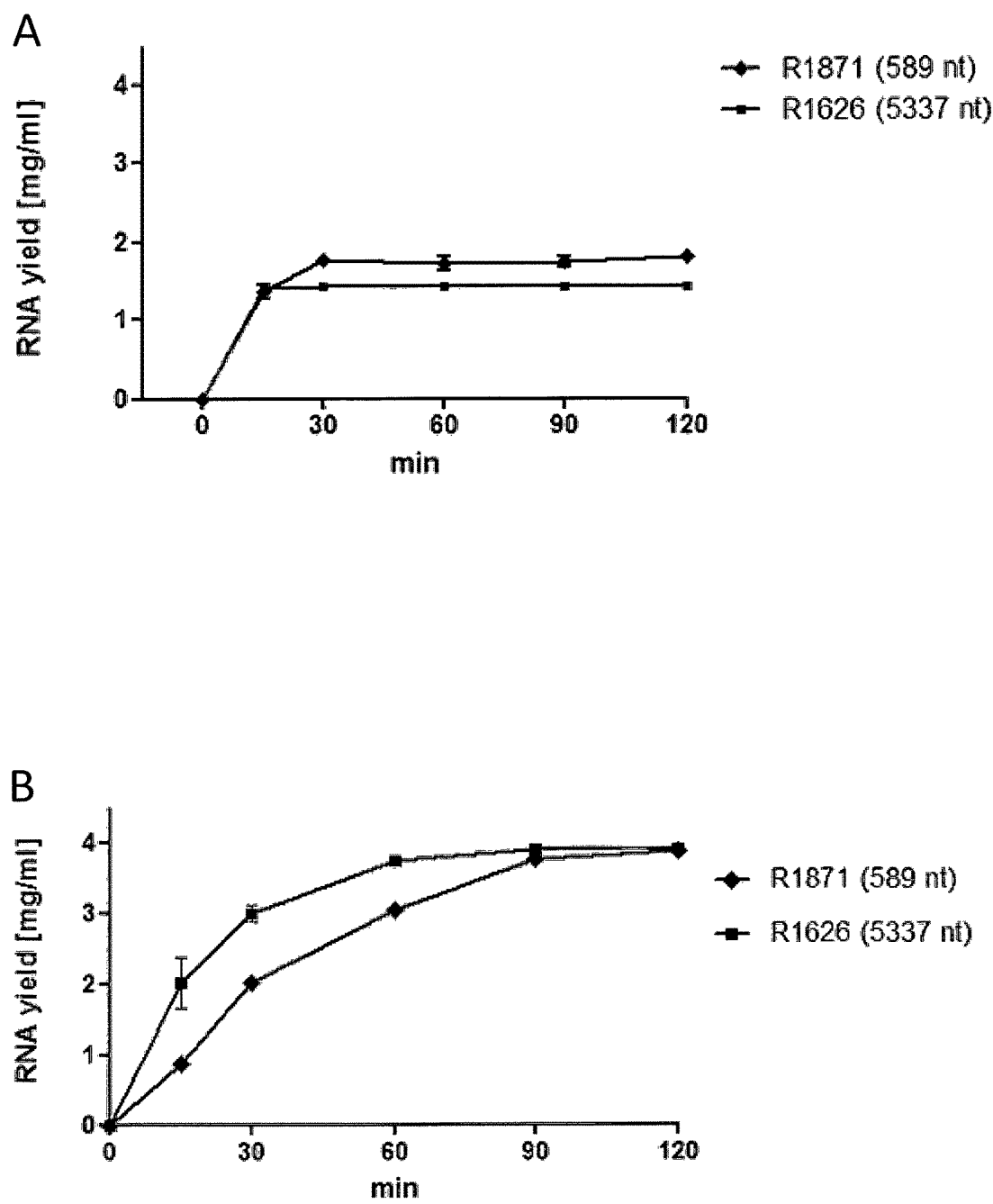
FIG. 5: RNA yields over time for mRNA encoding HsPSCA (R1871) and EGFR/Mucin-1 (R1626). mRNAs were synthesized by in vitro transcription as shown in Example 1.

As can be seen from FIG. 5A, after about 30 minutes the RNA yield of standard transcription reactions reaches a plateau of about 1.4 mg/ml for the 5337 nucleotide long RNA encoding EGFR/Mucin-1 (R1626) and of about 1.8 mg/ml for the 589 nucleotide long RNA encoding HsPSCA (R1871).

As can be seen from FIG. 5B, the RNA yield of sequence-optimized transcription reactions is significantly higher compared to standard transcription reactions. After 60 minutes (R1626) and 120 minutes (R1626), respectively, both RNAs reach a similar plateau of approximately 3.9 mg/ml.

As can be seen from FIG. 6, the RNA yields for the three different RNA molecules of different length are roughly the same for each type of transcription reaction after five hours. Standard transcription (equal NTP concentration) yields about 1.5 mg/ml RNA, transcription with a twofold concentrated Cap-NTP mix (2×CapNTP) about 3.0 mg/ml RNA, sequence-optimized transcription about 3.9 mg/ml RNA and sequence-optimized transcription with NTP feed about 6.75 mg/ml RNA.

Thus, the sequence-optimized transcription reaction results in an about threefold increase in RNA yield compared to standard transcription reactions. This yield can be further increased by about twofold by supplementing the reaction with NTP (NTP feed).

Example 2: CAP Analysis Assay

1. Principle of the Assay

The hammerhead ribozyme HHNUH2d (5'-GCAUG-GCUGAUGAGGCCUCGACCGAUAGGUCGAGGC-CGAAAAGCUUUCUCC C-3') (SEQ ID NO: 5) was incubated with the in vitro transcribed RNAs of example 1 and the cleavage products were separated by denaturing polyacrylamide-gel-electrophoresis (dPAGE).

2. Ribozyme Cleavage Reaction

Per reaction, 10 pmol of HHNUH2d and 10 pmol of the respective generation 4 RNA were annealed in 0.625 mM EDTA in a total volume of 6 µl (2 minutes at 95° C., 0.1° C./seconds to 25° C., 10 minutes at 25° C.). After addition of 4 µl of 100 mM $MgCl_2$, 125 mM Tris/HCl, pH 7.5 (final concentration 40 mM $MgCl_2$, 50 mM Tris/HCl), the reaction was incubated at 25° C. for one hour. For analysis via PAGE, the 1× reaction was stopped with 30 µl 95% formamide, 20 mM EDTA.

3. Gel Separation, Quantification of Cleavage Products and Calculation of Capping Degree Stopped reactions were heat-denatured (heated to 80° C. for 2 minutes, immediately put on ice for 5 minutes) and separated on a 10 cm×8 cm×1.0 mm 20% denaturing polyacrylamide gel (8 M urea (AppliChem), 20% acrylamid:bisacrylamid 19:1 (AppliChem), 1×TBE, 1% APS (AppliChem), 0.1% TEMED (AppliChem); 180 V, 2 hours, Mini-PROTEAN® Tetra Cell (BioRad)). Gels were stained for 10 minutes in 1:10,000 SYBR Gold (Invitrogen) in TBE and documented on a E-BOX VX2 gel documentation system with 312 nm-UV Transilluminator (Peqlab) (excitation maximum for SYBR Gold: ~300 nm, emission: ~537 nm).

To determine the capped proportion in the mRNA preparations, bands of the respective 13-mer (derived from the non-capped fraction) or 14-mer (derived from the capped fraction) cleavage products were quantified using Quantity One 1-D Analysis Software (BioRad). The degrees of capped and non-capped RNA, respectively, were calculated according to:

$$\text{capped } RNA\ (\%) = \frac{\text{signal intensity } 14mer}{\sum \text{signal intensities } (13mer + 14mer)} \times 100 \quad \text{Equation (4)}$$

$$\text{non-capped } RNA\ (\%) = \frac{\text{signal intensity } 13mer}{\sum \text{signal intensities } (13mer + 14mer)} \times 100 \quad \text{Equation (5)}$$

4. Results

As can be seen in FIG. 7, comparable capping efficiencies were achieved for standard and sequence-optimized NTP mixes for *Photinus pyralis* Luciferase (PpLuc) mRNA.

Example 3: Comparison of RNA Yields Using UTP and Pseudo-UTP in Sequence-optimized Nucleotide Mixes In vitro transcription reactions can be performed by replacing one or more of the four nucleotides ATP, GTP, CTP and UTP by nucleotide analogs. Examples of such modified NTPs are pseudouridine (psU or Ψ) triphosphate and 5-methylcytidine (5mC) triphosphate. The percentage of the modified nucleotide in the mix can be varied from 0% to 100% of the natural nucleotide that it replaces.

To test whether it is possible to use modified nucleotides such as pseudouridine (psU) triphosphate in sequence-optimized nucleotide mixes, UTP was replaced by 10%, and 100% pseudouridine triphosphate. In a control reaction, 100% UTP was used.

Sequence-optimized In Vitro Transcription in the Presence of Cap Analog

For sequence-optimized in vitro transcription reactions the concentration of ribonucleoside triphosphates (NTPs) was calculated for each individual sequence according to the nucleotide composition of the sequence (Table 2) so that the total concentration of all for NTPs was 13.45 mM as in standard transcription reactions. The concentration of the cap analog was four times higher than the calculated concentration for GTP so that a CAP/GTP ratio of 4:1 was obtained.

Results

As can be seen from FIG. 8, using UTP and pseudo-UTP in sequence-optimized nucleotide mixes with cap analog (CapNTP mixes) results in comparable RNA yields independent of the pseudo-UTP percentage in the sequence-optimized nucleotide mix. This was demonstrated for two different mRNAs encoding Mucin-1 signal peptide/epidermal growth factor receptor/Mucin-1 fusion protein (EGFR/Mucin-1) (R1626) and prostate stem cell antigen (HsPSCA) mRNA (R1871), respectively.

Example 4: Comparison of Theoretical and Actual RNA Yields Using Standard and Sequence-optimized Nucleotide Mixes Transcription reactions were assembled as described in Example 1, Section 2. The NTPs were either equally distributed (equimolar) or distributed according to the sequence of the produced RNA as described in Example 1, Section 5. For some reactions, an additional nucleotide (GTP or cap analog) was added at a ratio of 4:1 over GTP.

Results

As can be seen from FIG. 9, the actual RNA yield for R2025 can be increased for sequence-optimized NTP mixes compared to standard NTP mixes (equal NTP mix).

As can be seen from FIG. 10, the actual RNA yield for the mRNA encoding *Homo sapiens* prostate stem cell antigen (HsPSCA; R1871) can be increased for sequence-optimized NTP mixes compared to standard NTP mixes (equal NTP mix).

Example 5: Influence of NTP Counter Ions on RNA Yields

The impact of NTP counter ions on RNA yield was investigated using mRNA encoding *Homo sapiens* Mucin-1 signal peptide/epidermal growth factor receptor/Mucin-1 fusion protein (EGFR/Mucin-1, R1626) as example. Transcription reactions were assembled as described in Example 1, Section 2, using sequence-optimized NTP ratios and a total NTP concentration of 13.45 mM. NTPs contained either $Na^+$ or $Tris^+$ (both Thermo Scientific) as counter ions. In addition, Na-NTP reactions were supplemented with different concentrations of NaCl, Tris-NTP reactions with Tris/HCl. After 2.5 hours of reaction time, the RNAs were purified and their concentration was determined as described in Example 1, Section 2.

Results

As can be seen from FIG. 11, the RNA yield for *Homo sapiens* Mucin-1 signal peptide/epidermal growth factor receptor/Mucin-1 fusion protein (EGFR/Mucin-1, R1626) using a sequence-optimized NTP mix remained roughly the same up to a concentration of 150 mM Tris-HCl. By contrast, the RNA yield started to decline at NaCl concentrations above 75 mM.

The negative impact of high NaCl concentrations on RNA yields has been described (e.g. Kern et al., 1997. Biotechnol. Prog., 13, 747-756; U.S. Pat. No. 6,586,218 B2). High concentrations of Na-NTPs, especially as consequence when pursuing a NTP feeding strategy, could therefore result in decreased RNA yields. This limitation should be circumvented with Tris-NTPs, because the polymerase activity is not affected by high Tris/HCl concentrations.

Example 6: Monitoring of the Progress of the Transcription Reaction

Larger-scale transcription reactions (350 µl) of *Homo sapiens* prostate stem cell antigen (HsPSCA; R1871) were assembled as described in Example 1 Section 2, using sequence-optimized NTP ratios and a total NTP concentration of 13.45 mM Tris-NTPs. Cap analog was present in a 4:1 excess over GTP. At defined time points (15/30/60/90/120 minutes after reaction start), a 20 µl sample was taken, the RNA purified and its absorbance at 260 nm determined as described in Example 1, Section 2. A second sample of 40 µl was taken at the same time point and was filtered through a Microcon YM10 device (Merck Millipore, Darmstadt, Germany) (16000*g, 5 minutes, 17° C.). The absorbance of the flow-through at 260 nm, corresponding to unincorporated cap analog and NTPs, was determined using a Nano-Drop® Spectrophotometer according to the instructions of the manufacturer (T009-Technical Bulletin NanoDrop 1000% 8000; Thermo Fisher Scientific, Wilmington, Del., USA).

Results

As can be seen from FIG. 12, the use of a sequence-optimized ribonucleotide mix allows measuring the progress of the in vitro transcription reaction by determining the remaining total nucleotide concentration at defined time points. The decrease in total NTP concentration directly correlates with the amount of synthesized RNA.

Thus, the progress of the transcription reaction can be accurately determined as a function of measured total NTP concentration at a given time point and calculating the moles of NTPs consumed. Based on this information it becomes possible to calculate the amount of synthesized RNA.

This procedure is especially useful to continually monitor the progress of a transcription reaction, for example in a transcription reactor. This would not be possible when a standard NTP mix is used because the consumption of NTPs would not as easily reflect the amount of synthesized RNA.

Example 7: RNA Yields for Sequence-optimized Nucleotide Mixes as a Function of Cap Concentration Transcription reactions were assembled as described in Example 1, section 2, and were carried out at total NTP concentrations of 2 mM, 4 mM, and 13.45 mM NTPs as indicated in FIGS. 14 and 15. The NTPs were distributed according to the sequence of the produced RNA as described in Example 1, section 5 (sequence-optimized ribonucleotide mix for PpLuc and HsPSCA). The reactions were performed at various concentrations (0, 0.25, 2.0, 10, 16 and 20 mM) of the CAP analog (m7G(5')ppp(5')G) as indicated in FIGS. 14 and 15.
Results As can be seen from FIG. 13A, the actual RNA yield for PpLuc mRNA increases with higher cap analog concentrations. The actual RNA yield is higher for the total NTP concentration of 13.45 mM compared to 4 mM. FIG. 13B shows that the relative RNA yield for PpLuc mRNA increases up to a cap analog concentration of approximately 16 mM. The increase in relative RNA yield is stronger for the low NTP concentration (4 mM) than for the high NTP concentration (13.45 mM).

As can be seen from FIG. 14A, the actual RNA yield for HsPSCA mRNA increases with higher Cap analog concentrations. The actual RNA yield is higher for the total NTP concentration of 13.45 mM compared to 4 mM and 2 mM. FIG. 14B shows that the relative RNA yield for HsPSCA mRNA increases up to a cap analog concentration of approximately 16 mM. The strongest increase of the relative RNA yield is observed for the lowest NTP concentration tested (2 mM).

These results demonstrate that the use of a sequence-optimized ribonucleotide mix leads to an increased efficiency of capped RNA synthesis even at low initial total nucleotide concentrations (e.g. at 2 mM). By contrast, it has previous been suggested that for an increased RNA yield high concentrations of total nucleotides, in the order of 12 mM to 40 mM, are necessary (U.S. Pat. No. 6,586,218).

Comparison of PpLuc mRNA (1870 nucleotides) and HsPSCA mRNA (589 nucleotides) shows that the relative RNA yields are independent of the RNA lengths for a defined total NTP concentration.

Example 8: RNA Yields for Sequence-optimized Nucleotide Mixes as a Function of GTP Start Nucleotide Concentration Transcription reactions were assembled as described in Example 1, section 2, and were carried out at a total NTP concentration of the sequence-optimized nucleotide mix of 13.45 mM for P625, P1040 and P532.

The NTPs were distributed according to the sequence of the produced RNA as described in Example 1, section 5 (sequence-optimized ribonucleotide mix for PpLuc, HsPSCA and EGFR/Mucin-1). The reactions were performed by adding defined concentrations (0, 0.25, 2.0, 10, 16 and 20 mM) of GTP start nucleotide to the sequence-optimized NTP mix as indicated in FIGS. 16 to 18.
Results As can be seen from FIGS. 15A and 15B, the actual and relative RNA yield for HsPSCA mRNA increases up to a GTP start nucleotide concentration of approximately 10 mM and declines at higher GTP concentrations.

As can be seen from FIGS. 16A and 16B, the actual and relative RNA yield for PpLuc mRNA slightly increases up to a GTP start nucleotide concentration of approximately 10 mM and then declines at higher GTP concentrations.

As can be seen from FIGS. 17A and 17B, the actual and relative RNA yield for EGFR/Mucin-mRNA increases up to a GTP start nucleotide concentration of approximately 10 mM and declines at higher GTP concentrations.

These results demonstrate that the use of a sequence-optimized ribonucleotide mix and an additional amount of the start nucleotide GTP leads to an increased efficiency of RNA synthesis up to a GTP start nucleotide concentration of approximately 10 mM.

Example 9: Bioreactor

FIG. 18 shows a preferred embodiment of a bioreactor 1 in accordance with the present invention in a schematic illustration. From FIG. 18, the modular structure of the bioreactor 1 becomes evident. Here, the bioreactor 1 consists of several bioreactor modules 2, 3, 4, 5. Reaction module 1 is a reaction vessel used for a continuous or semi-batch process for synthesizing RNA molecules of a given sequence. The reaction module 2 contains resin-immobilized DNA used as a template for the RNA transcription reaction. Here, the immobilization of the DNA allows a repeated usage of the template and reduces the contamination of the desired RNA product by any kind of residual DNA. In addition, the immobilization of the DNA template supersedes the use of the enzyme DNAse for terminal DNA digestion. After transcription, the produced RNA molecules can be released batch by batch or continuously into the capture module 3. The capture module 3 contains a resin/solid phase to capture the RNA molecules and to separate the RNA from other soluble components of the transcription reaction. Thereafter, the RNA molecules can be dispensed from the bioreactor 1 by means of an exit line or the like (not shown) to a receiving unit or the like, in which further RNA elution and purification can be carried out. A washing fluid and/or elution buffer can be provided to the capture module 3 by means of a respective wash and buffer tank 31 connected to the transfer area between reaction module 2 and capture module 3.

In order to be able to monitor and control the transcription process in the reaction module 2, an ultrafiltration membrane 21 for separation of high molecular weight components, such as proteins and polynucleotides, from low molecular weight components, such as nucleotides, is provided in the reaction module 2. The membrane separates a reaction core 22, in which the RNA transcription reaction is carried out, from a filtration compartment 23, in which the filtered reaction mix is received. Based on the nucleotide concentration in the filtrated reaction mix in filtration compartment 23 of the reaction module 2, used as critical process parameter, the feed of nucleotides, buffer components and/or enzymes into reaction module 2 from a feed tank 24 can be controlled and regulated by means of a feed pump 43, which allows performing the RNA transcription reaction in an optimal steady-state condition yielding high transcriptional performance. As a measuring means, a sensor unit 41 is provided for measuring reaction parameters in the reaction mix. Here, the sensor unit 41 at least comprises a sensor for photometric analysis, such as an UV flow cell for UV 260/280 nm, in the filtrated fluid containing the low molecular weight components, which filtrated fluid is extracted from the filtration compartment 23, circulated by a recirculation pump 25 and returned into the filtration compartment 23. In the circulation line, the sensor of the sensor unit 41 is provided in order to achieve real-time monitoring of the filtrated fluid inside the filtration compartment 23. The application of a sequence-optimized ribonucleotide mix in the bioreactor 1 enables a real-time measurement of the nucleotide concentration in the filtration compartment 23 during the RNA transcription reaction in the reaction core 22 of reaction module 2. The sensor unit 41 is part of control module 4, which further comprises a controller 42 and an actuator in the form of feed pump 43. The sensor unit 41 and the feed pump 43 are connected to the controller 42 in order to provide measurement signals to and receive instruction signals from the controller 42. Furthermore, other critical process parameters, such as a pH-value of the filtrated fluid, or a conductivity of the filtrated fluid can be analyzed by further suitable sensors of the sensor unit 41. Data collection and analyses by the controller 42, usually in the form of a computer based system or the like, allows the control of the feed pump 43 as an actuator for repeated feeds of nucleotides, buffer components and/or enzymes into the reaction module 2, as well as the control of further pumps in the bioreactor 1 in order to adjust key process parameters in optimal steady-state reaction conditions.

In order to prevent waste, the bioreactor 1 of the preferred embodiment further comprises a reflux module 5 connected to the capture module 3, which reflux module 5 collects unused raw materials, such as nucleotides and enzymes, and recirculates the same back into the reaction module 2 by means of a reflux pump 51. The reflux module 5 contains immobilized enzymes, such as pyrophosphatase, or resin to capture disruptive components, such as phosphate or the like.

The above described embodiments of the present invention and the accompanying drawings are merely intended to be illustrative and should not be considered as limiting, since modifications of the described invention can be made within the scope of the accompanying claims without departing from the scope of the same.

Example 10: Immunostimulatory Activity of RNA Molecules

In this example the immunostimulatory properties of RNA molecules synthesized with a sequence-optimized NTP mix and a standard equimolar NTP mix were compared. Immunostimulation was determined by measuring cytokine and chemokine levels in the supernatants of cells transfected with mRNA.

Standard and sequence-optimized in vitro transcription reactions for Luciferase mRNA (pPluc) were performed as described in Example 1.

Subsequently the mRNA was purified by LiCl precipitation.

Immunostimulation Assay

HeLa cells were seeded at a density of $4 \times 10^5$ cells per well in a 6-well plate in 2 ml HeLa cell culture medium consisting of Gibco® RPMI 1640 medium supplemented with 25 mM HEPES, 2 mM L-Glutamine and 100 IU/ml penicillin/streptomycin (all Lonza, Basel, Switzerland) and 10% fetal calf serum (Perbio Science, Bonn, Germany). On the next day the cells were transfected with 2 μg of RNA or water-for-injection (WFI) as negative control using Lipofectamine® 2000 (Life Technologies, Darmstadt, Germany, catalog no. 11668-027). Briefly, Lipofectamine® reagent and RNA were each diluted in Opti-MEM® medium (Life Technologies), combined in a ratio of RNA: Lipofectamine® of 1:1.5 and incubated for 20 minutes at room temperature. The negative control contained WFI instead of RNA mixed with Lipofectamine®. In the meantime the cells were washed once with 2 ml Gibco® RPMI 1640 medium supplemented with 25 mM HEPES and 2 mM L-Glutamine (serum free and penicillin/streptomycin free medium) and 2 ml of the serum free and penicillin/streptomycin free medium was added to the cells followed by the addition of 0.5 ml RNA: Lipofectamine® transfection mix. After incubation for 4 hours at 37° C. and 5% CO2, the medium containing the transfection mix was replaced by 2 ml of HeLa cell culture medium.

After 24 hours, cell-free supernatants were collected and the concentrations of IL-6, CXCL10 and CCL5 were measured by Cytometric Bead Array (CBA) according to the manufacturer's instructions (BD Biosciences) using the following kits: Human Soluble Protein Master Buffer Kit (catalog no. 558264), Assay Diluent (catalog no. 560104), Human IL-6 Flex Set (catalog no. 558276), Human CXCL10 Flex Set (catalog no. 558280) and Human CCL5 Flex Set (catalog no. 558324) (all kits from BD Biosciences). The data was analyzed using the FCAP Array v3.0 software (BD Biosciences).

Results

As can be seen from FIG. 19, the levels of secreted IL-6, CXCL10 and CCL5 were lower for the RNA synthesized with the sequence-optimized NTP mix compared to the same RNA synthesized with a standard equimolar NTP mix indicating a lower immunostimulatory activity of the RNA resulting from the sequence-optimized NTP mix.

Example 11: In Vitro Transcription in a Bioreactor

Preparation of the DNA Used for In Vitro Transcription (P1140):

A DNA vector for in vitro transcription (P1140) was prepared by insertion of the following elements into a DNA vector (pCV32(KanR)):
5' UTR: 32L4 (Top-UTR)
ORF: HA from H1N1(Netherlands 2009) (GC-enriched)
3' UTR: Albumin7

In vitro transcription of the obtained DNA vector results in an RNA molecule having a length of 2083 nt. The respective RNA sequence (SEQ ID NO: 6) is illustrated in FIG. 20.

The RNA construct is characterized by the following nucleotide composition:
G=540 (25.92%)
C=676 (32.45%)
A=541 (25.97%)
U=326 (15.65%)
G/C=58.37%

Linearization of the DNA Vector:

The plasmid P1140 was linearized using the following conditions:
0.5 μg plasmid DNA
1.5 μl 10× reaction buffer
1 μl EcoRI
ad 15 μl WFI (water for injection)

The reaction was incubated for 3 h at 37° C. Subsequently a phenol/chloroform extraction and an isopropanol precipitation were performed.

In Vitro Transcription:
Standard Cap/NTP Mix

| Standard Cap/NTP-Mix | 4 µL | Final concentration [mM] |
|---|---|---|
| Cap (100 mM) | 1.16 | 5.8 |
| ATP (100 mM) | 0.8 | 4 |
| CTP (100 mM) | 0.8 | 4 |
| UTP (100 mM) | 0.8 | 4 |
| GTP (100 mM) | 0.29 | 1.45 |
| WFI | 0.15 | |

(Final NTP concentration without Cap is 13.45 mM)
Calculation of NTPs and Cap:

The same total NTP concentration of 13.45 mM as used in the standard transcription reaction is used for sequence-optimized transcription. The fourfold amount of GTP is used for the Cap analog.

| P1140 | G | C | A | U | Cap | total |
|---|---|---|---|---|---|---|
| 2083 nt | 540 | 676 | 541 | 326 | | 2083 |
| % | 25.9 | 32.5 | 26.0 | 15.7 | | 100 |
| mM each (total 13.45 mM NTPs) | 3.5 | 4.4 | 3.5 | 2.1 | | 13.45 |
| Cap analog (4x GTP) | | | | | 13.9 | 13.9 |
| total Cap/NTP conc. [mM] | | | | | | 27.4 |

Preparation of the Sequence-Optimized Cap/NTP Mix for P1140:

| P1140 | G | C | A | U | Cap | H$_2$O (ad 7 µl) | Final volume [µl] |
|---|---|---|---|---|---|---|---|
| per reaction (µl 100 mM NTP) | 0.70 | 0.87 | 0.70 | 0.42 | 2.79 | 1.52 | 7.00 |

5× Transcription Buffer:
400 mM HEPES
120 mM MgCl$_2$
10 mM spermidine
200 mM DTT
25 U/ml inorganic pyrophosphatase 4 Different Transcription Reactions were Tested in a Bioreactor:

As bioreactor, a DasBox Bioreaktor from Dasgip was used. The reaction was stirred at 50 rpm. At the indicated time points, samples of 20 µl each were removed. The RNA concentration was measured by determining the absorption at 260 nm after LiCl precipitation.

Four different conditions were used for in vitro transcription:

1. Transcription Using a Standard NTP Mix

| Reagent | ad 80000 µL |
|---|---|
| Linearized plasmid DNA (P1140) [0.48 µg/µL] (µL) | 8300 |
| 5 x transcription buffer (µL) | 16000 |
| standard Cap/NTP-Mix (µL) | 16000 |
| RNAse inhibitor [40 U/µL] (µL) | 400 |
| T7 RNA Polymerase [200 U/µL] (µL) | 2000 |

| Reagent | ad 80000 µL |
|---|---|
| WFI (µL) | 37300 |
| Final volume | 80000 |

The transcription reaction was incubated for 3 h at 37° C.

Subsequently, 6 µl DNAse I (1 mg/ml) and 0.2 µl CaCl$_2$ solution (0.1 M)/µg DNA template were added to the transcription reaction, and incubated for 2 h at 37° C.

2. Sequence-optimized Transcription (1.5 h without Feed)

| Reagent | ad 80000µ |
|---|---|
| Linearized plasmid DNA (P1140) [0.48 µg/µL] (µl) | 8300 |
| 5 x transcription buffer (µl) | 16000 |
| Sequence-optimized Cap/NTP-Mix (µl) | 28000 |
| RNAse inhibitor [40 U/µl] (µl) | 400 |
| T7 RNA Polymerase [200 U/µl] (µl) | 2000 |
| WFI (µl) | 25300 |
| Final volume | 80000 |

The transcription reaction was incubated for 1.5 h at 37° C.

Subsequently, 6 µl DNAse I (1 mg/ml) and 0.2 µl CaCl$_2$ solution (0.1 M)/µg DNA template were added to the transcription reaction, and incubated for 2 h at 37° C.

3. Sequence-optimized Transcription with Feed

| Reagent | ad 80000 µl |
|---|---|
| Linearized plasmid DNA (P1140) [0.48 µg/µl] (µl) | 8300 |
| 5 x transcription buffer (µl) | 16000 |
| Sequence-optimized Cap/NTP-Mix (µl) | 28000 |
| RNAse inhibitor [40 U/µl] (µl) | 400 |
| T7 RNA Polymerase [200 U/µl] (µl) | 2000 |
| WFI (µl) | 25300 |
| Final volume | 80000 |

The transcription reaction was incubated for 1.5 h at 37° C.

12934.6 µl sequence-optimized Cap/NTP-Mix and 5× transcription buffer were added after 1.5 h. The transcription reaction was incubated for additional 1.5 h at 37° C.

Subsequently, 6 µl DNAse I (1 mg/ml) and 0.2 µl CaCl2 solution (0.1 M)/µg DNA template were added to the transcription reaction, and incubated for 2 h at 37° C.

4. Sequence-optimized Transcription with Reduced T7 RNA Polymerase Concentration and Reduced Template Concentration

| Reagent | ad 80000 µl |
|---|---|
| Linearized plasmid DNA (P1140) [0.48 µg/µl] (µl) | 4200 |
| 5 x transcription buffer (µl) | 16000 |
| Sequence-optimized Cap/NTP-Mix (µl) | 28000 |

-continued

| Reagent | ad 80000 µl |
|---|---|
| RNAse inhibitor [40 U/µl] (µl) | 400 |
| T7 RNA Polymerase [200 U/µl] (µl) | 1000 |
| WFI (µl) | 30400 |
| Final volume | 80000 |

Results:

Transcription in a sequence-optimized transcription mix results in higher concentrations of transcribed RNA compared to transcription under standard conditions (FIG. 21, TS(1)). An a addition feed with nucleotides and transcription buffer further increased the amount of transcribed RNA (FIG. 21, TS(3).

Yield:

| Sample ID | [RNA] (mg) |
|---|---|
| P1140-TS(1) | 130.6 |
| P1140-TS(2) | 317.1 |
| P1140-TS(3) | 656.4 |
| P1140-TS(4) | 312.6 |

Expression and Immunostimulation:

HeLa cells were seeded at a density of $4 \times 10^5$ per well in a 6-well plate in 2 ml HeLa cell culture medium consisting of Gibco® RPMI 1640 medium supplemented with 25 mM HEPES, 2 mM L-Glutamine and 100 IU/ml penicillin/streptomycin (all Lonza, Basel, Switzerland) and 10% fetal calf serum (Perbio Science, Bonn, Germany). On the next day, the cells were transfected with different concentrations of 2 µg RNA or water-for-injection (WFI) as negative control using Lipofectamine® 2000 (Life Technologies, Darmstadt, Germany, catalog no. 11668-027). Briefly, Lipofectamine reagent and RNA were each diluted in Opti-MEM® medium (Life Technologies), combined in a ratio of RNA: Lipofectamine of 1:1.5 and incubated for 20 mM at room temperature. Negative control contained WFI instead of RNA mixed with Lipofectamine2000. In the meantime, the cells were washed once with 2 ml Gibco® RPMI 1640 medium supplemented with 25 mM HEPES and 2 mM L-Glutamine (serum- and penicillin/streptomycin free medium), 2 ml of the serum- and penicillin/streptomycin-free medium was added to the cells following by the addition of 0.5 ml RNA: Lipofectamine transfection mix. Upon incubation for 4 h at 37° C. and 5% CO2, the medium containing the transfection mix was removed and 2 ml of the HeLa cell culture medium were added.

After 24 hours, supernatants and cells were collected.

Protein Expression:

Surface expression of the HA protein was determined using flow cytometric analysis. Adherent HeLa cells were washed once with 1 ml PBS and harvested using trypsin-free detach buffer (40 mM Tris HCl pH 7,5; 150 mM NaCl, 1 mM EDTA). The cells were incubated with mouse monoclonal anti-HA (H1N1) antibody (Immune Technology, New York, USA) followed by a secondary anti-mouse FITC-conjugated antibody (Sigma-Aldrich, Taufkirchen, Germany). The cells were measured on a BD FACS Canto and analyzed using FlowJo Software Version 10.6. Statistical analysis was performed using Graph Pad Prism Software, Version 5.01.

Results:

RNA transcribed in a sequence-optimized reaction mix (FIG. 22, TS(2), TS(3), TS(4)) resulted in a higher expression of the encoded HA protein than RNA transcribed under standard conditions (FIG. 22, TS(1)).

Immunostimulation:

The concentrations of IL-6, CXCL10 and CCL5 were measured in cell-free supernatants by cytometric bead array (CBA) according to the manufacturer's instructions (BD Biosciences) using the following kits:

| reagent | catalog no. |
|---|---|
| Human Soluble Protein Master Buffer Kit | 558264 |
| Assay Diluent | 560104 |
| Human IL-6 Flex Set | 558276 |
| Human CXCL10 Flex Set | 558280 |
| Human CCL5 Flex Set | 558324 |

The data was analyzed using the FCAP Array v3.0 software (BD Biosciences). Statistical analysis was performed using Graph Pad Prism Software, Version 5.01.

Results:

RNA transcribed under standard conditions (FIG. 23, TS1) induced higher levels of the cytokines IL-6, CXCL10 and CCL5 in Hela cells compared to RNAs transcribed in a sequence-optimized reaction mix (FIG. 23, TS2, TS3, TS4).

The invention claimed is:

1. A method for synthesizing a capped mRNA molecule of a given sequence and administering the mRNA to a cell, comprising the following steps:
  a) determining the fraction for each of the four nucleotides G, A, C and U in said mRNA molecule of the given sequence,
  b) synthesizing said mRNA molecule comprising an open reading frame by in vitro transcription in a sequence-optimized reaction mix, wherein said sequence-optimized reaction mix comprises the four ribonucleoside triphosphates (NTPs) GTP, ATP, CTP and UTP, wherein the relative proportion of each of the four ribonucleoside triphosphates in the sequence-optimized reaction mix corresponds to the fraction of the respective nucleotide in said mRNA molecule determined in step (a), a buffer, a DNA template, and an RNA polymerase,
  wherein:
    before the start of the in vitro transcription a cap analog is added to the sequence-optimized reaction mix to produce the capped mRNA; or
    after the in vitro transcription a capping enzyme is used to produce the capped mRNA, and
  c) adminstering the mRNA to a cell.

2. The method of claim 1, wherein step b) comprises the steps of
  b1) preparing a sequence-optimized ribonucleoside triphosphate (NTP) mix comprising the four ribonucleoside triphosphates (NTPs) GTP, ATP, CTP and UTP, wherein the relative proportion of each of the four ribonucleoside triphosphates in the sequence-optimized ribonucleoside triphosphate (NTP) mix corresponds to the fraction of the respective nucleotide in said mRNA molecule determined in step (a), and
  b2) synthesizing said RNA molecule by in vitro transcription in the sequence-optimized reaction mix comprising the NTP mix of step (b1), a buffer, a DNA template, and an RNA polymerase.

3. The method of claim 1, wherein before the start of the in vitro transcription a cap analog is added to the sequence-optimized reaction mix to produce the capped mRNA.

4. The method of claim 3, wherein said cap analog is added in excess compared to-the fraction of that nucleotide in said RNA molecule which is found at the first position of said RNA molecule.

5. The method of claim 1, wherein a part or all of at least one ribonucleoside triphosphate is replaced by a modified nucleoside triphosphate.

6. The method of claim 5, wherein said modified nucleoside triphosphate is selected from the group consisting of pseudouridine-5'-triphosphate, 1-methylpseudouridine-5'-triphosphate, 2-thiouridine-5'-triphosphate, 4-thiouridine-5'-triphosphate and 5-methylcytidine-5'-triphosphate.

7. The method of claim 2, wherein in the course of the in vitro transcription the sequence-optimized reaction mix is supplemented with the sequence-optimized ribonucleoside triphosphate (NTP) mix as defined in claim 2 b1).

8. The method of claim 1, wherein said mRNA molecule is longer than 100 nucleotides.

9. The method of claim 1, wherein the NTP counter ion is tris(hydroxymethyl)-aminomethane (Tris).

10. The method of claim 1, wherein the synthesizing of said mRNA molecule by in vitro transcription is followed by separating and quantifying the unincorporated NTPs.

11. The method of claim 1, wherein the synthesizing of said mRNA molecule by in vitro transcription is carried out in a bioreactor.

12. The method of claim 11, wherein said bioreactor comprises a DNA template immobilized on a solid support.

13. The method of claim 11, wherein said bioreactor comprises a filtration membrane for separating nucleotides from the sequence-optimized reaction mix.

14. The method of claim 1, wherein after the in vitro transcription a capping enzyme is used to produce the capped mRNA.

15. The method of claim 8, wherein said mRNA molecule is between 100 and 10,000 nucleotides in length.

16. The method of claim 1, wherein the mRNA comprises a Poly(A) tail sequence.

17. The method of claim 1, wherein the administration results in lower immunostimulatory activity than if an mRNA synthesized with a standard equimolar NTP mix were administered.

18. The method of claim 1, wherein the administration results in higher expression of a protein encoded by the open reading frame than if an mRNA synthesized with a standard equimolar NTP mix were administered.

\* \* \* \* \*

UNITED STATES PATENT AND TRADEMARK OFFICE
CERTIFICATE OF CORRECTION

Page 1 of 1

PATENT NO. : 10,837,039 B2
APPLICATION NO. : 15/317579
DATED : November 17, 2020
INVENTOR(S) : Aniela Wochner et al.

It is certified that error appears in the above-identified patent and that said Letters Patent is hereby corrected as shown below:

On the Title Page

Item (30) Foreign Application Priority Data, insert:
--Jun. 10, 2014 (WO) ............. PCT/EP2014/001577--.

Signed and Sealed this
Ninth Day of March, 2021

Drew Hirshfeld
*Performing the Functions and Duties of the
Under Secretary of Commerce for Intellectual Property and
Director of the United States Patent and Trademark Office*

SEQUENCE LISTING

```
<160> NUMBER OF SEQ ID NOS: 6

<210> SEQ ID NO 1
<211> LENGTH: 589
<212> TYPE: RNA
<213> ORGANISM: Artificial Sequence
<220> FEATURE:
<223> OTHER INFORMATION: G/C optimized mRNA sequence of R1871 coding for
      Homo sapiens prostate stem cell antigen (HsPSCA)

<400> SEQUENCE: 1
gggagaaagc uuaccaugaa ggccgugcug cucgcgcugc ugauggccgg ccuggcccug      60
cagccgggga ccgcccugcu gugcuacagc ugcaaggccc aggucucgaa cgaggacugc     120
cugcagguug agaacugcac gcagcugggc gagcagugcu ggaccgcccg gauccgcgcc     180
gugggccugc ucaccgugau cagcaagggc ugcagccuga acugcgugga cgacgccag     240
```

```
gacuacuacg ugggcaagaa gaacaucacc ugcugcgaca ccgaccugug caacgccagc    300
ggcgcccacg cccugcagcc cgcggccgcc auccuggccc ugcugccgcc cugggccug     360 cugcucuggg gccccggcca gcugugacca cuaguuauaa gacugacuag cccgaugggc    420
cucccaacgg gccuccucc ccuccuugca ccgagauuaa uaaaaaaaaa aaaaaaaaaa    480
aaaaaaaaaa aaaaaaaaa aaaaaaaaaa aaaaaaaaaa aaaaaugcau ccccccccc     540 cccccccccc cccccccccc caaaggcucu uuucagagcc accagaauu                589
```

```
<210> SEQ ID NO 2
<211> LENGTH: 1870
<212> TYPE: RNA
<213> ORGANISM: Artificial Sequence
<220> FEATURE:
<223> OTHER INFORMATION: G/C optimized mRNA sequence of R2988 coding for
      Photinus pyralis luciferase (PpLuc)

<400> SEQUENCE: 2
```

```
gggagaaagc uuaccaugga ggacgccaag aacaucaaga agggcccggc gcccuucuac     60
ccgcuggagg acgggaccgc cggcgagcag cuccacaagg ccaugaagcg guacgcccug    120
gugccgggca cgaucgccuu caccgacgcc cacaucgagg ucgacaucac cuacgcggag    180
uacuucgaga ugagcgugcg ccuggccgag gccaugaagc ggguacggccu gaacaccaac    240 caccggaucg uggugugcuc ggagaacagc cugcaguucu ucaugccggu gcugggcgcc    300
cucuucaucg gcguggccgu cgccccggcg aacgacaucu acaacgagcg ggagcugcug    360
aacagcaugg ggaucagcca gccgaccgug guguucguga gcaagaaggg ccugcagaag    420
auccugaacg ugcagaagaa gcugcccauc uccaagaaga ucaucaucau ggacagcaag    480
accgacuacc agggcuucca gucgauguac acguucguga ccagccaccu cccgccgggc    540
uucaacgagu acgacuucgu cccggagagc uucgaccggg acaagaccau cgcccugauc    600
augaacagca gcggcagcac cggccugccg aaggggguggg cccugccgca ccggaccgcc    660
ugcgugcgcu ucucgcacgc ccgggacccc aucuucggca ccagaucau cccggacacc    720 gccauccuga gcgugggucgc cguuccaccac ggcuucggca guucacgac ccugggcuac    780 cucaucugcg gcuuccgggu ugguccugaug uaccgguucg aggaggagcu guuccugcgg    840
agccugcaga acuacaagau ccagagcgcg cugcucgugc cgacccuguu cagcuucuuc    900
gccaagagca cccugaucga caaguacgac cugucgaacc ugcacgagau cgccagcggg    960
ggcgccccgc ugagcaagga gguggggcgag gccguggcca gcgguuucca ccucccgggc   1020
auccgccagg gcuacggccu gaccgagacc acgagcgcga uccugaucac ccccgagggg   1080
gacgacaagc cgggcgccgu gggcaaggug uccgguucu cgaggccaa ggugguggac     1140 cuggacaccg gcaagaccu gggcgugaac cagcggggcg agcugugcgu gcggggcccg    1200
augaucauga cgcggcuacgu gaacaacccg gaggccacca acgcccucau cgacaaggac   1260
ggcuggcugc acagcggcga cauccgcuac ugggacgagg acgagcacuu cuucaucguc   1320
gaccggcuga agucggccugau caaguacaag ggccaccagg uggccggccgc cgagcuggag   1380 agcauccugc uccagcaccc caacaucuuc gacgccggcg uggccgggcu gccggacgac   1440
gacgccggcg agcugccggc cgcggugug ugcuggagc acggcaagac caugacggag     1500
aaggagaucg ucgacuacgu ggccagccag guggaccacc ccaagaagcu gcggggcggc    1560
guguguuucg uggacgagggu cccgaagggc cugaccggga agcucgacgc ccggaagauc    1620 cgcgagauccu ugaucaaggc caagaagggc ggcaagaucg ccgugugagg acuaguuaua    1680
```

-continued

```
agacugacua gcccgauggg ccucccaacg ggcccuccuc cccuccuugc accgagauua    1740
auaaaaaaaa aaaaaaaaaa aaaaaaaaaa aaaaaaaaaa aaaaaaaaaa aaaaaaaaaa    1800
aaaaaaugca ucccccccccc cccccccccc cccccccccc ccaaaggcuc uuuucagagc   1860
caccagaauu                                                           1870
```

<210> SEQ ID NO 3
<211> LENGTH: 5337
<212> TYPE: RNA
<213> ORGANISM: Artificial Sequence
<220> FEATURE:
<223> OTHER INFORMATION: G/C optimized mRNA sequence of R1626 coding for
      Homo sapiens Mucin-1 signal peptide/epidermal growth factor
      receptor/Mucin-1 fusion protein (EGFR/Mucin-1)

<400> SEQUENCE: 3

```
gggagaaagc uuaccaugac ccccggcacc cagagcccgu ucuuccugcu ccugcugcuc     60
acggugcuga ccgucgugac cgggaugcgg ccgagcggca ccgccggggc ggcccugcuc    120
gcccugcugg ccgcccugug ccccgccucg cgcgcgcugg aggagaagaa ggugugccag    180
ggcacgagca caagcugac ccagcucggc accuucgagg accacuuccu gagccugcag    240
cggauguuca caacugcga ggucgugcug gcaaccugg agaucaccua cgugcagcgg    300
aacuacgacc ugagcuuccu caagaccauc caggaggugg ccggcuacgu gcugaucgcc    360
cugaacaccg uggagcggau cccgcuggag aaccugcaga ucauccgggg caacauguac    420
uacgagaaca gcuacgcccu ggccguccuc agcaacuacg acgccaacaa gacggggcug    480
aaggagcugc cgaugcggaa ccugcaggag auccugcacg gcgcggugcg cuucucgaac    540
aacccggccc ugugcaacgu ggagagcauc cagugccggg acaucgugag cagcgacuuc    600
cucagcaaca ugagcaugga cuuccagaac caccugggcu cgugccagaa gugcgacccg    660
agcugcccga acggcagcug cuggggcgcc ggcgaggaga acugcagaa gcugaccaag    720 aucaucugcg cccagcagug cagcgggcgg ugccggggca gagcccag cgacugcugc    780 cacaaccagu gcgccgccgg cugcaccggc ccgcgggagu cggacugccu ggugugccgg    840 aaguccgcg acgaggcgac cugcaaggac accugcccgc gcugaugcu guacaacccg    900 accacguacc agauggacgu gaaccccgag ggcaaguaca gcuucggcgc caccugcguc    960
aagaagugcc cccggaacua cguggugacc gaccacggga gcugcgugcg ggccugcggc   1020
gccgacagcu acgagaugga ggaggacggc gugcggaagu gcaagaagug cgagggcccg   1080
ugccggaagg ugugcaacgg caucggcauc ggggaguuca aggacagccu cagcaucaac   1140
gccaccaaca ucaagcacuu caagaacugc accucgauca gcggcgaccu gcacauccug   1200
ccggucgccu ccggggcga cagcuucacc cacacgccgc cgcuggaccc gcaggagcug   1260
gacauccuga gaccgugaa ggagaucacc ggcuuccucc ugauccaggc gugggccgag   1320
aaccgcaccg accugcacgc cuucgagaac cuggagauca ccggggccg accaagcag   1380 cacggccagu ucagccuggc cguggugagc cugaacauca ccagccucgg gcugcggucg   1440
cugaaggaga ucagcgacgg cgacgugauc aucagcggca acaagaaccu gugcuacgcc   1500
aacacgauca acuggaagaa gcuguucggc accagcggcc agaagaccaa gaucaucagc   1560
aaccggggcg agaacagcug caaggccacc gggcaggugu gccacgcccu gugcucgccg   1620
gagggcugcu ggggccccga gccgcgggac ugcgucagcu gccgcaacgu gagccggggc   1680
cgggagugcg uggacaagug caaccuccug gagggcgagc cgcgggaguu cguggagaac   1740
```

-continued

```
agcgagugca uccagugcca cccggagugc cugccccagg cgaugaacau caccugcacc    1800
ggccggggc cggacaacug cauccagugc gcccacuaca ucgacggccc gcacugcgug     1860
aagacgugcc cggccggcgu gaugggcgag aacaacaccc uggucuggaa guacgccgac    1920
gccggccacg ugugccaccu gugccacccg aacugcaccu acggcugcac cgggccgggc    1980
cuggagggcu gccccaccaa cggcccgaag aucccgagca ucgccaccgg cauggugggc    2040
gcgcuccugc ugcugcuggu ggugggcccug gggaucggcc ucuucaugcg cgcgcggcac   2100
aucgugcgga agcggacgcu gcggcggcug cugcaggagc gcgagcuggu cgagccgcug    2160
accccgagcg gcgaggcccc gaaccaggcc uccugcgga uccugaagga gaccgaguuc     2220
aagaagauca aggugcuggg cucgggcgcc uucggcaccg uguacaaggg gcugugggau    2280
cccgagggcg agaaggugaa gauccccgug gccaucaagg agcugcggga ggcgaccagc    2340
ccgaaggcca acaaggagau ccucgacgag gccuacguga uggccagcgu cgacaacccg    2400
cacgugugcc ggcugcuggg caucugccug accagcacgg ugcagcugau cacccagcug    2460
augccguucg gcugccuccu ggacuacgug cgggagcaca aggacaacau cggcagccag    2520
uaccugcuga acuggugcgu gcagaucgcc aagggcauga acuaccugga ggaccggcgc    2580
cuggugcacc gggaccucgc cgcgcggaac guccuggcuga agaccccgca gcacgugaag   2640
aucaccgacu ucgggcuggc caagcugcug ggcgccgagg agaaggagua ccacgccgag    2700
ggcggcaagg ugcccaucaa guggauggcc cuggagagca uccuccaccg gaucuacacc    2760
caccagucgg acguguggag cuacggcgug accgucuggg agcugaugac guucggcagc    2820
aagccguacg acgggauccc ggccagcgag aucagcagca uccuggagaa gggcgagcgg    2880
cugccgcagc cgccgaucug caccaucgac guguacauga ucaugguaa gugcuggaug    2940
aucgacgcgc acucgcggcc caaguucgcc gagcugauca ucgaguucag caagauggcc    3000
cgggacccgc agcgguaccu ggugauccag ggcgacgagc ggaugcaccu cccgagcccg    3060
accgacagca acuucuaccg ggcccugaug gacgaggagg acauggacga cguggucgac    3120
gccgacgagu accugauccc gcagcagggc uucuucagca gcccgucgac cagccggacc    3180
ccgcugcuga gcagccugag cgccaccagc aacaacucga cggucgccug caucgaccgc    3240
aacggccucc agagcugccc caucaaggag acagcuucc ugcagcggua cagcagcgac    3300
ccgaccggcg cgcugaccga ggacagcauc gacgacaccu uccugccggu gccggaguac    3360
aucaaccagu cggugccgaa gcggcccgcc gggagcgugc agaacccggu guaccacaac    3420
cagccgcuga acccggcccc gagccgggac ccgcacuacc aggaccccca cagcaccgcc    3480
gugggcaacc cggaguaccu gaacaccguc cagccgacgu gcgugaacag caccuucgac    3540
agcccggccc acugggccca aagggcucg caccagauca gccucgacaa cccggacuac    3600
cagcaggacu ucuucccgaa ggaggcgaag cccaacggca ucuucaaggg cagcaccgcc    3660
gagaacgccg aguaccugcg ggugccccca cagagcagcg aguucaucgg cgccuccggc    3720
cacgccagcu ccacccccgg gggcgagaag gagacgagcg ccacccagcg guccagcgug    3780
cccuccagca ccgagaagaa cgcggucucc augaccagcu ccgugcugag cucccacagc    3840
cccgggucgg gcagcuccac gacccagggc caggacguga cccugccccc ggccaccgag    3900
cccgccagcg ggucgccgc gacgugggc caggacguca ccagcgugcc cgugacccgc    3960
cccgccugg ggagcaccac gccgccgcc cacgacguca ccuccgcccc cgacaacaag    4020
cccgcgccgg gcagcaccgc cccccccgcc cacggggugga ccuccgcccc cgacacgcgg    4080
ccggccccg gcagcaccgc gccccccgcc cacggcguga ccuccgcccc ggacacccgc    4140
```

-continued

```
ccggccccg gcagcaccgc ccccccgcc cacgggguga ccuccgcccc ggacacgcgg      4200 cccgccccg gcagcaccgc cccgcccgcc cacggcguca cguccgcgcc cgacaaccgc      4260
cccgcccugg ggagcaccgc cccgcccgug cacaacguga ccuccgccag cggcuccgcg      4320
agcgggnccg ccagcacccu cguccacaac ggcacguccg cccgggccac caccaccccc      4380
gccagcaagu ccacgcccuu cagcaucccg ucccaccaca gcgacacccc caccacccug      4440
gcgucccaca gcacgaagac cgacgccucc agcacccacc acuccagcgu gcccccgcug      4500
accagcucca accacagcac guccccgcag cucagcaccg ggguguccuu cuucuuccug      4560
agcuuccaca ucuccaaccu gcaguucaac agccccucg aggaccccag caccgacuac      4620
uaccaggagc ugcagcggga caucuccgag auguccuugc agaucuacaa gcagggcggc      4680
uuccucgggc ugagcaacau caaguuccgc cccggcuccg ucguggugca gcugacccuc      4740
gccuuccggg aggggacgau caacguccac gacguggaga cccaguucaa ccaguacaag      4800
accgaggccg ccagccgcua caaccugacc aucccgacg ugagcgucuc cgacgugccc      4860
uucccguuca gcgcgcaguc cggcgccggc gugcccgggg ccgugugcca gugccggcgc      4920
aagaacuacg ggcagcucga caucuucccc gcccgggaca cguaccaccc gaugagcgag      4980
uacccgaccu accacacccca cggccgcuac guccccccca gcuccaccga ccggagcccc      5040
uacgagaagg uguccgccgg gaacggcggc agcccccuga gcuacaccaa cccggcggug      5100
gccgccgccu ccgccaaccu ggaggaccag guggaccccc ggcugaucga cggcaaguga      5160
ggacuaguua uaagacugac uagcccgaug ggccucccaa cgggcccucc ucccccucuu      5220
gcaccgagau uauuaaaaaa aaaaaaaaaa aaaaaaaaaa aaaaaaaaaa aaaaaaaaaa      5280
aaaaaaaaaa aaaaaaaaua uuccccccccc ccccccccc ccccccccc ccucuag       5337
```

<210> SEQ ID NO 4
<211> LENGTH: 547
<212> TYPE: RNA
<213> ORGANISM: Artificial Sequence
<220> FEATURE:
<223> OTHER INFORMATION: Non-coding immunostimulatory RNA sequence of R2025

<400> SEQUENCE: 4

```
gggagaaagc ucaagcuuau ccaaguaggc uggucaccug uacaacguag ccgguauuuu       60
uuuuuuuuuu uuuuuuuuga ccgucucaag guccaaguua gucugccuau aaaggugcgg      120
auccacagcu gaugaaagac uugugcggua cgguuaaucu cccuuuuuu uuuuuuuuu      180 uuuuuaguaa augcgucuac ugaauccagc gaugaugcug gcccagaucu ucgaccacaa      240
gugcauauag uagucaucga gggucgccuu uuuuuuuuuu uuuuuuuuuu uggcccaguu      300
cugagacuuc gcuagagacu acaguuacag cugcaguagu aaccacgcg gcuauugcag      360 gaaaucccgu ucagguuuuu uuuuuuuuuu uuuuuccgc ucacuaugau uaagaaccag      420
guggagnguc acugcucucg aggucucacg agagcgcucg auacaguccu uggaagaauc      480
uuuuuuuuuu uuuuuuuuuu uugugcgacg aucacagaga acuucuauuc augcaggucu      540
gcucuag                                                              547
```

<210> SEQ ID NO 5
<211> LENGTH: 52
<212> TYPE: RNA
<213> ORGANISM: Artificial Sequence
<220> FEATURE:
<223> OTHER INFORMATION: hammerhead ribozyme HHNUH2d

<400> SEQUENCE: 5
gcauggcuga ugaggccucg accgauaggu cgaggccgaa aagcuuucuc cc        52

<210> SEQ ID NO 6
<211> LENGTH: 2083
<212> TYPE: RNA
<213> ORGANISM: Artificial Sequence
<220> FEATURE:
<223> OTHER INFORMATION: G/C optimized mRNA sequence encoding HA from
      Influenza A H1N1 (Netherlands 2009)

<400> SEQUENCE: 6

```
gggggcgcugc uacggaggu ggcagccauc uccuucucgg caucaagcuu accaugaagg      60
ccauccuggu gguccuccug uacaccuucg ccaccgcgaa cgccgacacg cugugcaucg     120
gcuaccacgc caacaacagc accgacaccg uggacaccgu gcucgagaag aacgucacgg     180
ugacccacuc cgugaaccug cuggaggaca agcacaacgg gaagcucugc aagcugcggg     240
gcgucgcccc gcugcaccuc gggaagugca acaucgccgg cuggauccug ggaacccgg      300
agugcgagag ccuguccacc gcgagcuccu ggagcuacau cguggagacc uccagcuccg     360
acaacggcac gugcuacccc ggcgacuuca ucgacuacga ggagcccgc gagcagcuga      420
gcuccgugag cuccuucgag cgguucgaga ucuuccccaa gaccagcucc uggcccaacc     480
acgacagcaa caaggggguc accgccgccu gcccgcacgc cggcgcgaag ccuucuaca     540
agaaccugau cuggcucgug aagaagggga cagcuacccc aagcugucc aagagcuaca     600
ucaacgacaa gggcaaggag gugcuggucc ucugggggau ccaccaccc agcaccuccg     660
ccgaccagca gagccuguac cagaacgccg acgccuacgu guucgugggc uccagccgcu     720
acuccaagaa guucaagccc gagaucgcca uccggccgaa ggucccgcgac caggagggcc     780
ggaugaacua cuacuggacg cugguggagc cggggacaa gaucaccuuc gaggcgaccg     840
gcaaccucgu ggccccccgc uacgccuucg ccauggagcg gaacgcccgg gagcggcauca     900
ucaucuccga cacccccgug cacgacugca acacgaccug ccagaccccg aagggcgcca     960
ucaacaccag ccugcccuuc cagaacaucc accccaucac gaucgggaag ugccccaagu    1020
acgugaaguc caccaagcug cgccucgcga ccggccugcg gaacgucccg agcauccagu    1080
cccgcgggcu guucggcgcc aucgccgggu ucaucgaggg cgggcuggacc gggauggugg    1140
acggcuggua cggguaccac caccagaacg agcagggcag cgggguacgcc gccgaccuca    1200
aguccacgca gaacgcgauc gacgagauca ccaacaaggu gaacagcguc aucgagaaga    1260
ugaacaccca guucaccgcc gugggcaagg aguucaacca ccuggagaag cggaucgaga    1320
accugaacaa gaaggucgac gacggcuucc ucgacaucug gacguacaac gccgagcugc    1380
uggugcuccu ggagaacgag cgcacccugg acuaccacga cuccaacgug aagaaccucu    1440
acgagaaggu ccggagccag cugaagaaca acgccaagga gaucgggaac ggcugcuucg    1500
aguucuacca caaguccgac aacaccgca uggagucgu gaagaacggg accuacgacu    1560
accccaagua cagcgaggag gccaagcuga accgcgagga gaucgacggc gugaagcucg    1620
aguccacgcg gaucuaccag auccggcga ucuacagcac cgucgccagc cccggugc     1680
ucgugggucag ccugggggcc aucucccucu ggaugugcag caacggcucc cugcagugcc    1740
gcaucugcau cugaccacua gugcaucaca uuuaaaagca cucagccua ccaugagaau    1800
aagagaaaga aaaugaagau caauagcuua ucaucucuu uucuuuuuc guugguguaa     1860
agccaacacc cugucuaaaa aacauaaauu ucuuuaauca uuuugccucu uucucugug    1920
```

| | | | | |
|---|---|---|---|---|
| cuucaauuaa | uaaaaaaugg | aaagaaccua | gaucuaaaaa aaaaaaaaaa | aaaaaaaaaa 1980 |
| aaaaaaaaaa | aaaaaaaaaa | aaaaaaaaaa | aaaaaaaaau | gcauccccc ccccccccc 2040 |
| ccccccccc | ccccaaagg | cucuuuucag | agccaccaga | auu 2083 |